US012734241B2

(12) United States Patent
Bergan et al.

(10) Patent No.: US 12,734,241 B2
(45) Date of Patent: Sep. 15, 2026

(54) BISPHOSPHONATE-LINKED COMPOUNDS

(71) Applicants: OREGON HEALTH & SCIENCE UNIVERSITY, Portland, OR (US); The United States Government as Represented by the Department of Veterans Affairs, Washington, DC (US)

(72) Inventors: Raymond Bergan, Portland, OR (US); Ryan Gordon, Portland, OR (US); Abhinandan Pattanayak, Portland, OR (US)

(73) Assignees: Oregon Health & Science University, Portland, OR (US); The United States Government as Represented by the Department of Veterans Affairs, Washington, DC (US)

( * ) Notice: Subject to any disclaimer, the term of this patent is extended or adjusted under 35 U.S.C. 154(b) by 691 days.

(21) Appl. No.: 17/428,951

(22) PCT Filed: Feb. 6, 2020

(86) PCT No.: PCT/US2020/017071
§ 371 (c)(1),
(2) Date: Aug. 5, 2021

(87) PCT Pub. No.: WO2020/163637
PCT Pub. Date: Aug. 13, 2020

(65) Prior Publication Data

US 2022/0133894 A1 May 5, 2022

Related U.S. Application Data

(60) Provisional application No. 62/801,858, filed on Feb. 6, 2019.

(51) Int. Cl.
*A61K 47/55* (2017.01)
*A61K 31/353* (2006.01)
*A61K 47/54* (2017.01)

(52) U.S. Cl.
CPC .......... *A61K 47/548* (2017.08); *A61K 31/353* (2013.01); *A61K 47/55* (2017.08)

(58) Field of Classification Search
CPC .................................................... A61K 47/548
See application file for complete search history.

(56) References Cited

U.S. PATENT DOCUMENTS

| | | | | |
|---|---|---|---|---|
| 5,854,227 A * | 12/1998 | Hartmann | C07D 499/00 514/91 |
| 10,780,076 B2 * | 9/2020 | Bergan | A61K 31/167 |
| 2010/0137425 A1 | 6/2010 | Bergan et al. | |
| 2011/0065672 A1 | 3/2011 | Kirschenbaum | |
| 2014/0051623 A1 | 2/2014 | Kratz et al. | |
| 2016/0128973 A1 | 5/2016 | Bergan et al. | |
| 2016/0311805 A1 | 10/2016 | Kushner et al. | |
| 2018/0153853 A1 | 6/2018 | Bergan et al. | |

FOREIGN PATENT DOCUMENTS

| | | |
|---|---|---|
| JP | 2014512341 A | 5/2014 |
| JP | 2014514288 A | 6/2014 |
| JP | 2017534627 A | 11/2017 |
| WO | WO2012098222 A1 | 7/2012 |
| WO | WO2016081281 A1 | 5/2016 |
| WO | WO2019007447 A1 | 1/2019 |

OTHER PUBLICATIONS

West, Solid State Chemistry and Its Applications, john Wiley & Sons, 1984.*
Venkatesh, J. Pharm. Sci. 89, 145-154 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Extended European Search Report and Written Opinion mailed Jun. 12, 2023 for European Patent Application No. 20752874.6, 15 pages.
Farrell, et al, "Biophosphate conjugation for bone specific drug targeting," Bone Reports, vol. 9, 2018, pp. 47-60.
Tsaur, et al, "Combining anticancer drugs with osteoprotective agents in prostate cancer—A contemporary update," Urologic Oncology; Seminars and Original Investigations, vol. 36, No. 11, 2018, pp. 488-497.
Hussain, et al., "Enzalutamide in Men with Nonmetastatic, Castration-Resistant Prostate Cancer," N. Engl. J. Med., vol. 378, No. 26, 2018, pp. 2465-2474.
Kitagawa, et al., "Aryloxyacetic acid diuretics with uricosuric activity. II. Substituted [(4-oxo-4H-1-benzopyran-7-yl)oxy] acetic acids and the related compounds," Chem. Pharm. Bull., vol. 39, No. 10, 1991, pp. 2681-2690.
Xu, et al., "Precision therapeutic targeting of human cancer cell motility," Nat. Commun., vol. 9, No. 1, 2018, 14 pages.
Zhang, et al., "A Multifunctional Therapy Approach for Cancer: Targeting Raf1-Mediated Inhibition of Cell Motility, Growth, and Interaction with the Microenvironmen," Mol. Cancer Ther., vol. 19, No. 1, 2020, pp. 39-51.
Canadian Office Action mailed on Nov. 21, 2023 for Canadian Patent Application No. 3,128,239, a foreign counterpart to U.S. Appl. No. 17/428,95, 4 pages.
Office Action for Japanese Application No. 2024-204340, Dated Feb. 5, 2026, 4 pages.
Japanese Office Action mailed Feb. 13, 2024 for Japanese Application No. 2021-545859, a foreign counterpart to U.S. Appl. No. 17/428,951, 10 pages.

* cited by examiner

*Primary Examiner* — Nizal S Chandrakumar
(74) *Attorney, Agent, or Firm* — Lee & Hayes, P.C.

(57) ABSTRACT

The present invention concerns novel compounds useful in the treatment of cancer, particularly including compounds linking a bisphosphonate moiety with KBU2046, and pharmaceutically acceptable salts, co-crystals, polymorphs, solvates, hydrates, and enantiomers thereof, as well as methods for their production and pharmaceutical compositions comprising them.

17 Claims, 26 Drawing Sheets

Specification includes a Sequence Listing.

```
                              SEQUENCE LISTING

<160> NUMBER OF SEQ ID NOS: 3

<210> SEQ ID NO 1
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 1

ggtgaaaccc cgtctctact                                                   20


<210> SEQ ID NO 2
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 2

ggttcaagcg attctcctgc                                                   20


<210> SEQ ID NO 3
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 3

cgcccggcta atttttgtat                                                   20
```

BISPHOSPHONATE-LINKED COMPOUNDS

CROSS REFERENCE TO RELATED APPLICATIONS

This is the U.S. National Phase of International Patent Application No. PCT/US2020/017071, filed Feb. 6, 2020, which claims priority to and the benefit of the earlier filing date of U.S. Provisional Application No. 62/801,858, filed on Feb. 6, 2019, each of which is incorporated by reference herein in its entirety.

FIELD OF THE INVENTION

The present invention concerns novel compounds useful in the treatment of cancer and to treat a side-effect of the cancer—bone destruction, particularly including compounds linking a bisphosphonate moiety with KBU2046, and pharmaceutically acceptable salts, co-crystals, polymorphs, solvates, hydrates, and enantiomers thereof.

INCORPORATION BY REFERENCE OF SEQUENCE LISTING

A computer readable text file, entitled "2JB4268.txt (Sequence Listing.txt)" created on or about Aug. 5, 2021, with a file size of 4,096 bytes, contains the sequence listing for this application and is hereby incorporated by reference in its entirety.

BACKGROUND OF THE INVENTION 3-(4-fluorophenyl)chroman-4-one (KBU2046), a first-in-class HSP90 activity modulator, may be synthesized as described in US Patent Application Publication No. 2016/0128973 (Bergan et al. —Northwestern University), titled Inhibition of Cancer Cell Motility. KBU2046 inhibits metastasis across murine models of human prostate and breast cancer, decreases bone destruction, and prolongs survival at nanomolar concentrations after oral administration.

There remains a need for improved delivery and efficacy of oncology agents for the treatment of cancers of the bone, including metastatic cancers that locate to the bone, including metastatic cancers of the breast, prostate, lung, kidney, thyroid, bladder, esophagus, stomach, liver, pancreas, testicles, skin, head and neck, lymphomas, multiple myelomas, and sarcomas from the soft tissue or bone.

BRIEF SUMMARY OF THE INVENTION

Provided is a compound of the formula:

(I)

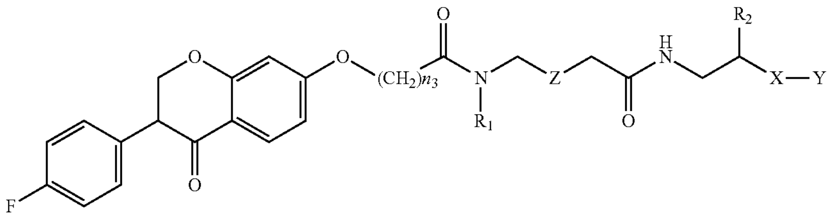

wherein:

Z is selected from the group of:

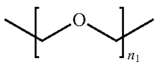

and

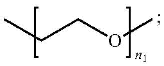

;

$n_1$ in each instance is an integer selected from the group of 1, 2, 3, 4, 5, and 6;

X is $(—CH_2—)_{n2}$;

$R_1$ is selected from the group of H and $C_1$-$C_3$ alkyl;

$R_2$ is selected from the group of H and OH;

$n_2$ is an integer selected from the group of 0, 1, 2, and 3;

$n_3$ is an integer selected from the group of 0 and 1; and

Y is a bisphosphonate compound;

or a pharmaceutically acceptable salt, co-crystal, polymorph, solvate, hydrate, or enantiomer thereof.

In some embodiments, $R_1$ is selected from the group of methyl and ethyl.

In some embodiments, $R_1$ is methyl.

In some embodiments, $R_1$ is ethyl.

In other embodiments, $R_1$ is H.

In some embodiments, $R_2$ is H.

In other embodiments $R_2$ is OH.

In some embodiments, $n_1$ is an integer selected from the group of 1, 2, 3, 4, and 5.

In some embodiments, $n_1$ is an integer selected from the group of 1, 2, 3, and 4.

In some embodiments, Y is selected from structures of the group below, indicated by their corresponding bisphosphonate entity:

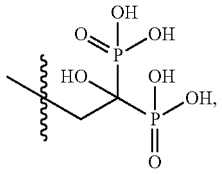

Etidronate

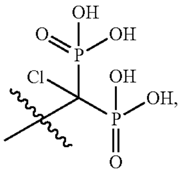

Clodronate

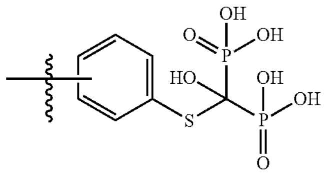

Tiludronate

-continued

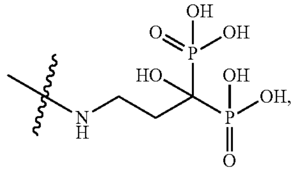

Pamidronate

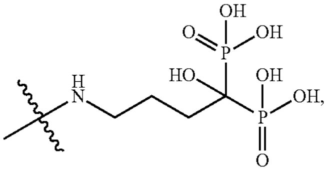

Alendronate

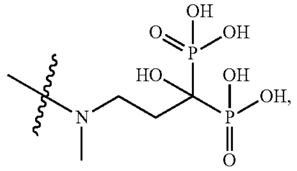

Olpadronate

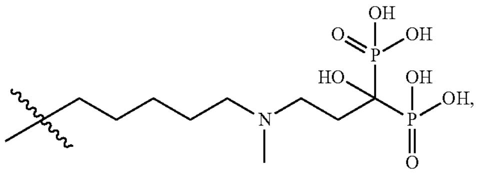

Ibandronate

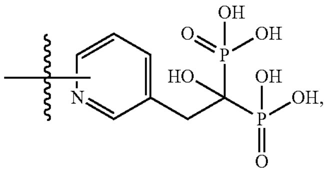

Risedronate

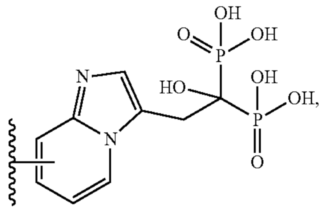

Minodronate

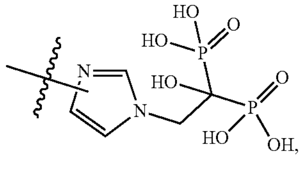

and

Zoledronate

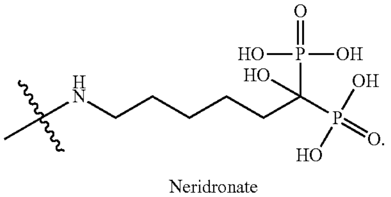

Neridronate

In the structures herein, the waving or oscillating line passing through a solid line

indicates the bond through which adjacent atoms are bound.

BRIEF DESCRIPTION OF THE MANY VIEWS OF THE DRAWINGS

FIG. 1A graphs the effect of chemotherapy on the growth of androgen independent PC3-M PCa cells in vitro.

FIG. 1B graphs the effect of chemotherapy on the growth of androgen independent PCa cells in vivo.

FIG. 2A graphs lung metastasis measured by qPCR for human Alu sequences, expressed as percent control.

FIG. 2B represents weekly IVIS imaging of tumor.

FIG. 2C indicates corresponding tumor weight in tested mice.

FIG. 3A indicates effects on AR-responsive gene selection in LNCaP cells treated with R1881 (R), KBU2046 and/or enzalutamide.

FIG. 3B indicates effects on AR-responsive gene selection in VCaP cells treated with R1881 (R), KBU2046 and/or enzalutamide.

Figure 3A:
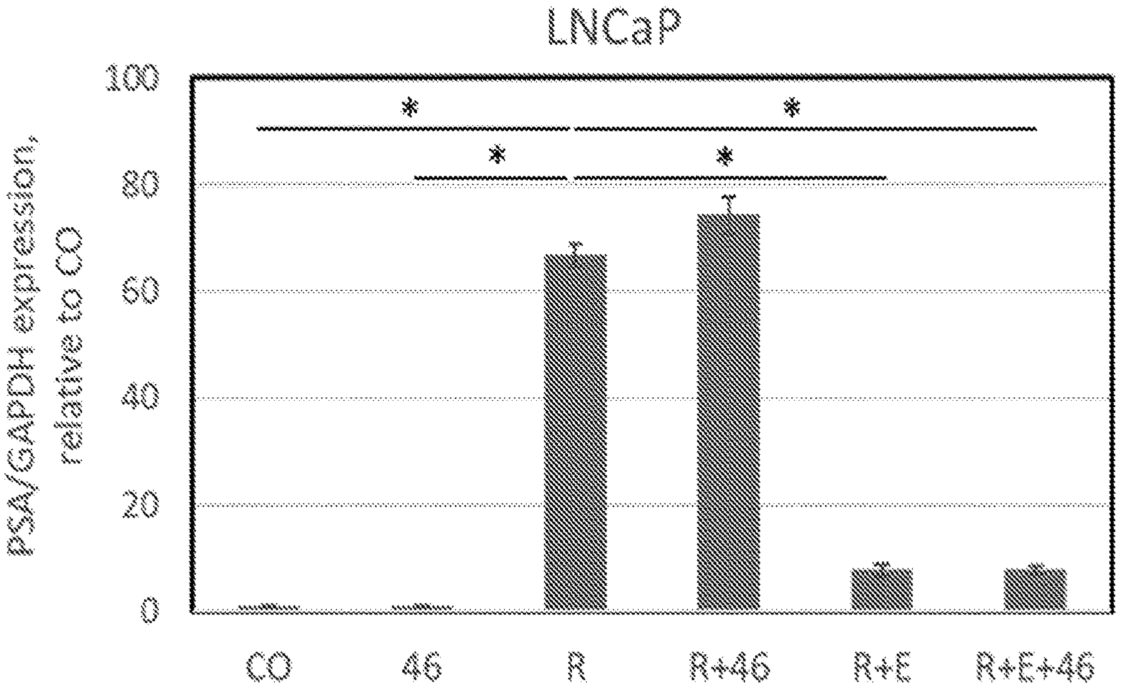
FIG. 3C depicts effects of enzalutamide on LNCaP cell growth.
FIG. 3D depicts effects of enzalutamide on VCaP cell growth.
FIG. 3E represents effects on AR activation through Western blots of nuclear (N) and cytoplasmic (C) preparations of cell extracts probed for AR, laminin 1 or α-tubulin.
Figure 3B:
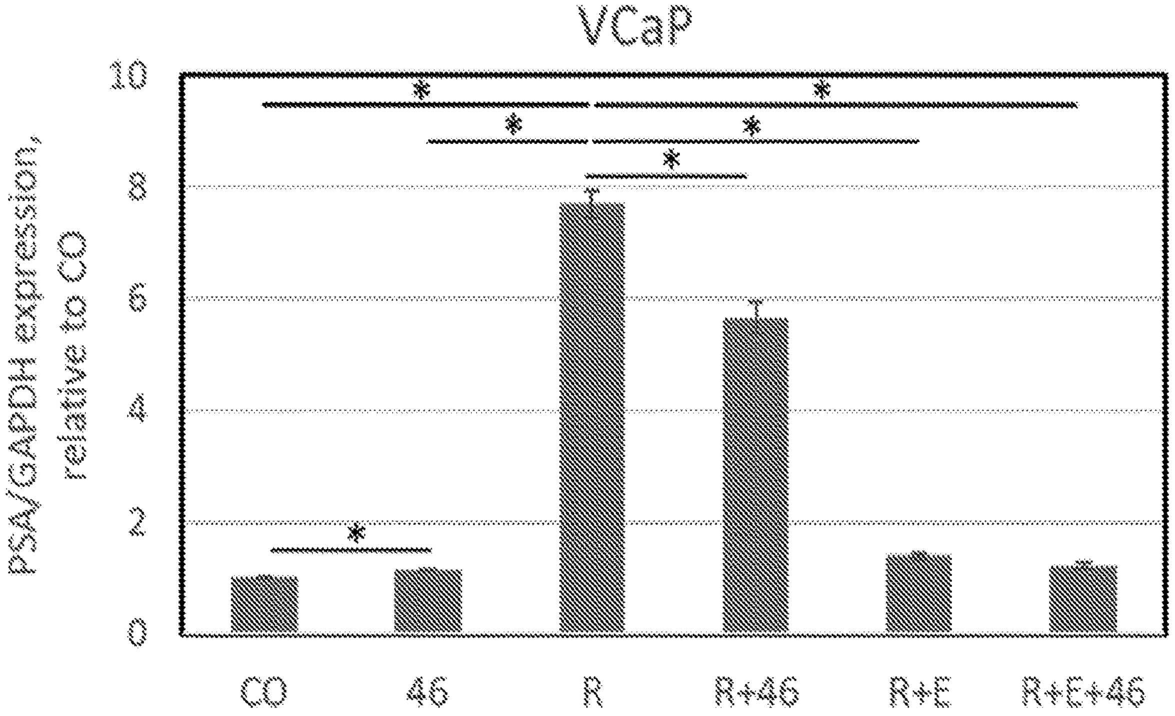
Figure 3C:
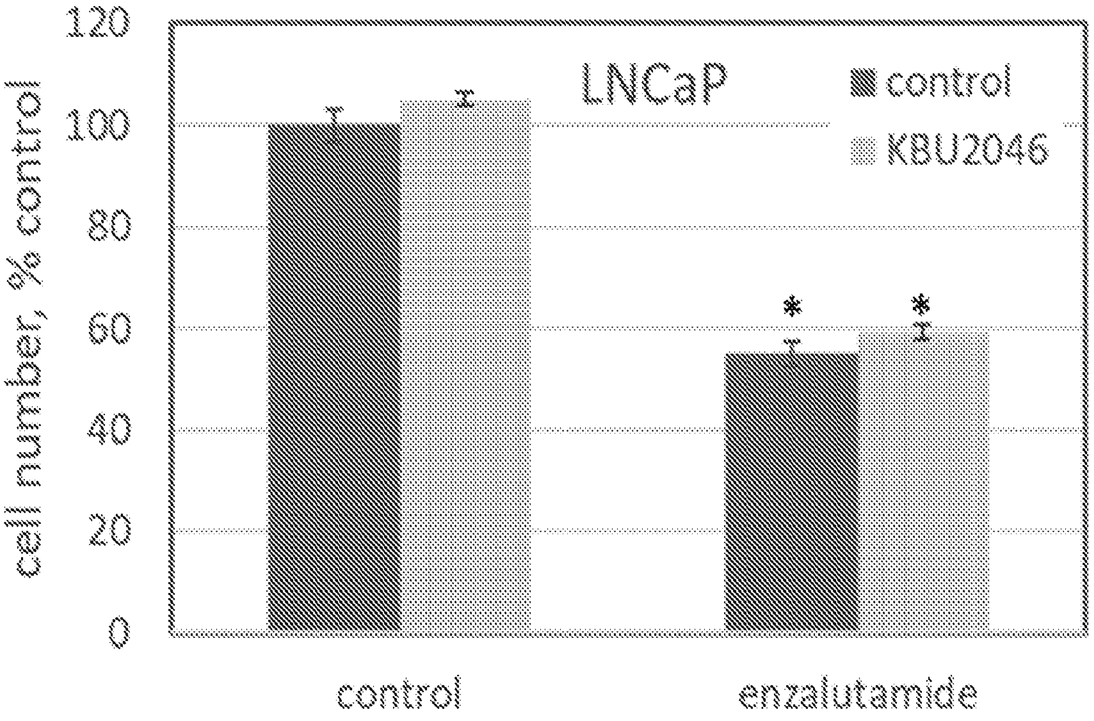
Figure 3D:
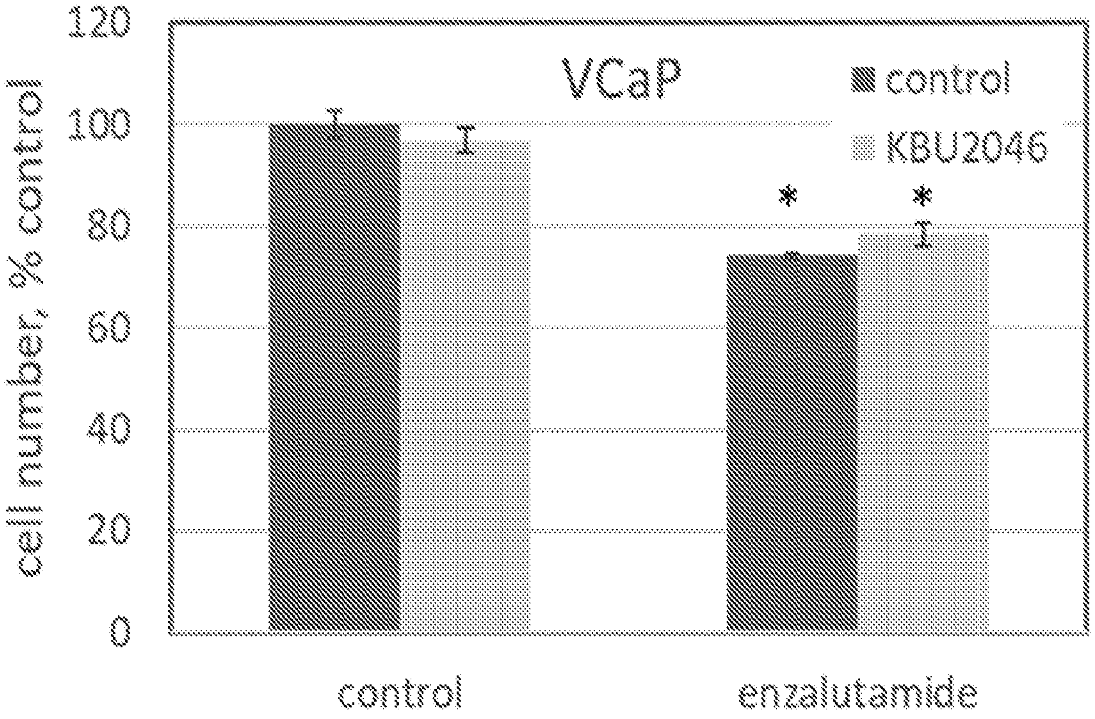
Figure 3E:
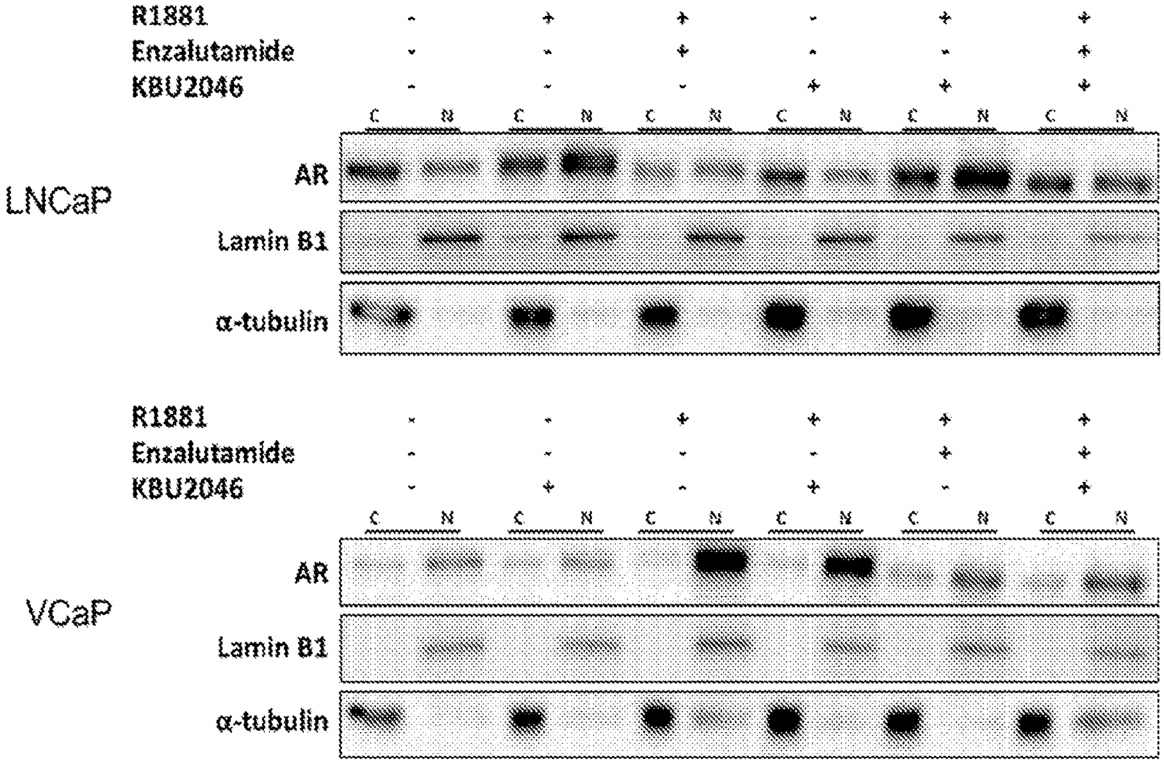
Figure 3F:
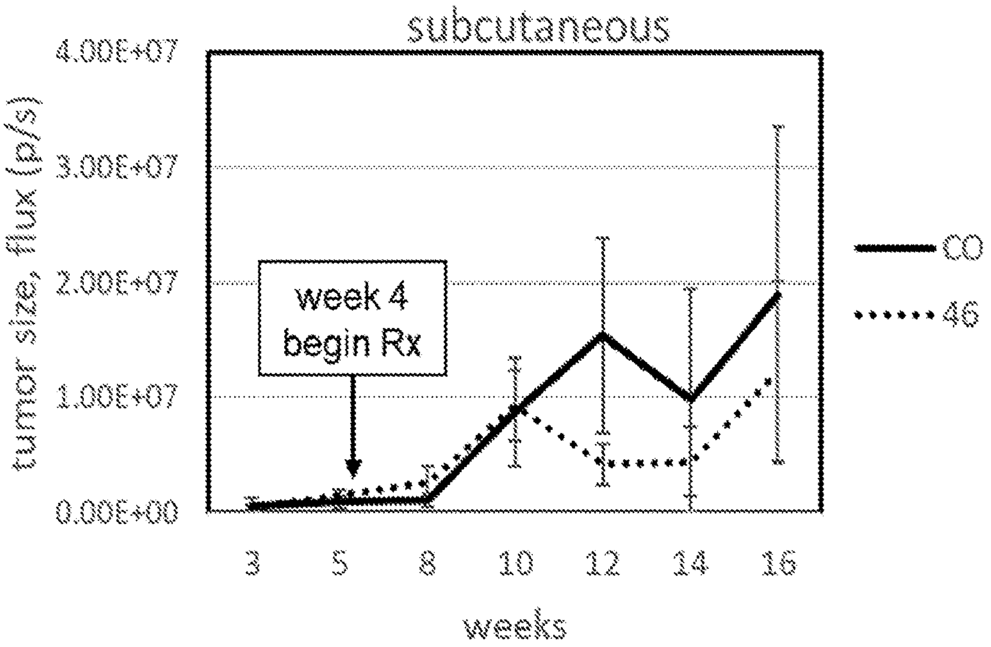

FIG. 3F graphs the effect on tumor outgrowth after androgen deprivation therapy in LNCaP/AR-luc cells implanted subcutaneously into castrate mice, followed by KBU2046 treatment.

Figure 3G:
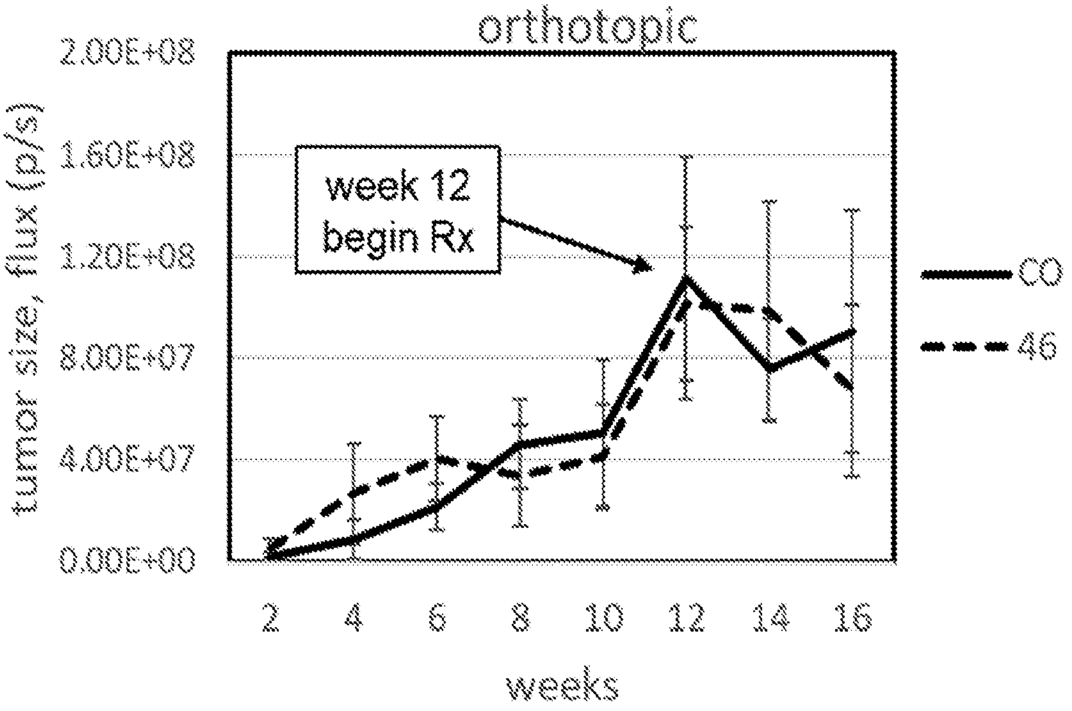

FIG. 3G graphs the effect on tumor outgrowth after androgen deprivation therapy in LNCaP/AR-luc cells implanted orthotopically into castrate mice, followed by KBU2046 treatment.

Figure 4A:
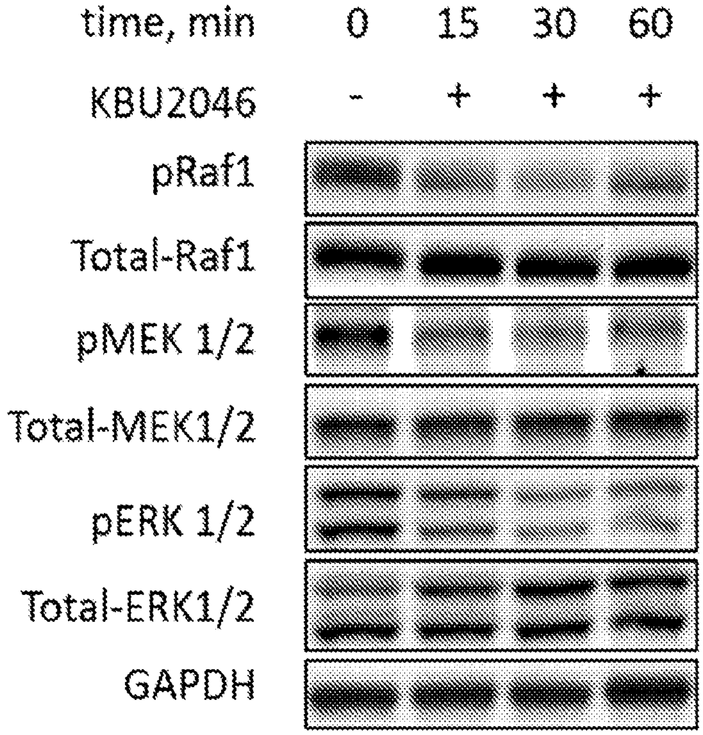

FIG. 4A provides Western blot representations of protein production following KBU2016 administration in RAW 267.4 cells.

Figure 4B:
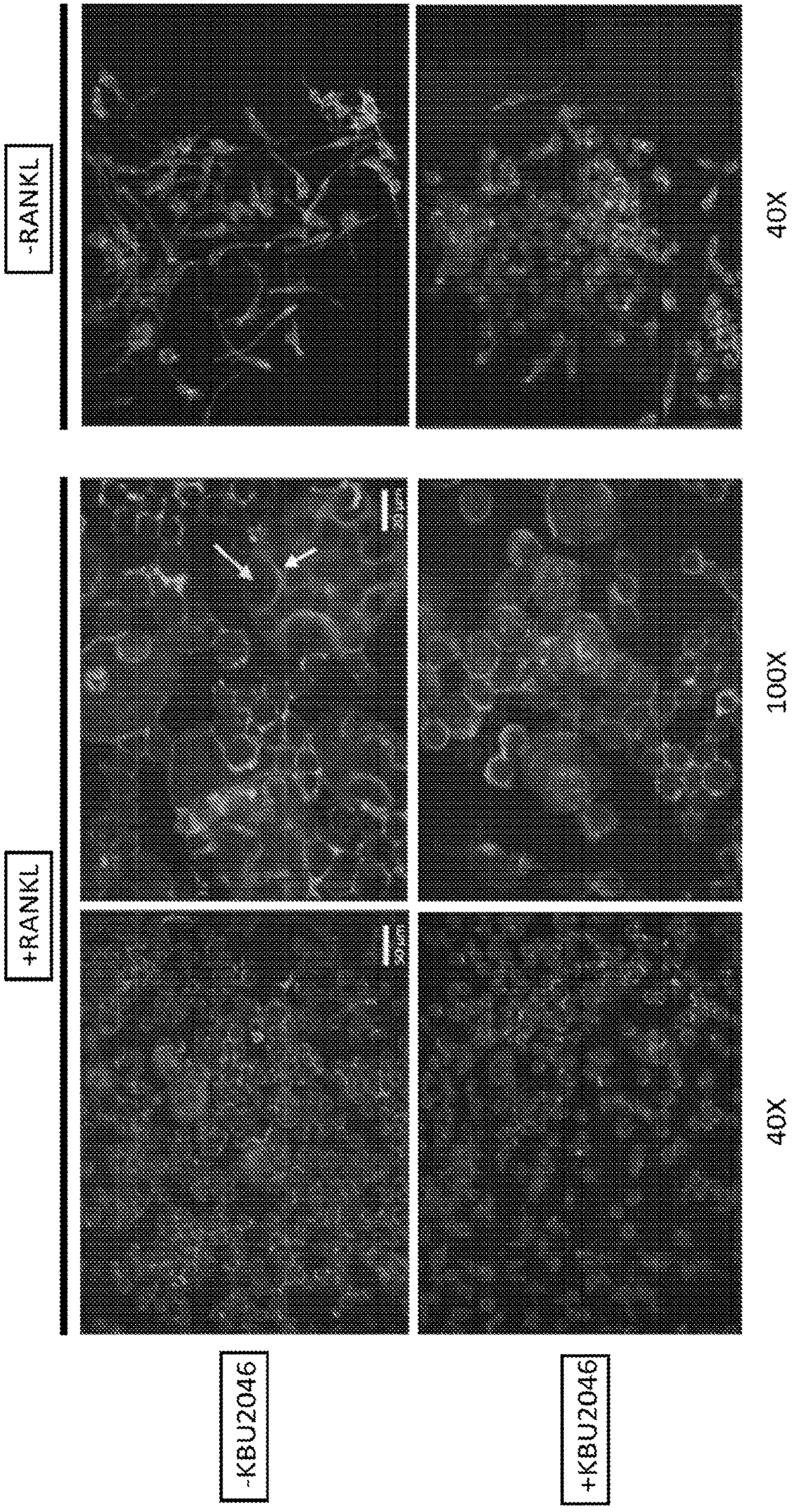

FIG. 4B depicts effects on cell morphology when RAW 267.4 cells were treated with RANKL and with KBU2046.

Figure 4C:
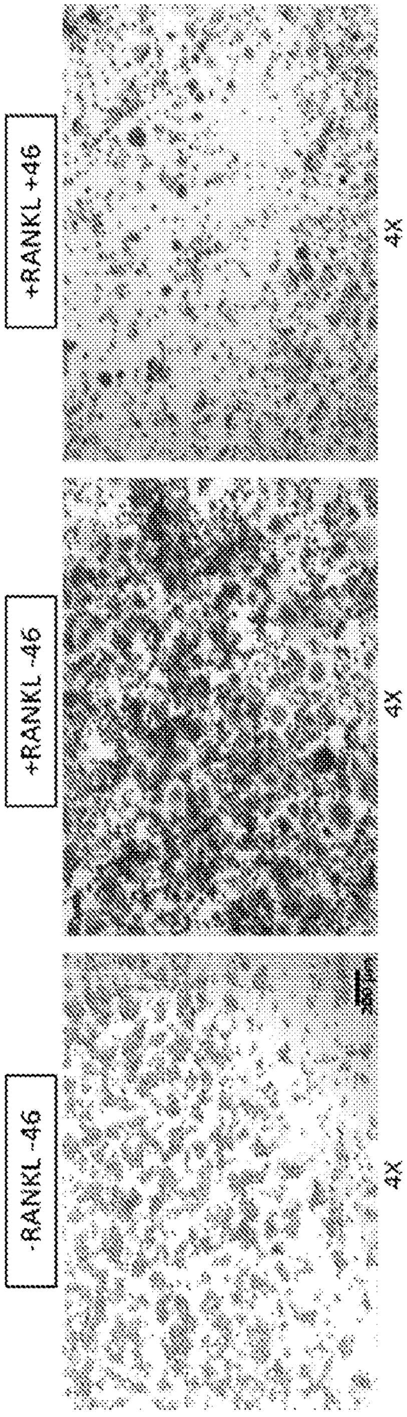

FIG. 4C demonstrates tartrate resistant acid phosphatase expression in treated cells.

Figure 4D:
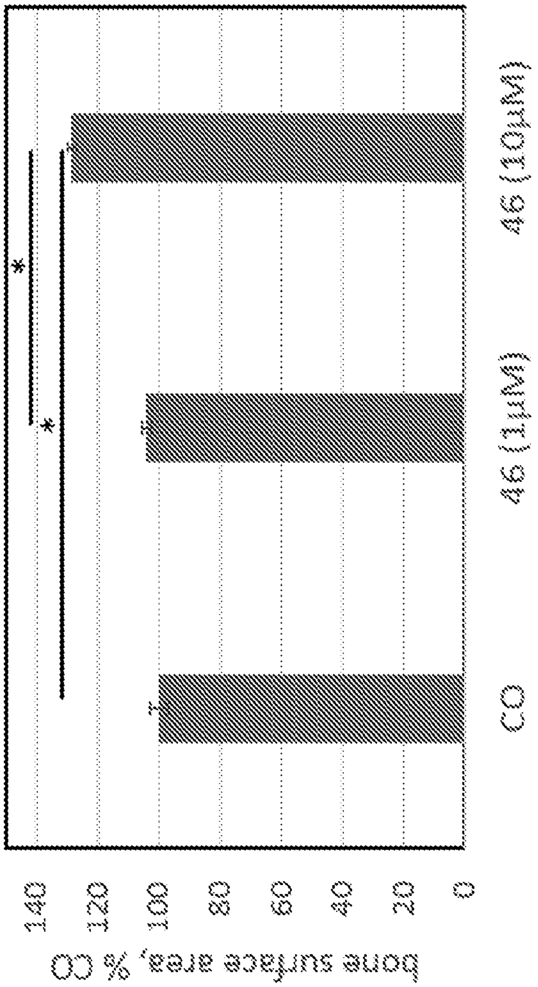

FIG. 4D graphs bone degradation as quantified bone surface area.

Figure 5A:
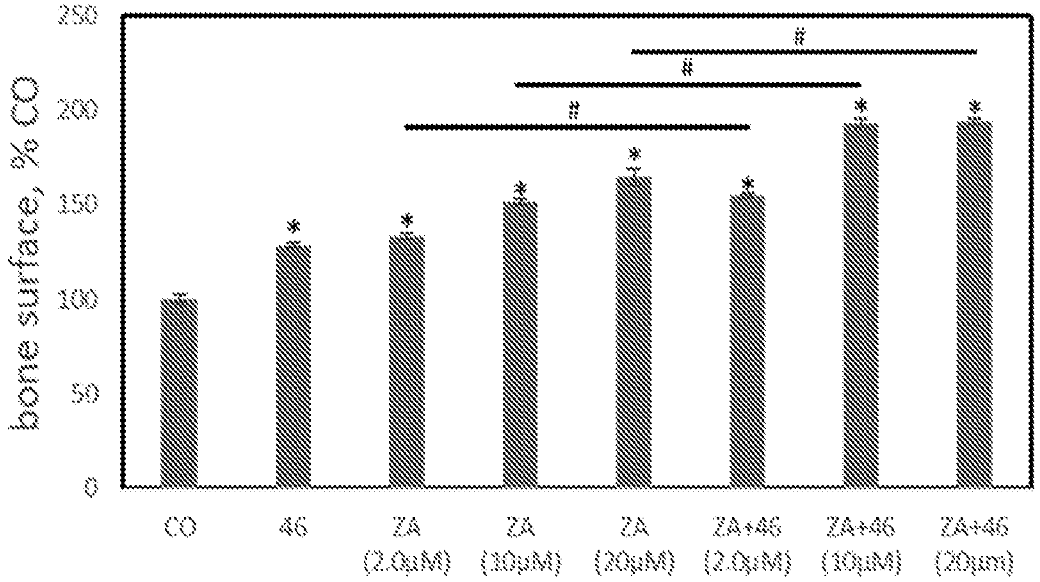

FIG. 5A graphs bone degradation as quantified bone surface area when RAW 267.4 cells were treated with KBU2046, zoledronic acid, or the combination.

Figure 5B:
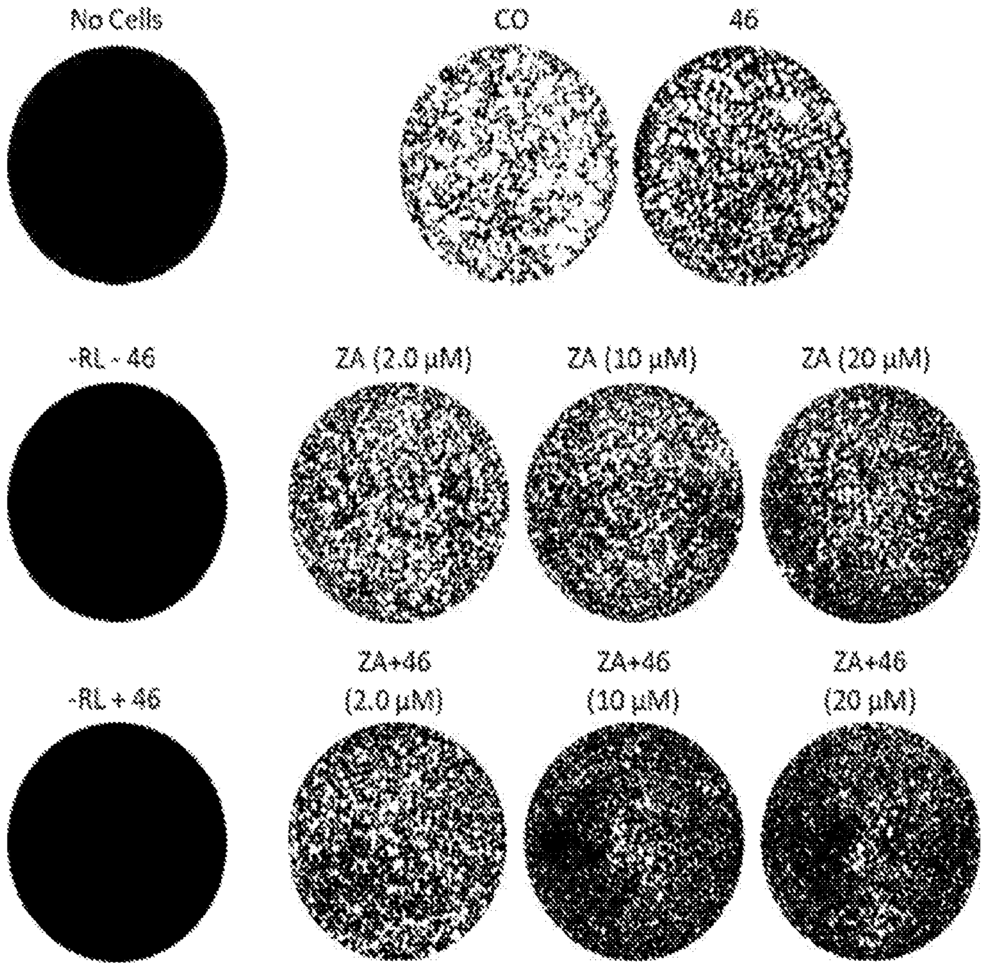

FIG. 5B depicts effects on bone degradation when RAW 267.4 cells were treated with KBU2046, zoledronic acid, or the combination.

Figure 5C:
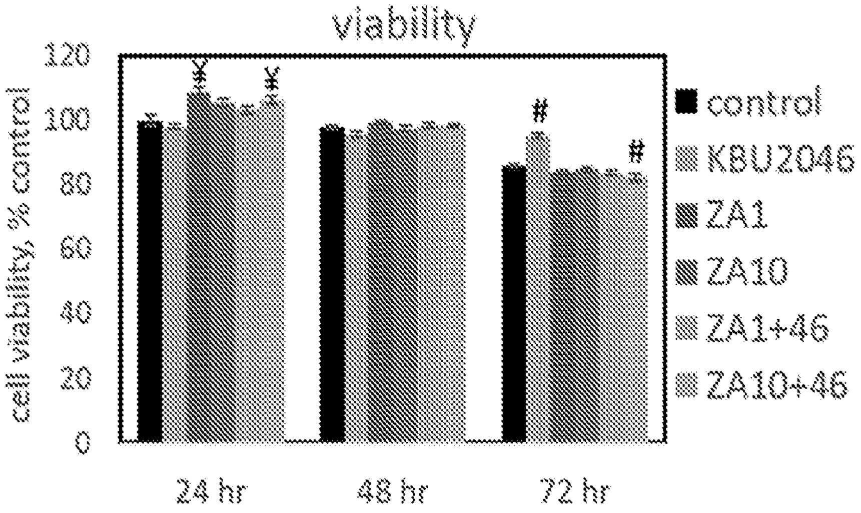
Figure 5D:
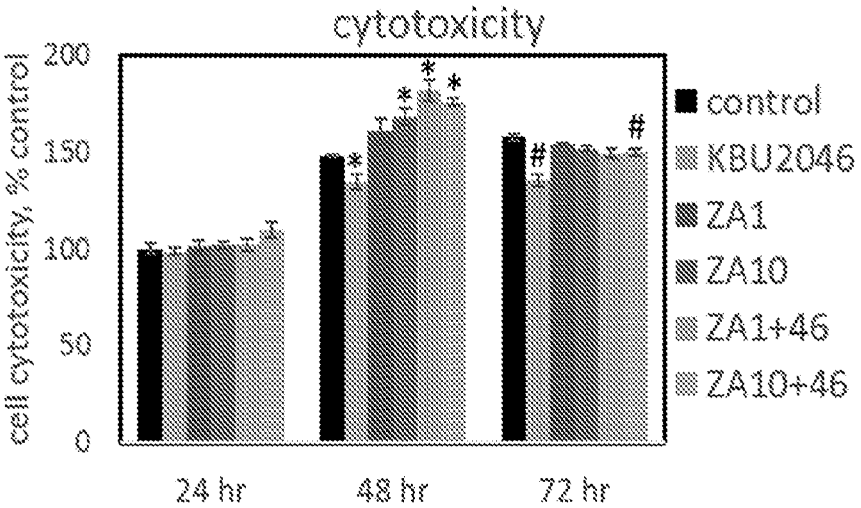
Figure 5E:
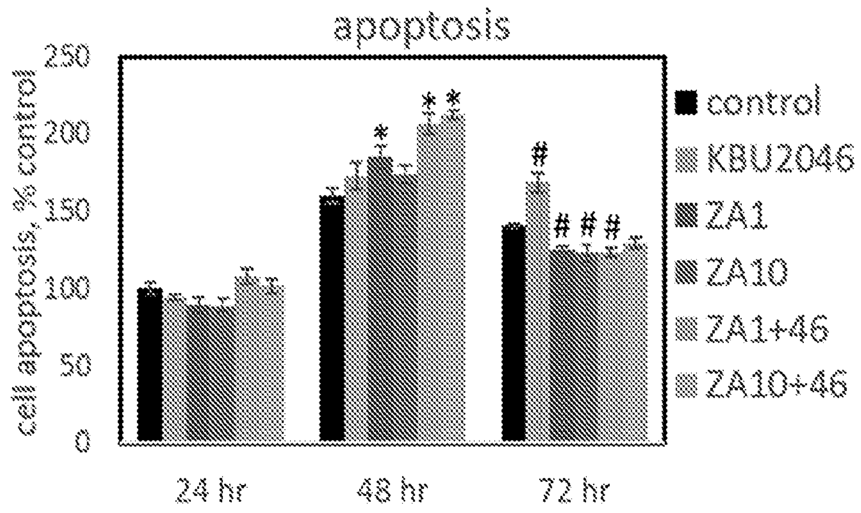

FIGS. 5C-5E graphs cell viability, cytotoxicity and apoptosis, as measured by a Triplex Assay, when RAW 267.4 cells were treated with KBU2046, zoledronic acid, or the combination.

Figure 5F:
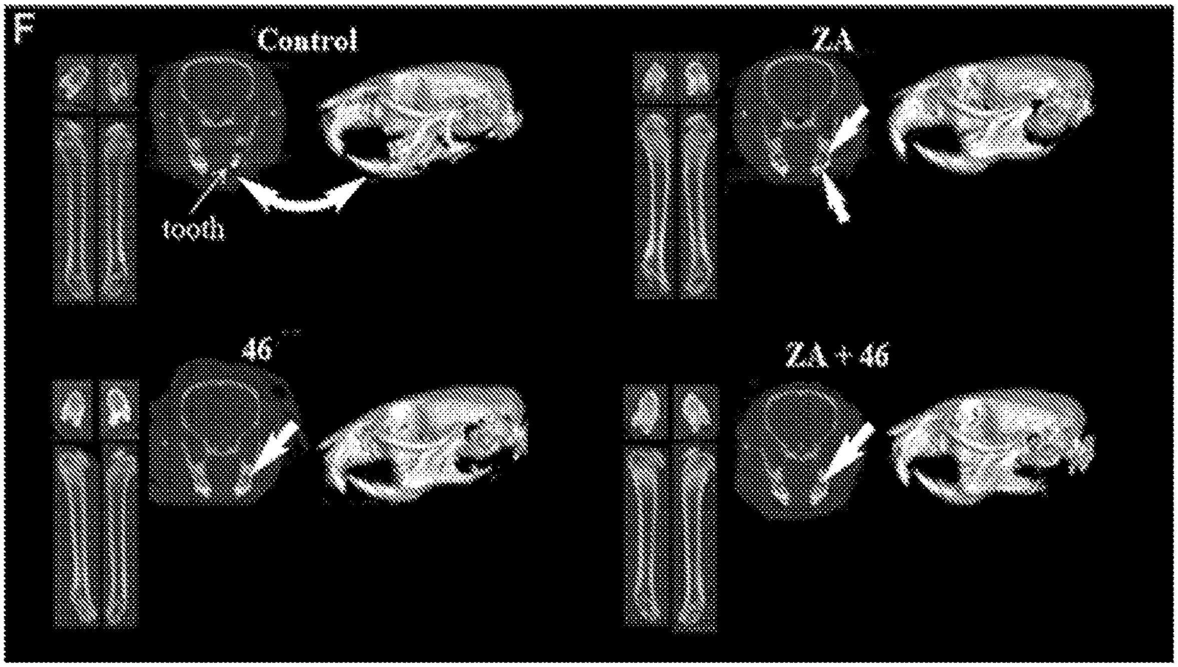

FIG. 5F depicts effects on bone degradation, measured by computed tomography, after intra-cardiac injection of human PC3 prostate cancer cells when mice were treated with KBU2046, zoledronic acid, or the combination.

Figure 5G:
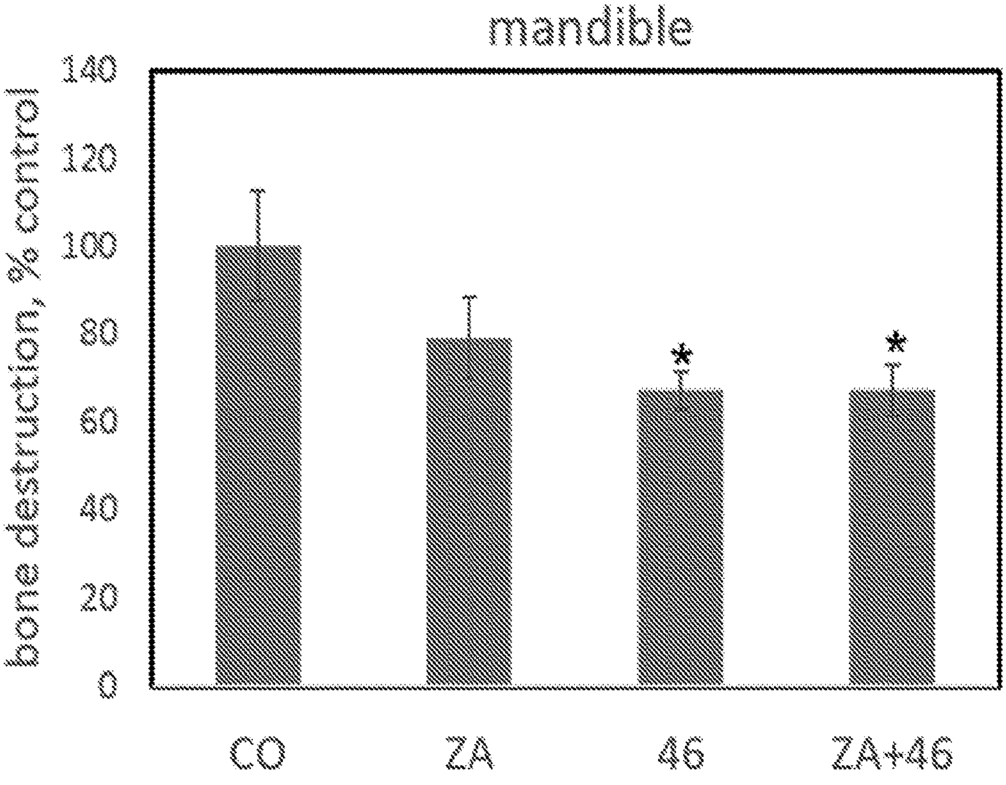
Figure 5H:
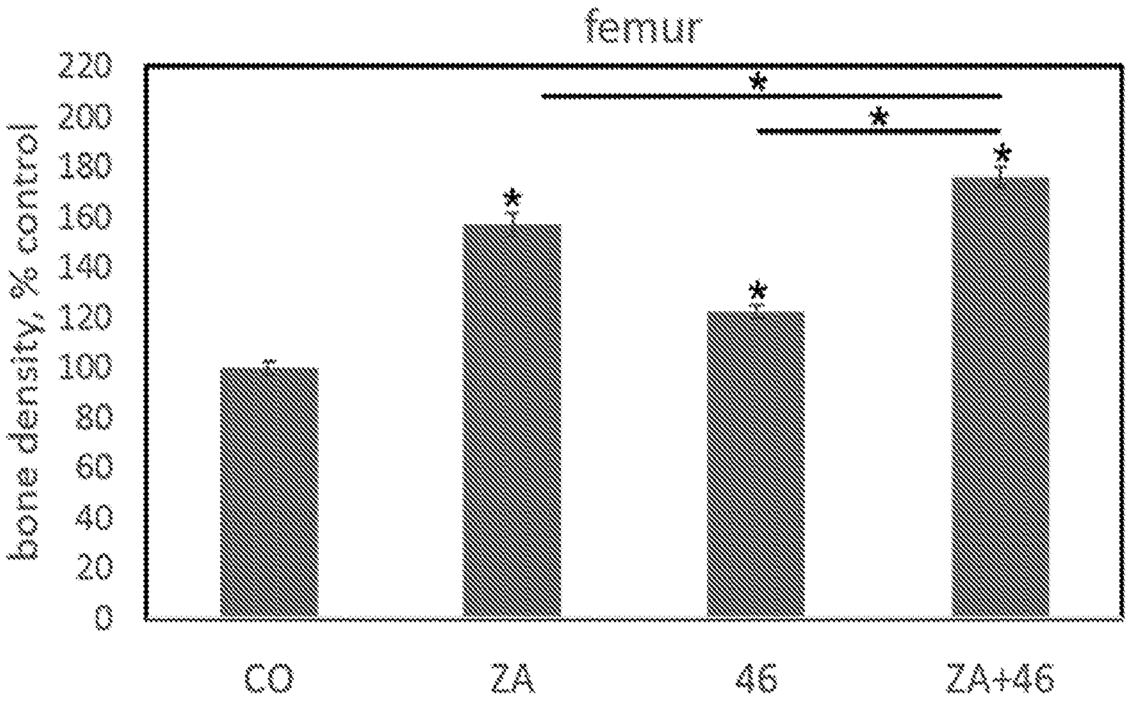

FIGS. 5G-5H graphs effects on bone degradation in the mandible and femur, quantified by computed tomography, after intra-cardiac injection of human PC3 prostate cancer cells when mice were treated with KBU2046, zoledronic acid, or the combination.

Figure 6A:
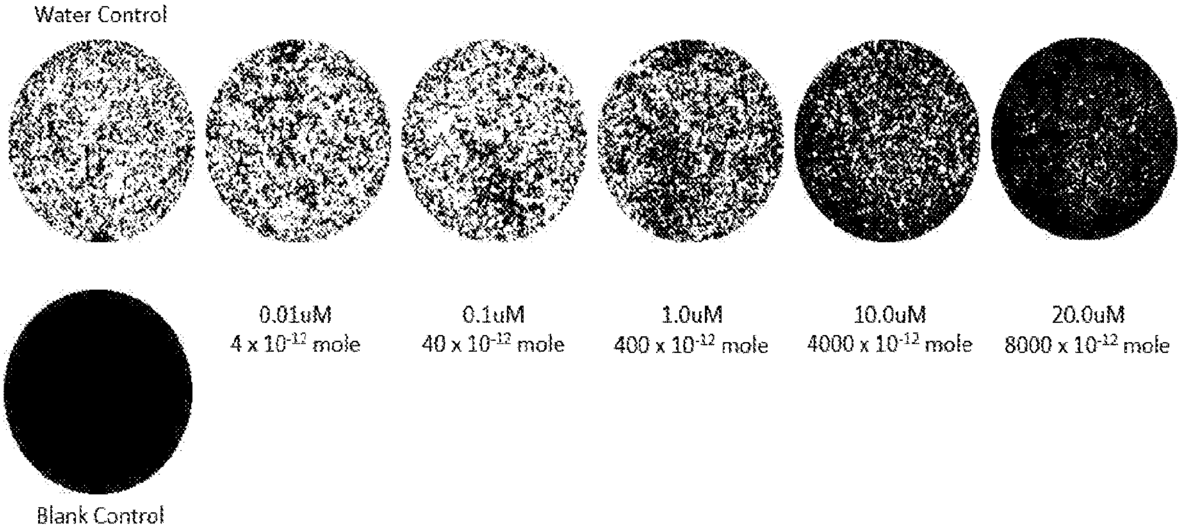
Figure 6B:
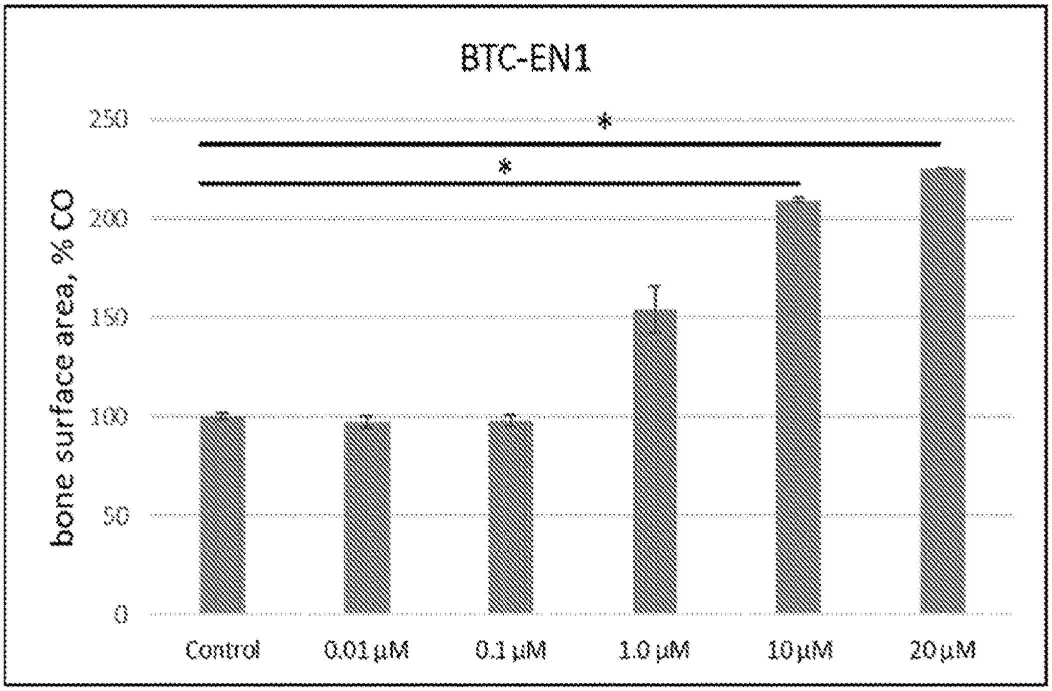

FIGS. 6A and 6B represent the effect of compound E ($n_1$=1) herein in inhibiting osteoclast-mediated bone degradation.

Figure 6C:
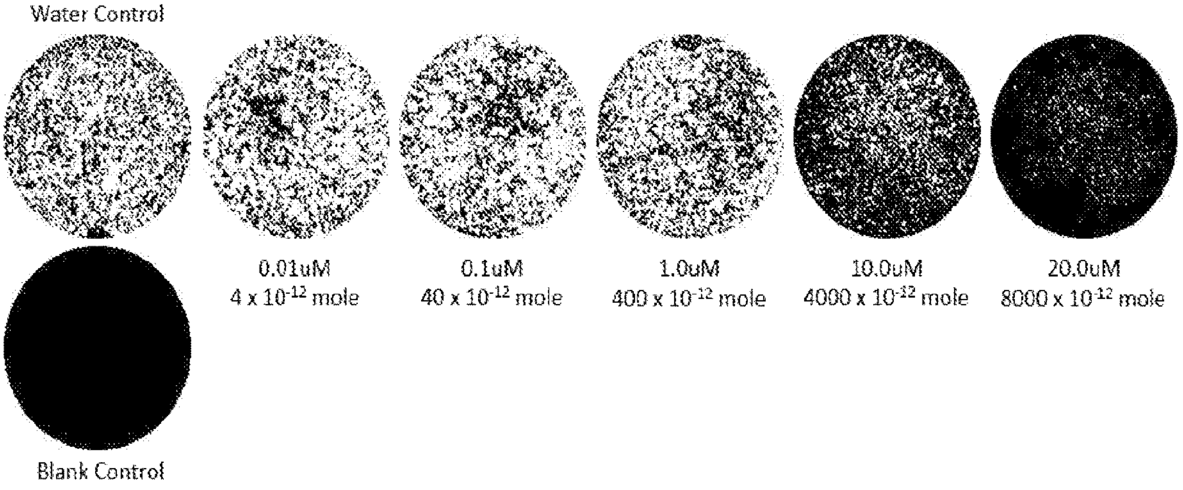
Figure 6D:
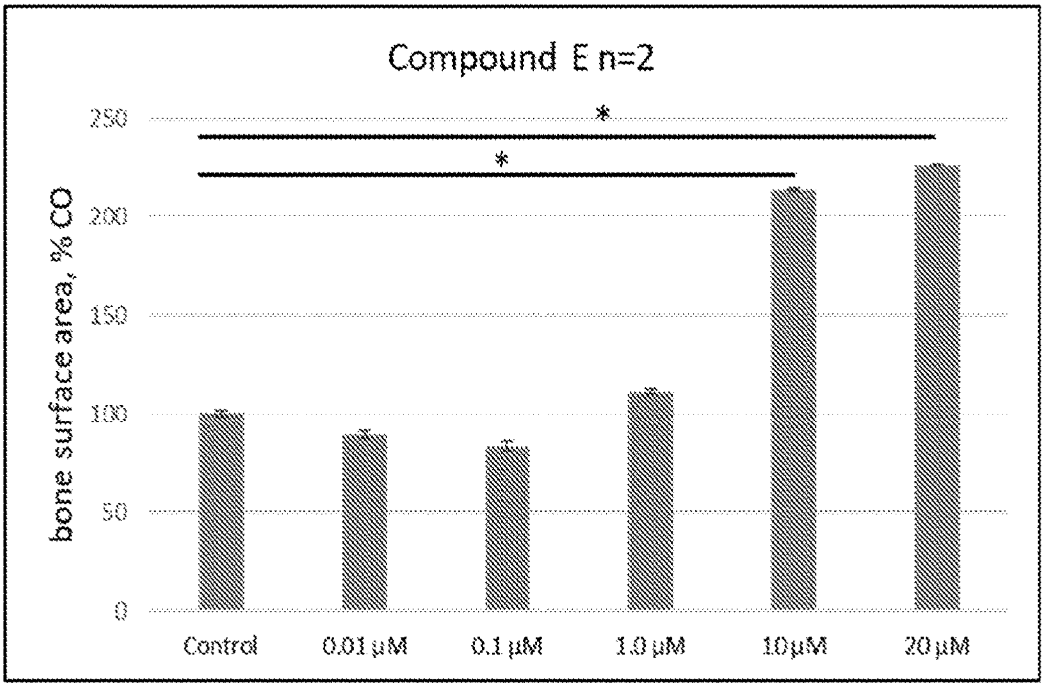

FIGS. 6C and 6D represent the effect of compound E ($n_1$=2) herein in inhibiting osteoclast-mediated bone degradation.

Figure 6E:
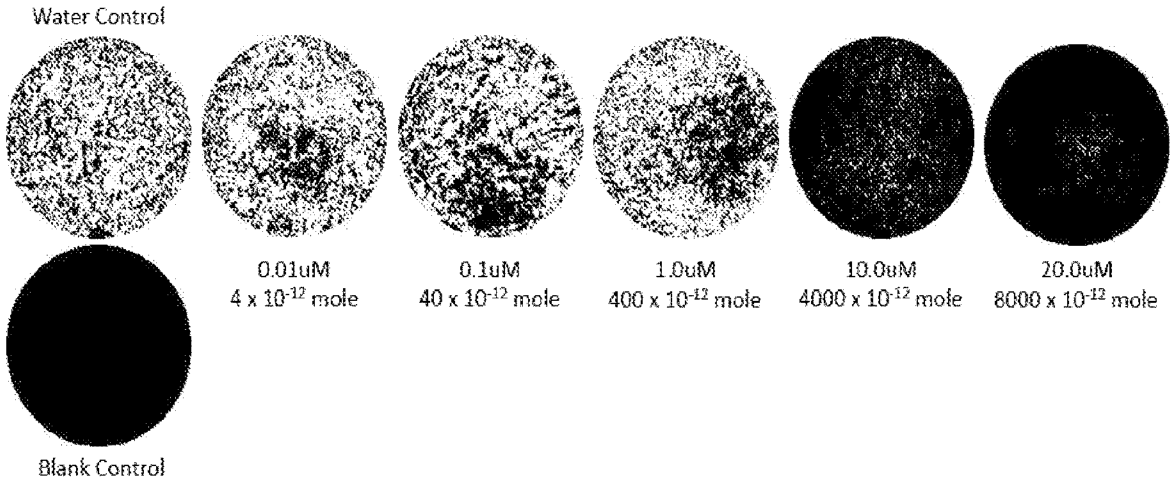
Figure 6F:
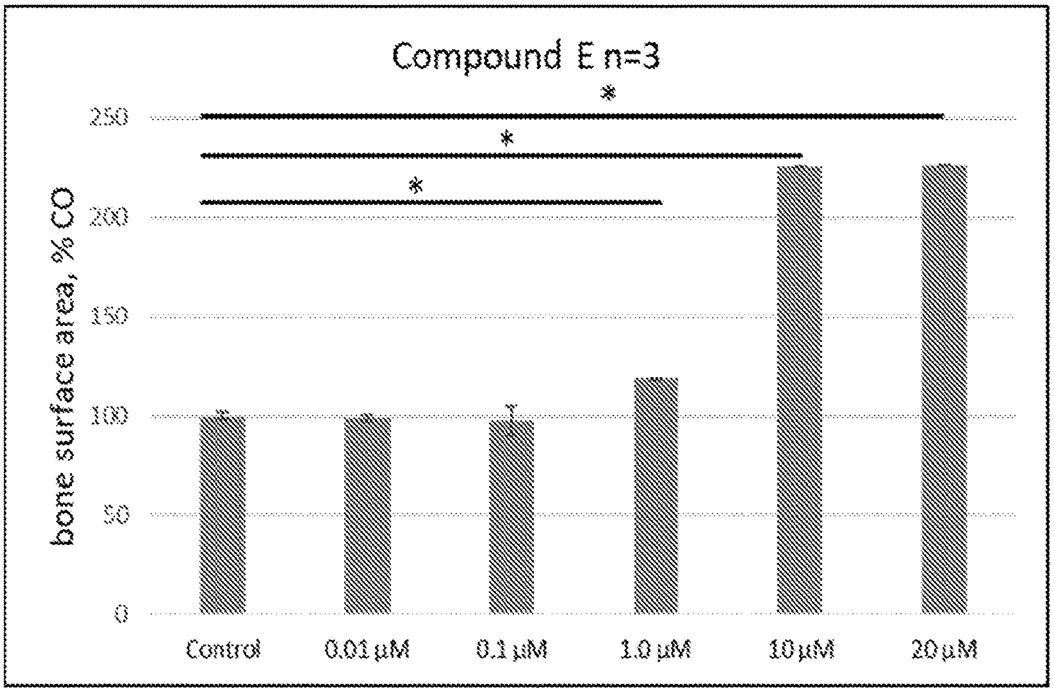

FIGS. 6E and 6F represent the effect of compound E ($n_1$=3) herein in inhibiting osteoclast-mediated bone degradation.

Figure 6G:
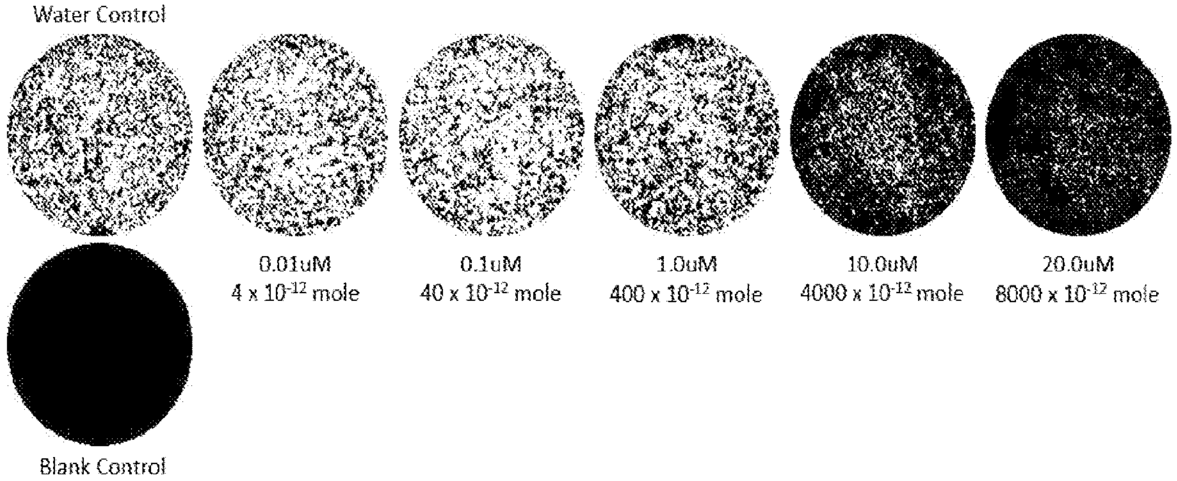
Figure 6H:
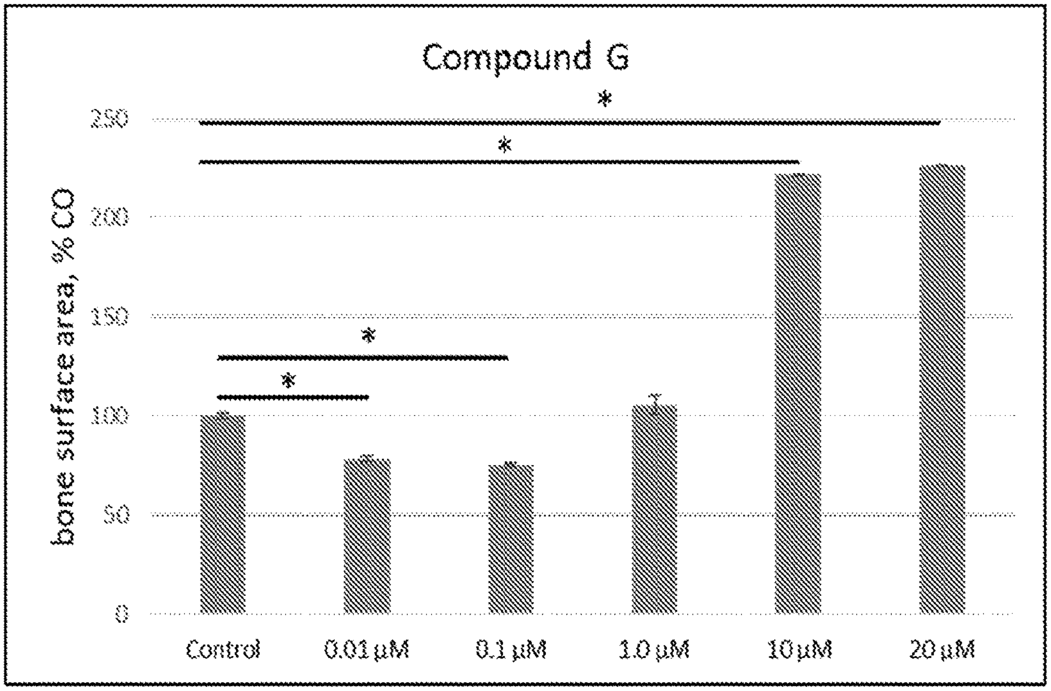
Figure 6I:
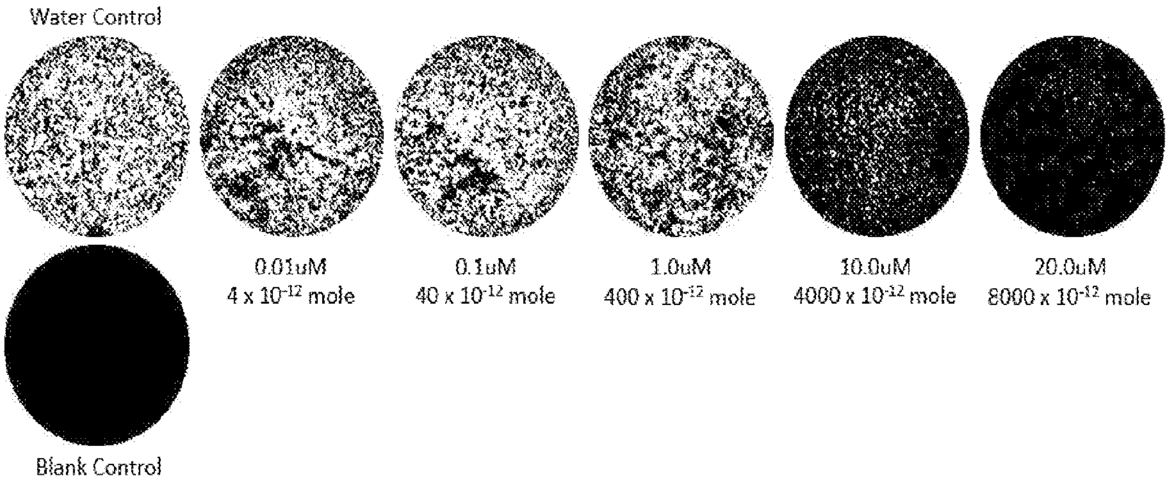

FIGS. 6G and 6H represent the effect of compound G herein in inhibiting osteoclast-mediated bone degradation.

Figure 6J:
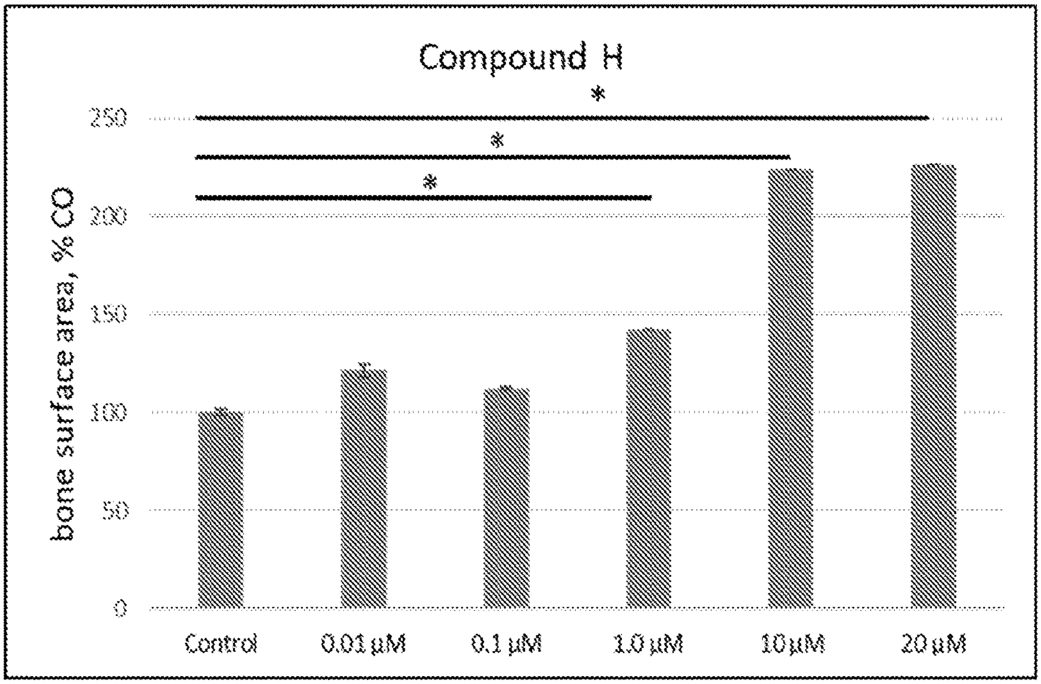

FIGS. 61 and 6J represent the effect of compound H herein in inhibiting osteoclast-mediated bone degradation.

Figure 6K:
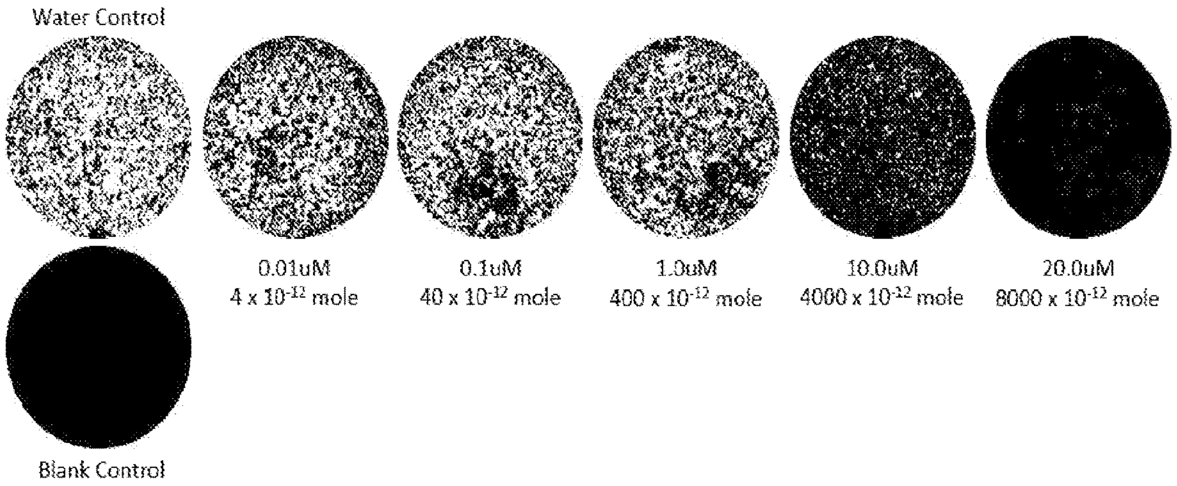
Figure 6L:
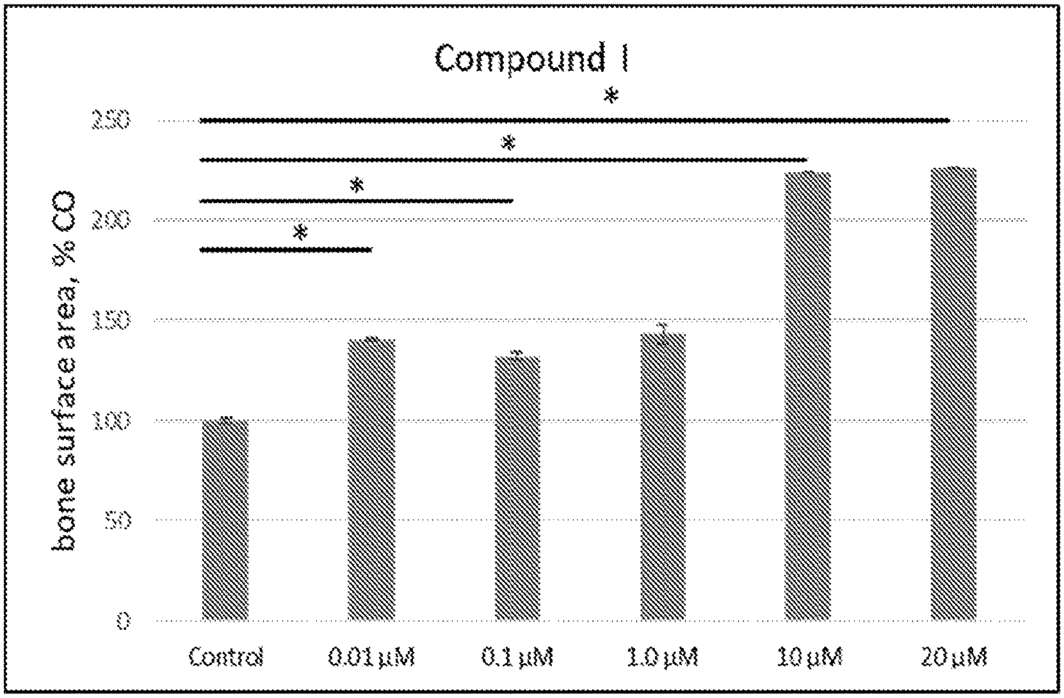

FIGS. 6K and 6L represent the effect of compound I herein in inhibiting osteoclast-mediated bone degradation.

Figure 7:
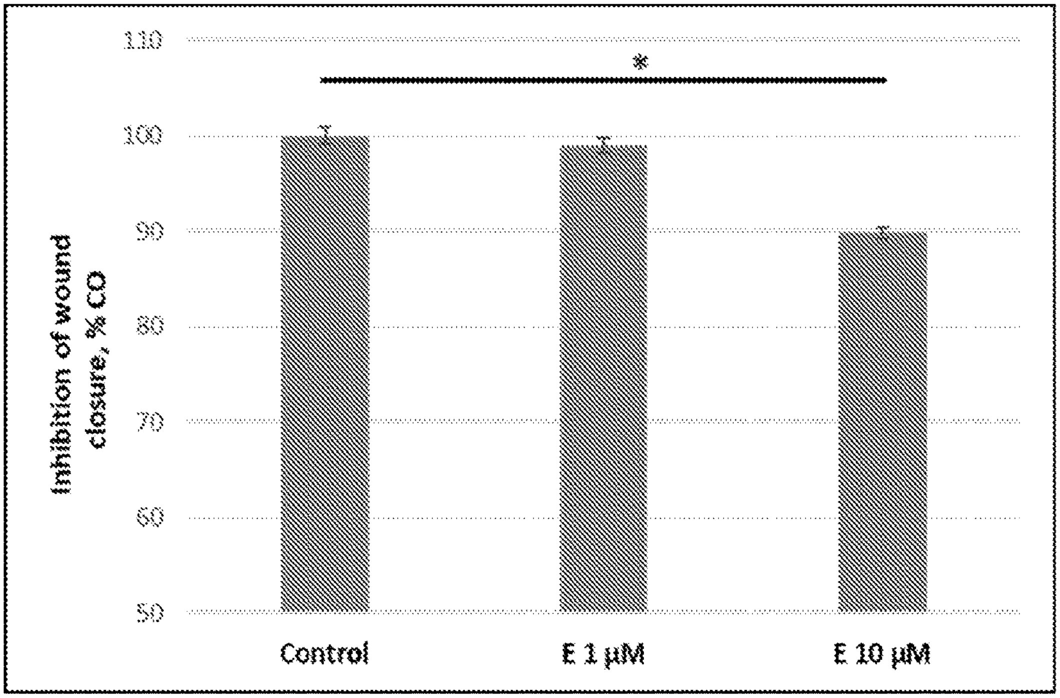

FIG. 7 represents the effects of experimental compound in the inhibition of PCa cell motility.

Figure 8A:
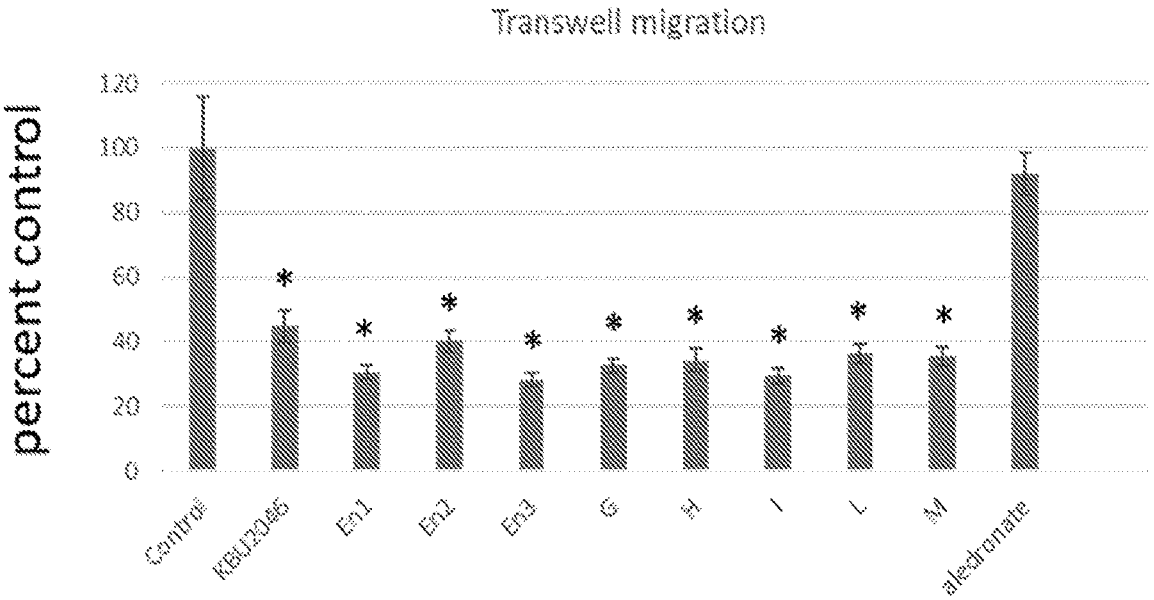
Figure 8B:
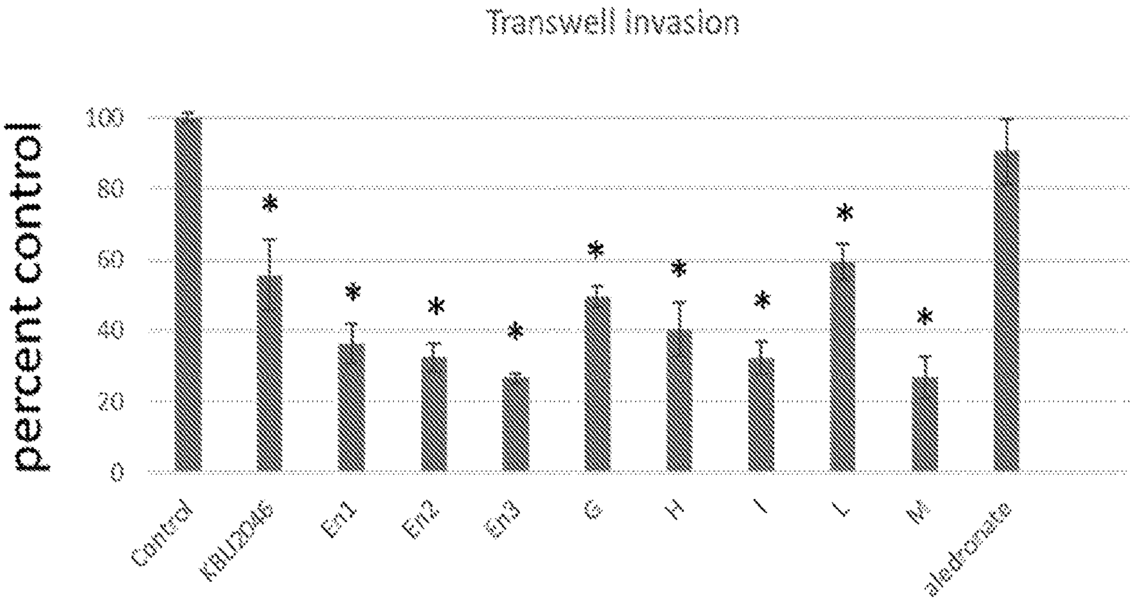

FIGS. 8A and 8B represent transwell migration and transwell invasion of PC3 cells treated with 10 micromolar Compound E (n=1).

Figure 9:
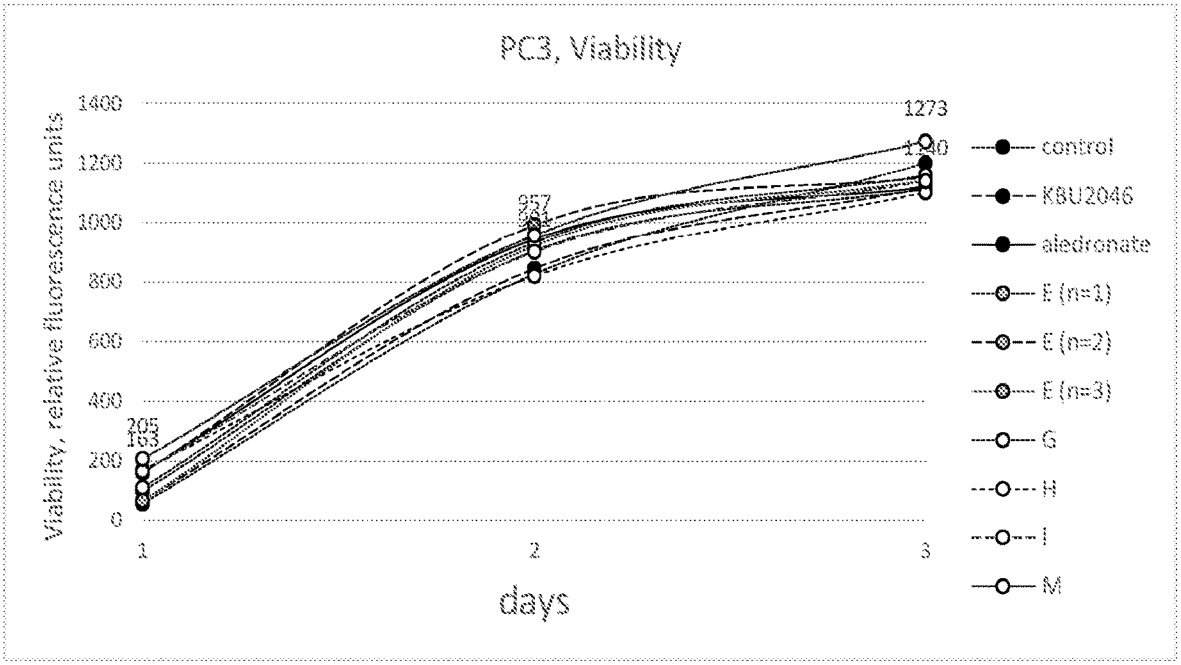

FIG. 9 represents PC3 cell viability under exponential growth and one day later following 10 micromolar treatment of Compound E (n=1).

Figure 10:
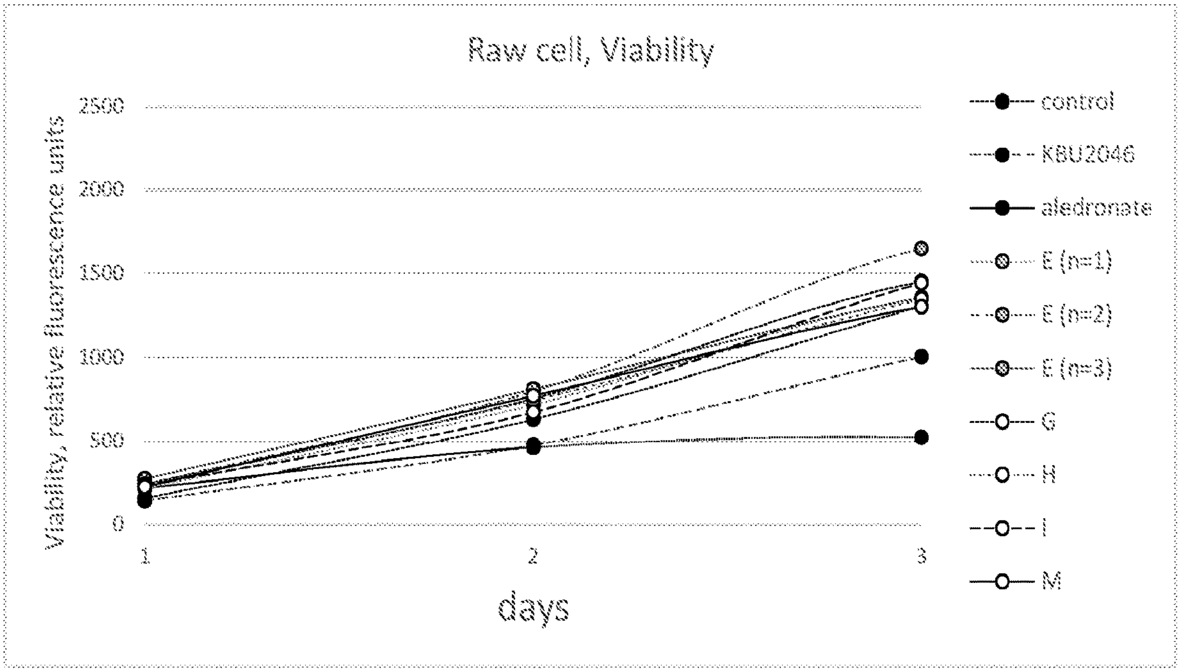

FIG. 10 represents raw 267.4 cells under exponential growth and treated with RANKL and micromolar treatment of Compound E (n=1).

Figure 11A:
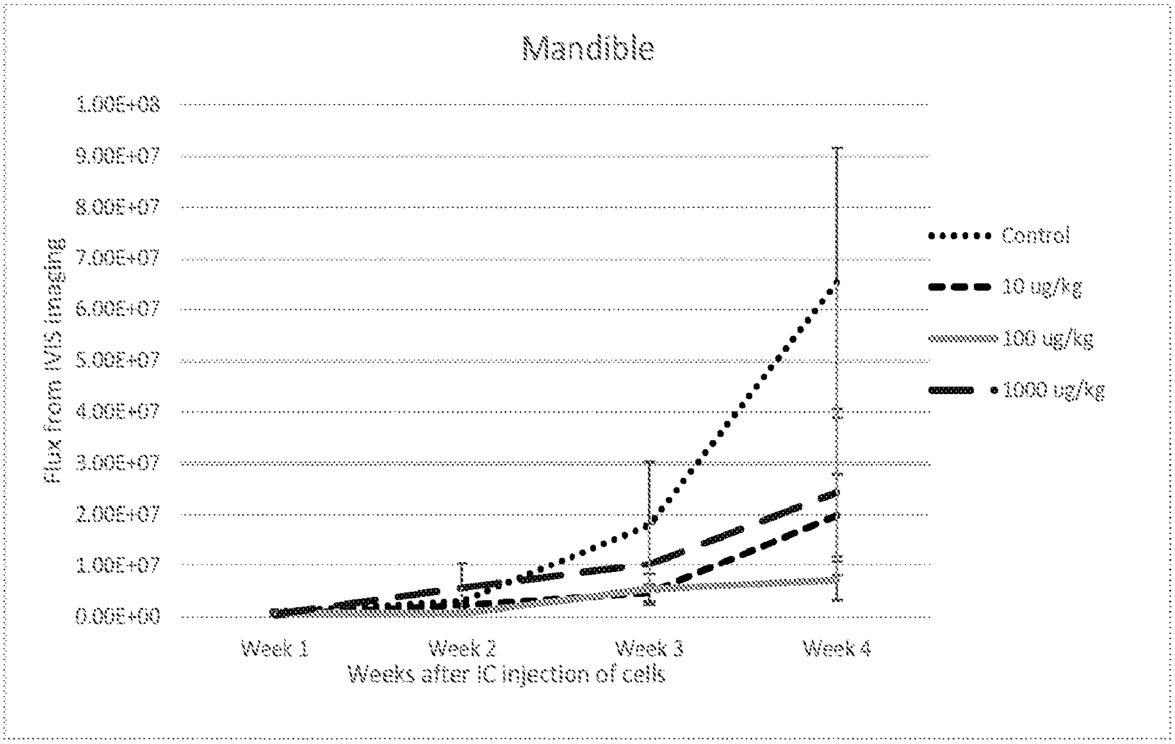
Figure 11B:
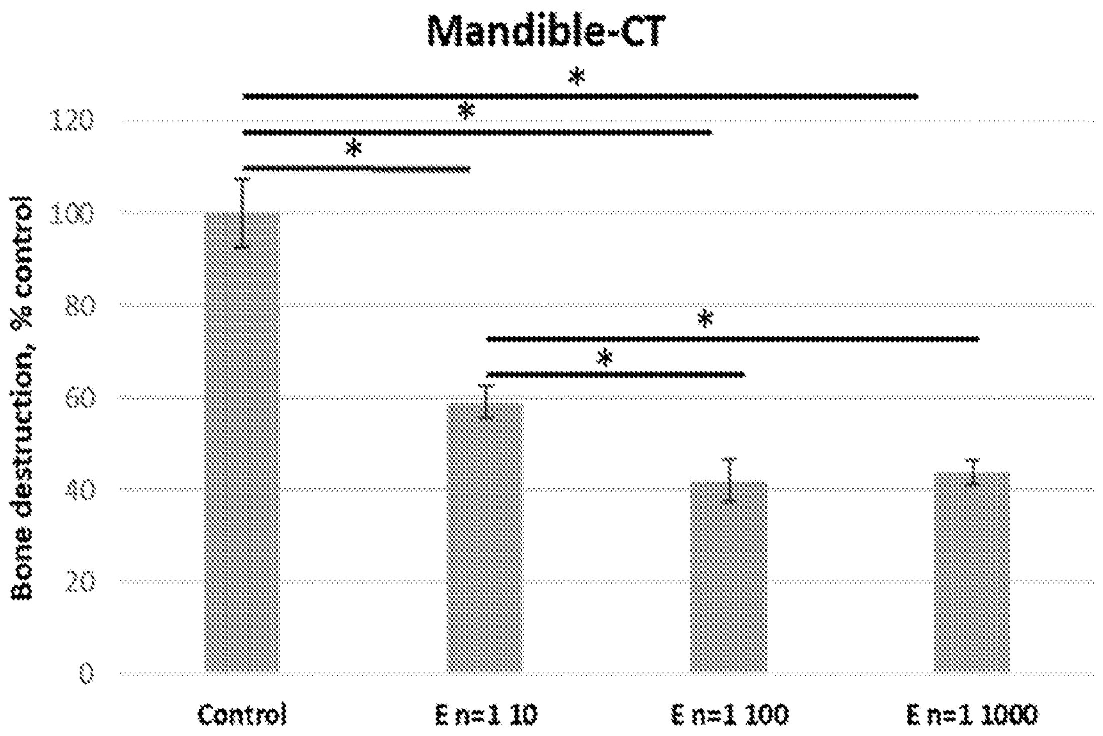

FIGS. 11A and 11B represent degrees of mice jaw bone destruction quantified following treatment with compound E (n=1).

Figure 12:
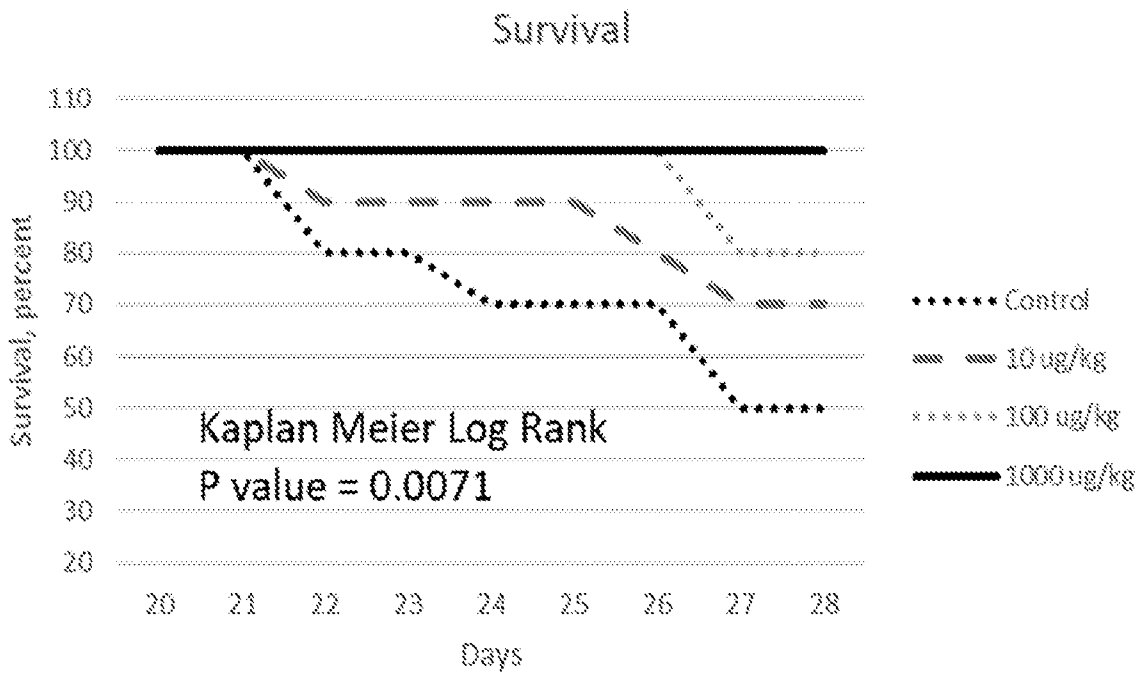

FIG. 12 represents survival of mice following treatment with compound E (n=1) 1 week prior to cardiac injection with PC3-luc cells.

Figure 13:
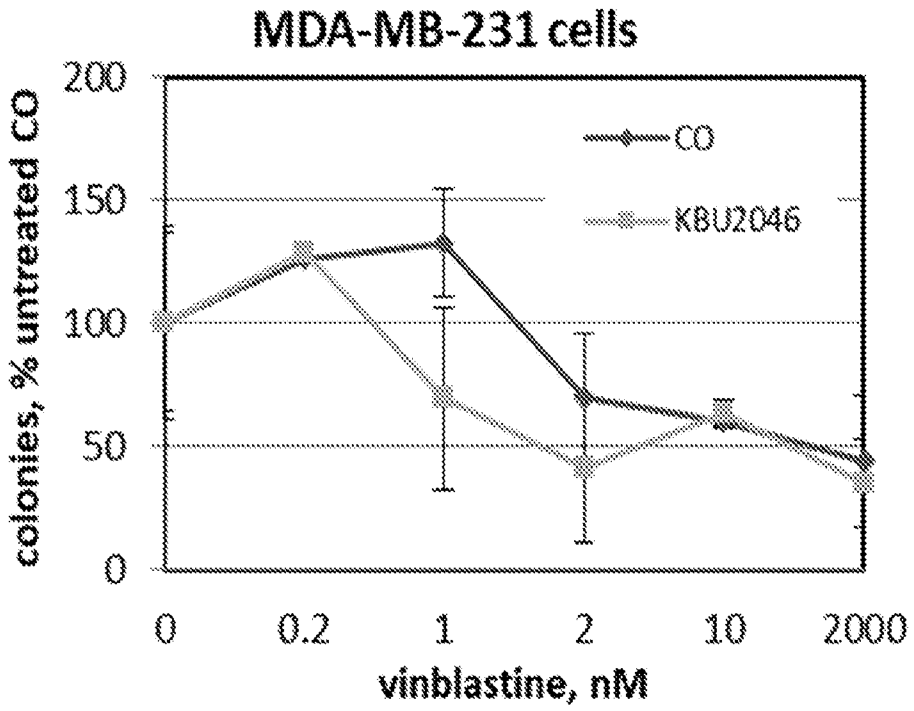

FIG. 13 represents KBU2046 does not inhibit activity of adriamycin in MDA-MB-231 cells.

Figure 14:
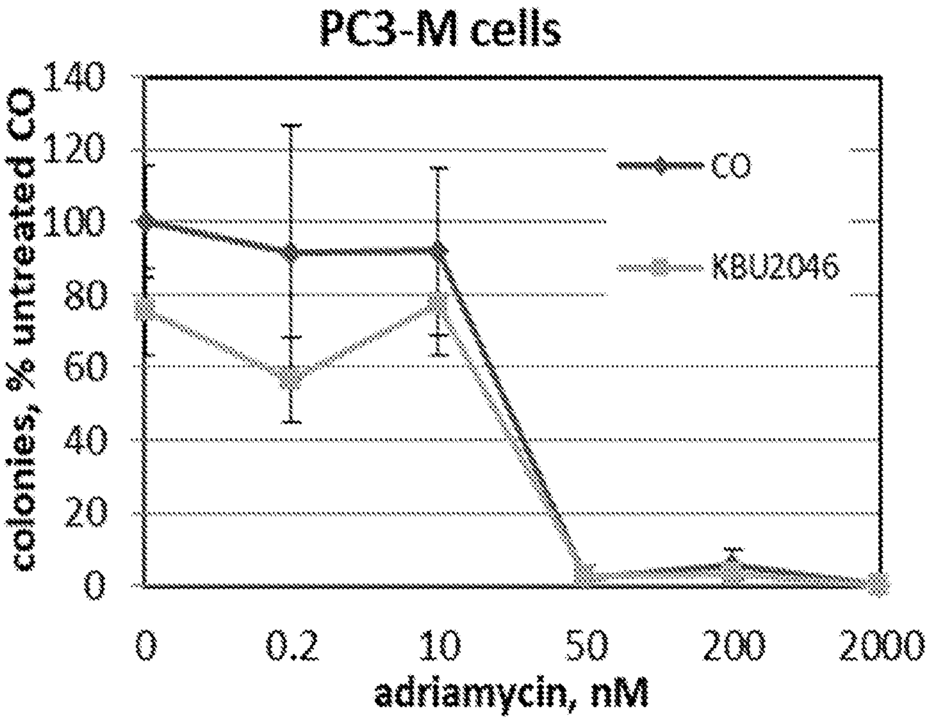

FIG. 14 represents KBU2046 does not inhibit activity of adriamycin in PC3-M cells.

Figure 15:
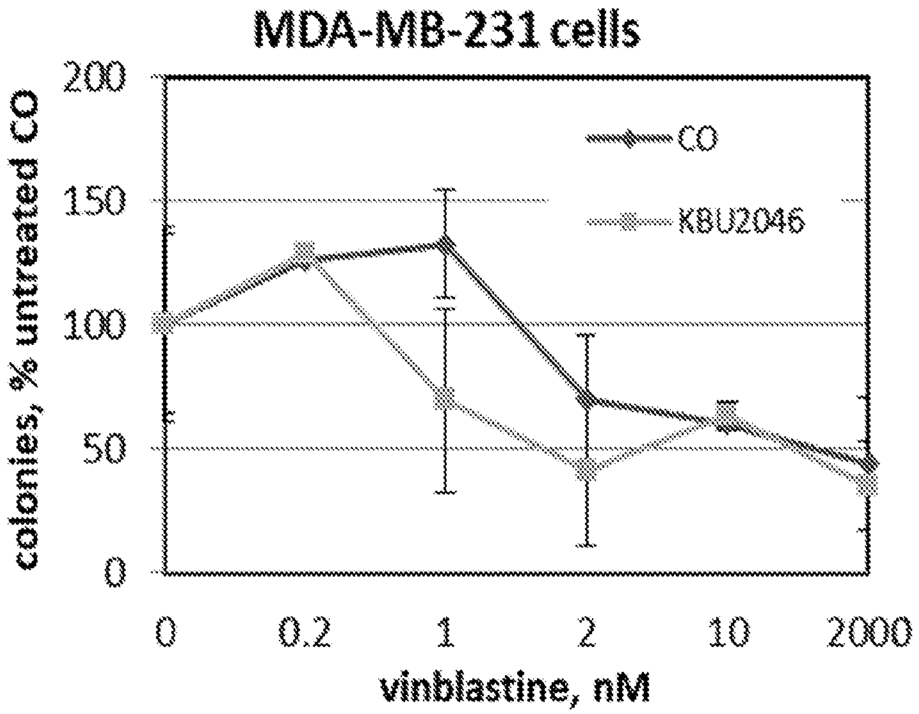

FIG. 15 represents KBU2046 does not inhibit activity of vinblastine in MDA-MB-231 cells.

Figure 16:
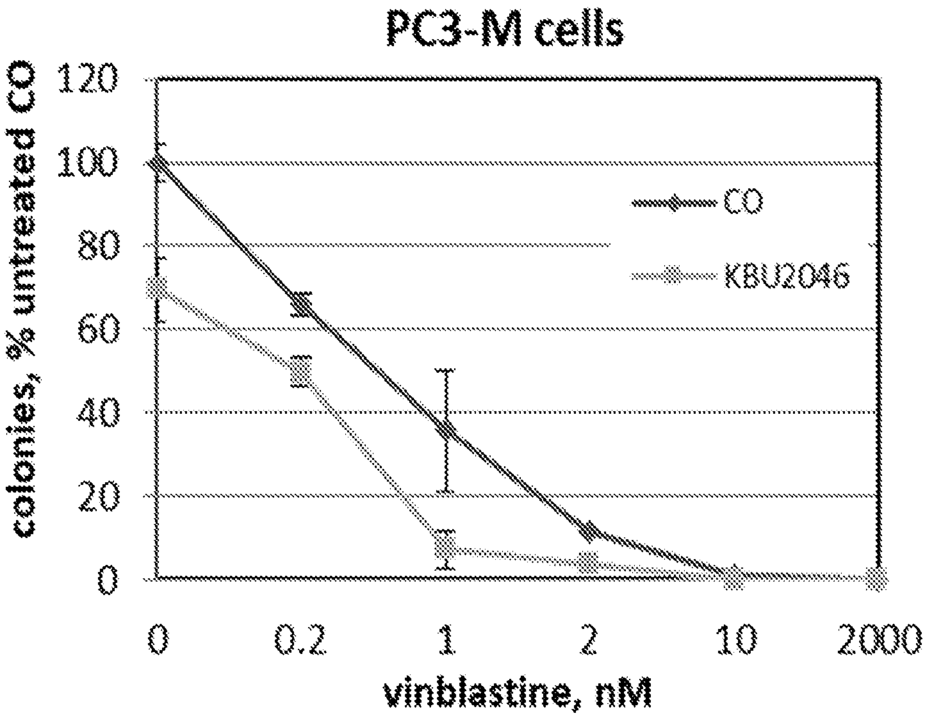

FIG. 16 represents KBU2046 does not inhibit activity of vinblastine in PC3-M cells.

Figure 17:
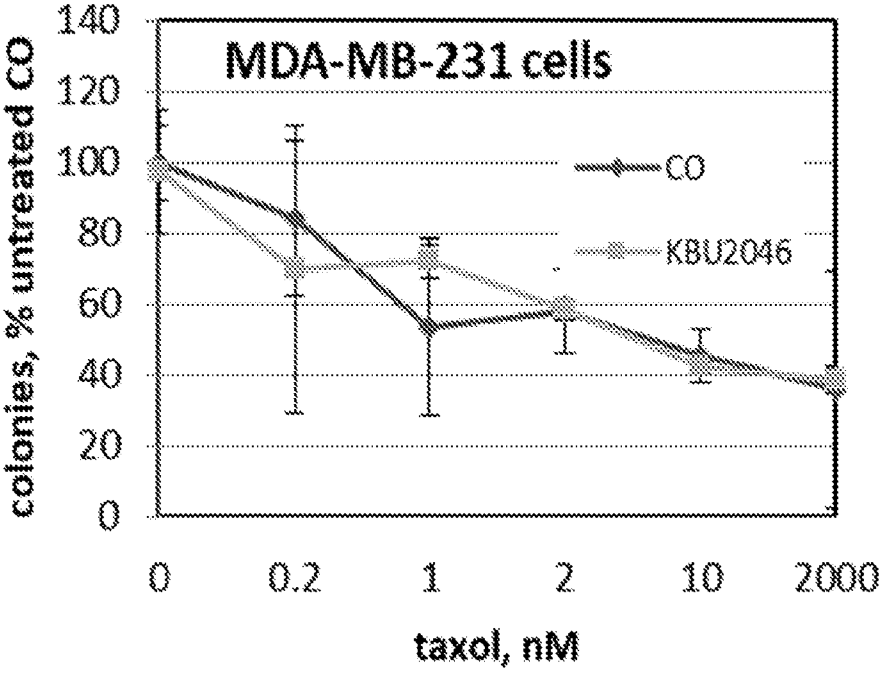

FIG. 17 represents KBU2046 does not inhibit activity of taxol in MDA-MB-231 cells.

Figure 18:
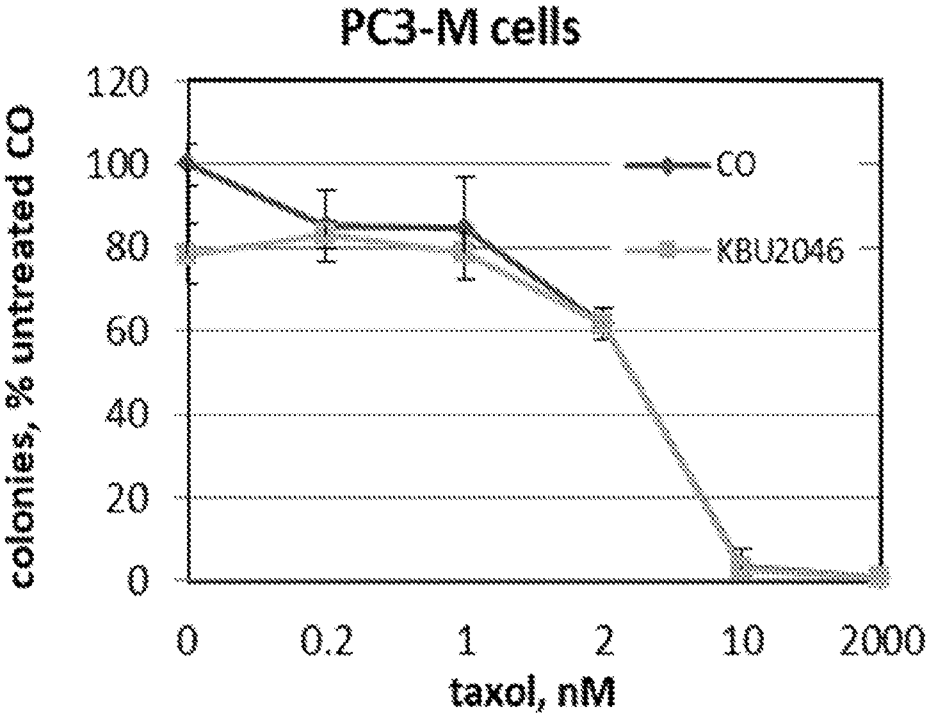

FIG. 18 represents KBU2046 does not inhibit activity of taxol in PC3-M cells.

DETAILED DESCRIPTION OF THE INVENTION

The following description sets forth exemplary methods, parameters and the like. It should be recognized, however, that such description is not intended as a limitation on the scope of the present disclosure but is instead provided as a description of exemplary embodiments.

Also provided is a compound of Formula (Ia):

(Ia)

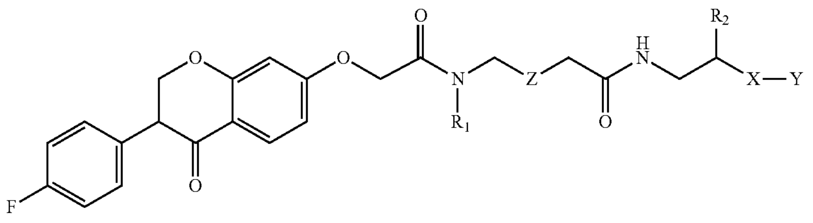

wherein, $R_1$, $R_2$, $n_1$, X, Y, and Z are as defined for Formula (I), above, or a pharmaceutically acceptable salt, co-crystal, polymorph, solvate, hydrate, or enantiomer thereof.

Also provided is a compound of Formula (Ib):

(Ib)

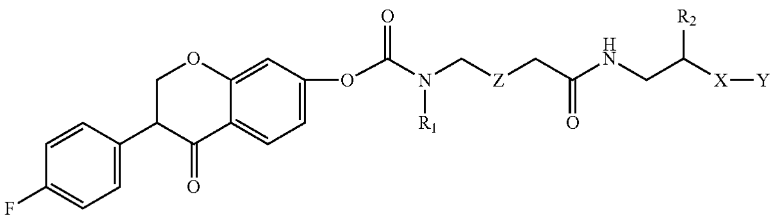

wherein, $R_1$, $R_2$, $n_1$, X, Y, and Z are as defined for Formula (I), above, or a pharmaceutically acceptable salt, co-crystal, polymorph, solvate, hydrate, or enantiomer thereof.

Also provided is a compound of Formula (Ic):

(Ic)

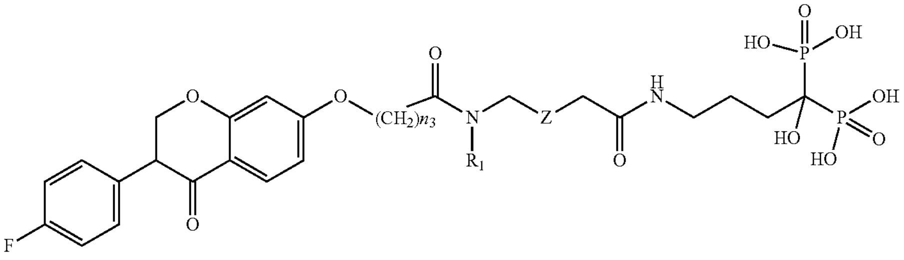

wherein, $R_1$, $R_2$, $n_1$, $n_3$, X, Y, and Z are as defined for Formula (I), above, or a pharmaceutically acceptable salt, co-crystal, polymorph, solvate, hydrate, or enantiomer thereof.

Another embodiment provides a compound of Formula (Ic), wherein $R_1$ is selected from the group of H and methyl; and $n_1$ is an integer selected from the group of 1, 2, and 3; n3 is an integer selected from the group of 1 and 2; and Z is selected from the group of:

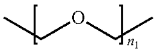 and 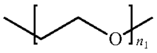 ;

or a pharmaceutically acceptable salt, co-crystal, polymorph, solvate, hydrate, or enantiomer thereof.

Within each of the embodiments above for a compound of Formula (Ic), or a pharmaceutically acceptable salt, co-crystal, polymorph, solvate, hydrate, or enantiomer thereof, there is a further embodiment wherein $n_3$ is 0 and $R_1$ is hydrogen.

Within each of the embodiments above for a compound of Formula (Ic), or a pharmaceutically acceptable salt, co-crystal, polymorph, solvate, hydrate, or enantiomer thereof, there is a further embodiment wherein $n_3$ is 0 and $R_1$ is methyl.

Within each of the embodiments above for a compound of Formula (Ic), or a pharmaceutically acceptable salt, co-crystal, polymorph, solvate, hydrate, or enantiomer thereof, there is a further embodiment wherein Z is:

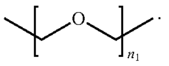

Within each of the embodiments above for a compound of Formula (Ic), or a pharmaceutically acceptable salt, co-crystal, polymorph, solvate, hydrate, or enantiomer thereof, there is a further embodiment wherein Z is:

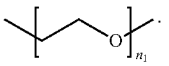

Within each of the embodiments above for a compound of Formula (Ic), or a pharmaceutically acceptable salt, co-crystal, polymorph, solvate, hydrate, or enantiomer thereof, there is a further embodiment wherein n3 is 0.

Within each of the embodiments above for a compound of Formula (Ic), or a pharmaceutically acceptable salt, co-crystal, polymorph, solvate, hydrate, or enantiomer thereof, there is a further embodiment wherein n3 is 1.

Provided is a compound of Formula (Id):

(Id)

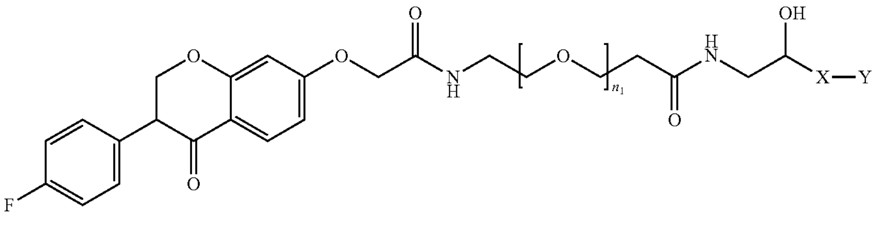

wherein:

$n_1$ is an integer selected from the group of 1, 2, 3, 4, 5, and 6;

X is $(-CH_2-)_{n2}$;

$n_2$ is an integer selected from 0, 1, 2, and 3; and

Y is a bisphosphonate compound;

or a pharmaceutically acceptable salt, co-crystal, polymorph, solvate, hydrate, or enantiomer thereof.

A further embodiment provides a compound of Formula (Id), above, or a pharmaceutically acceptable salt, co-crystal, polymorph, solvate, hydrate, or enantiomer thereof, wherein $n_1$ is an integer selected from the group of 1, 2, 3, 4, and 5; and n2, X, and Y are as defined for Formula (Id), above.

A still further embodiment provides a compound of Formula (Id), above, or a pharmaceutically acceptable salt, co-crystal, polymorph, solvate, hydrate, or enantiomer thereof, wherein $n_1$ is an integer selected from the group of 1, 2, 3, and 4; and n2, X, and Y are as defined for Formula (Id), above.

Also provided is a compound of Formula (II), or a pharmaceutically acceptable salt thereof:

(II)

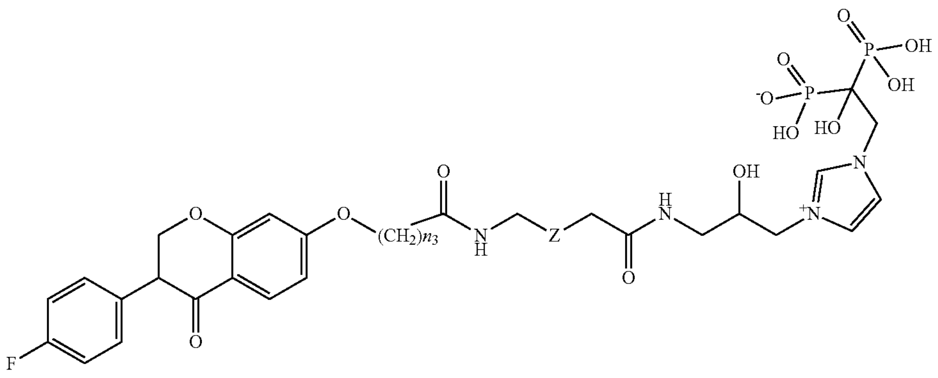

wherein:

Z is selected from the group of;

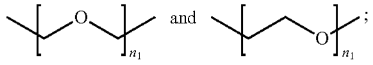

$n_1$ is an integer selected from the group of 1, 2, 3, 4, 5, and 6; and $n_3$ is an integer selected from the group of 0 and 1;

or a pharmaceutically acceptable salt, co-crystal, polymorph, solvate, hydrate, or enantiomer thereof.

A further embodiment provides a compound of Formula (II), above, or a pharmaceutically acceptable salt, co-crystal, polymorph, solvate, hydrate, or enantiomer thereof, wherein $n_1$ is an integer selected from the group of 1, 2, 3, 4, and 5; and $n_2$ is an integer selected from the group of 0 and 1.

A still further embodiment provides a compound of Formula (II), above, or a pharmaceutically acceptable salt, co-crystal, polymorph, solvate, hydrate, or enantiomer thereof, wherein $n_1$ is an integer selected from the group of 1, 2, 3, and 4; and $n_2$ is an integer selected from the group of 0 and 1.

Also provided is a compound of Formula (IIa), or a pharmaceutically acceptable salt thereof:

(IIa)

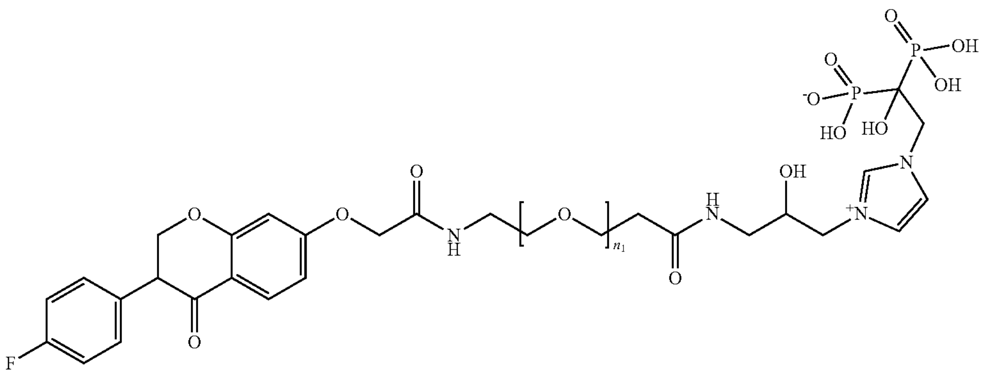

wherein $n_1$ is an integer selected from the group of 1, 2, 3, 4, 5, and 6.

A further embodiment provides a compound of Formula (IIa), or a pharmaceutically acceptable salt, co-crystal, polymorph, solvate, hydrate, or enantiomer thereof, wherein $n_1$ is an integer selected from the group of 1, 2, 3, 4, and 5.

A further embodiment provides a compound of Formula (IIa), or a pharmaceutically acceptable salt, co-crystal, polymorph, solvate, hydrate, or enantiomer thereof, wherein $n_1$ is an integer selected from the group of 1, 2, 3, and 4.

Specific examples of compounds of Formula (II) include:

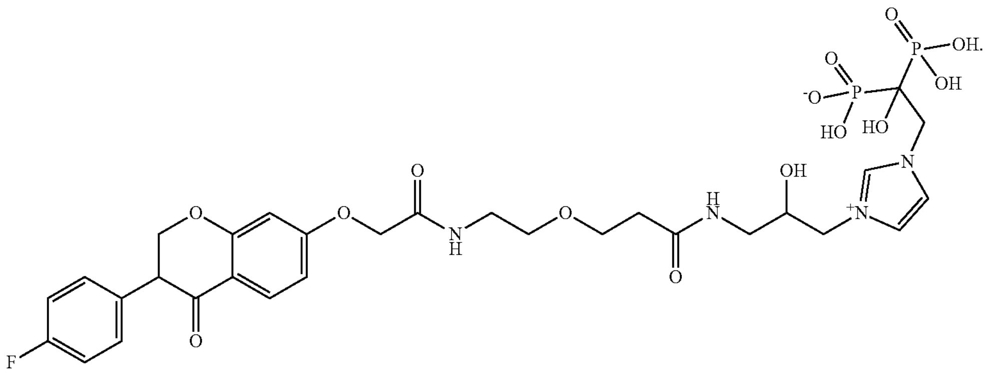

Compound G: (2-(3-(3-(3-(2-(2-((3-(4-fluorophenyl)-4-oxochroman-7-yl)oxy)acetamido)ethoxy) propanamido)-2-(11-oxidaneyl)propyl)-1H-3l4-imidazol-1-yl)-1-hydroxyethane-1,1-diyl)bis(hydrogen phosphonate)

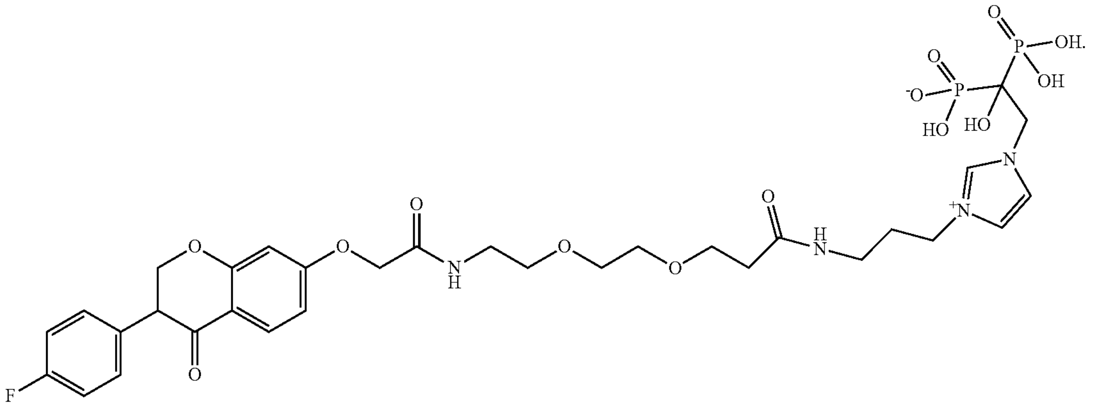

Compound H: (2-(3-(1-((3-(4-fluorophenyl)-4-oxochroman-7-yl)oxy)-15-(11-oxidaneyl)-2,12-dioxo-6,9-dioxa-3,13-diazahexadecan-16-yl)-1H-3l4-imidazol-1-yl)-1-hydroxyethane-1,1-diyl)bis(hydrogen phosphonate)

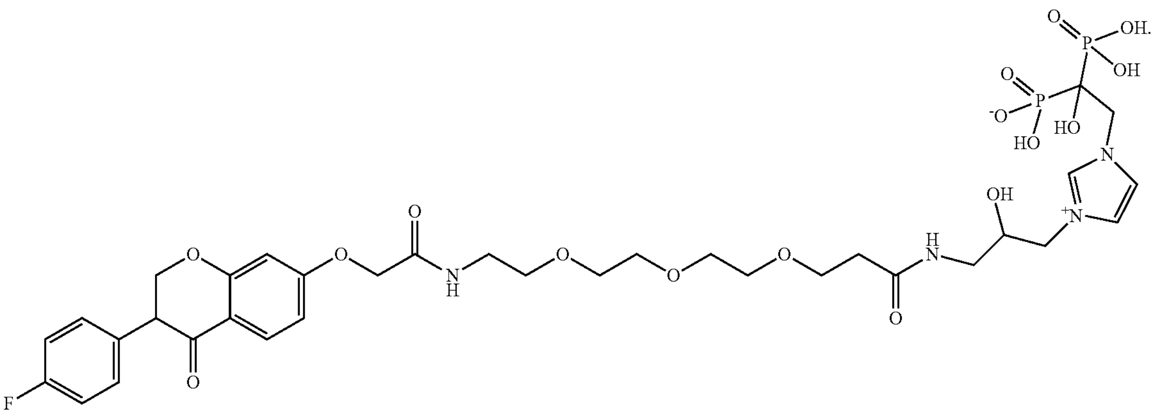

Compound I: (2-(3-(1-((3-(4-fluorophenyl)-4-oxochroman-7-yl)oxy)-18-(11-oxidaneyl)-2,15-dioxo-6,9,12-trioxa-3,16-diazanonadecan-19-yl)-1H-3|4-imidazol-1-yl)-1-hydroxyethane-1,1-diyl)bis(hydrogen phosphonate)

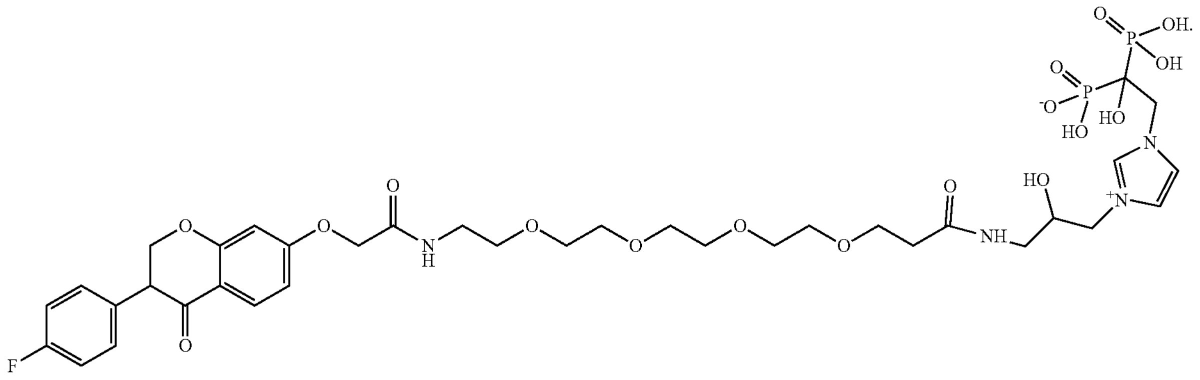

(2-(3-(1-((3-(4-fluorophenyl)-4-oxochroman-7-yl)oxy)-21-(11-oxidaneyl)-2,18-dioxo-6,9,12,15-tetraoxa-3,19-diazadocosan-22-yl)-1H-3|4-imidazol-1-yl)-1-hydroxyethane-1,1-diyl)bis(hydrogen phosphonate).

It is understood in the structures related to compounds of Formula (II), that a positive charge may also be indicated for the 3-position nitrogen in the imidazolyl ring, as follows.

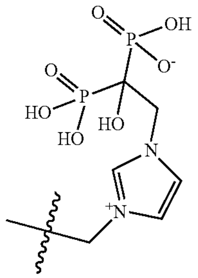 [SMILES: *C[n+]1ccn(CC(O)(P(=O)([O-])O)P(=O)(O)O)c1]

Further provided as separate embodiments are compounds of Formula (III), Formula (IV), Formula (VI), Formula (VII), Formula (VIII), Formula (IX), Formula (X), and Formula (XI), or a pharmaceutically acceptable salt thereof:

(III)

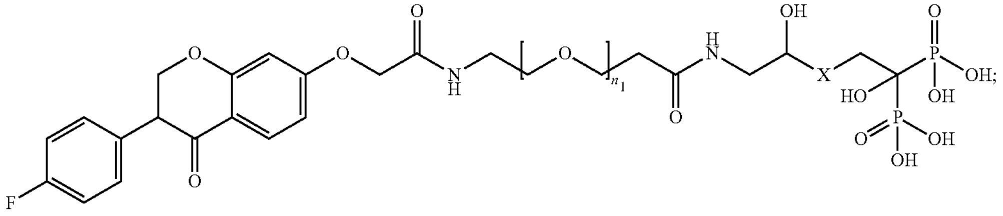

(IV)

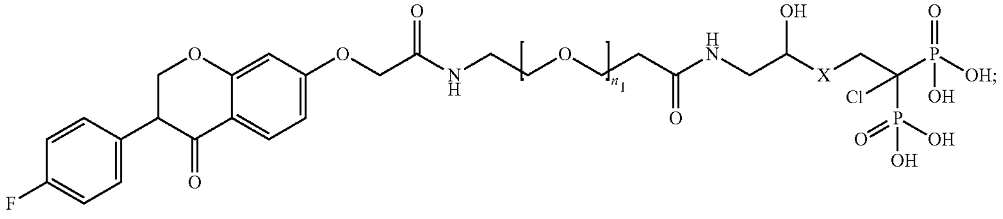

-continued
(V)
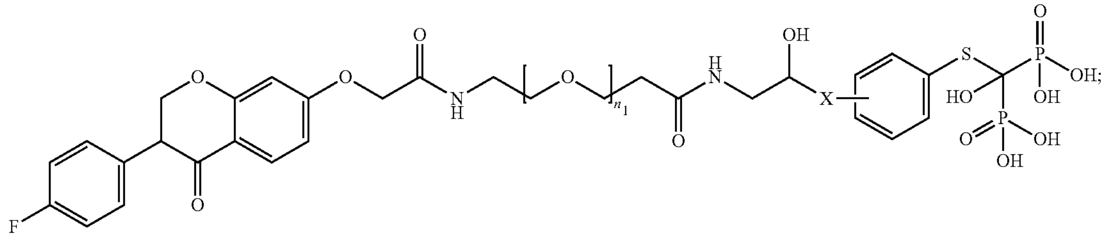
(VI)
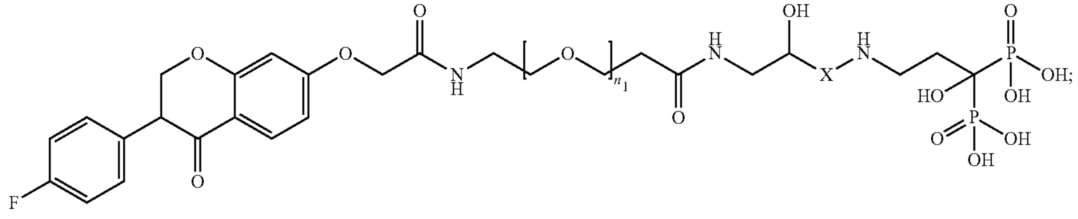
(VII)
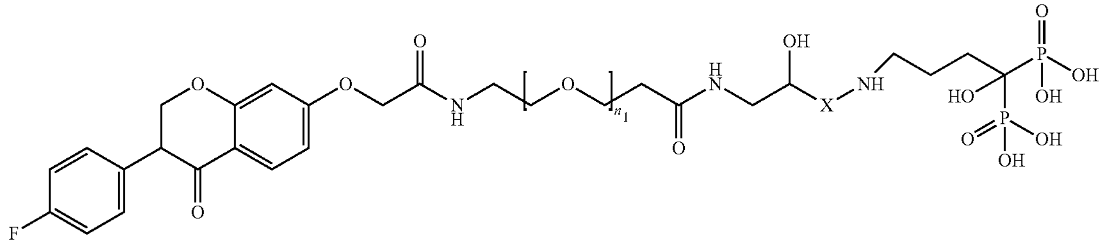
(VIII)
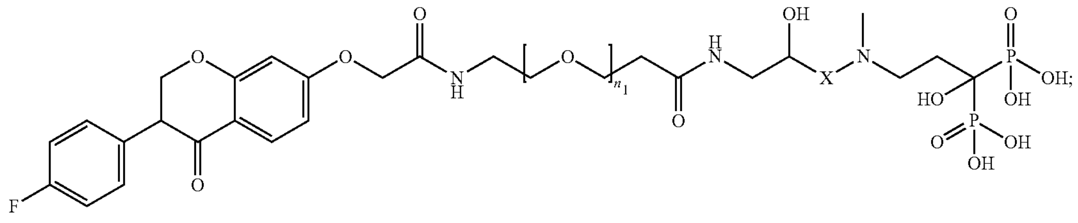
(IX)
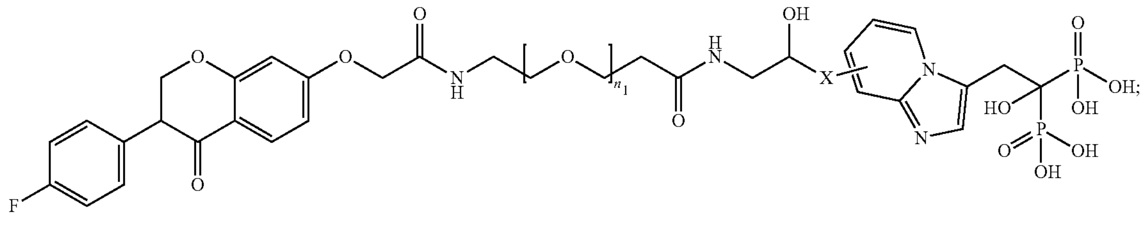
(X)
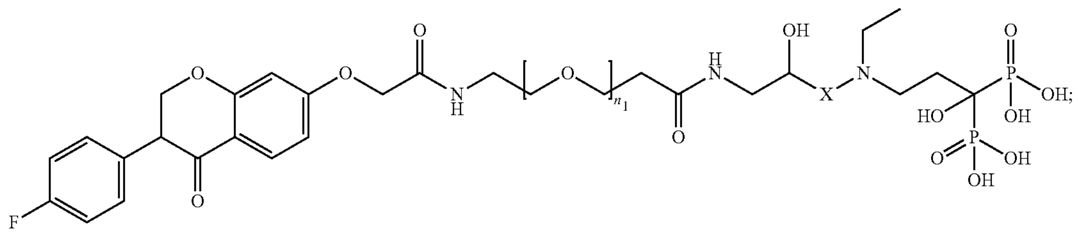
and -continued (XI)

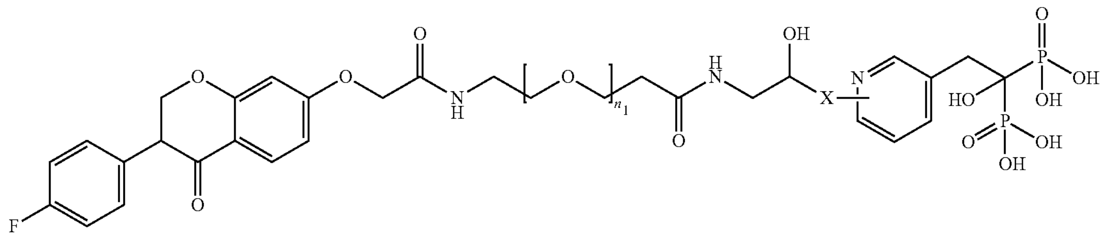

wherein, in each of Formulas (III)-(XI):

$n_1$ is an integer selected from the group of 1, 2, 3, 4, 5, and 6;

X is $(—CH_2—)_{n2}$; and $n_2$ is an integer selected from 0, 1, 2, and 3.

A further embodiment provides a compound of Formula (Id), above, or a pharmaceutically acceptable salt, co-crystal, polymorph, solvate, hydrate, or enantiomer thereof, wherein $n_1$ is an integer selected from the group of 1, 2, 3, 4, and 5; and n2 and X are as defined Formulas (III)-(XI), above.

A further embodiment provides a compound of Formula (Id), above, or a pharmaceutically acceptable salt, co-crystal, polymorph, solvate, hydrate, or enantiomer thereof, wherein $n_1$ is an integer selected from the group of 1, 2, 3, and 4; and n2 and X are as defined Formulas (III)-(XI), above.

Within each of the compound embodiments described herein using Formulas (I), (Ia), (Ib), (Ic), (Id), (II), (III), (IV), (V), (VI), (VII), (VIII), (IX), (X), and (X), there is a separate embodiment in which the integer represented by $n_1$ is 1, 2, or 3. Within each of the compound embodiments described herein using Formulas (I), (Ia), (Ib), (Ic), (Id), (II), (III), (IV), (V), (VI), (VII), (VIII), (IX), (X), and (XI), there is another separate embodiment in which the integer represented by $n_1$ is 1 or 2. Within each of the compound embodiments described herein using Formulas (I), (Ia), (Ib), (Ic), (Id), (II), (III), (IV), (V), (VI), (VII), (VIII), (IX), (X), and (X), there is a separate embodiment in which the integer represented by $n_1$ is 3 or 4.

Within each of the compound embodiments described herein using (I), (Ia), (Ib), (Ic), (Id), (II), (III), (IV), (V), (VI), (VII), (VIII), (IX), (X), and (XI), there is a separate embodiment in which the integer represented by $n_1$ is 1.

Within each of the compound embodiments described herein using Formulas (I), (Ia), (Ib), (Ic), (Id), (II), (III), (IV), (V), (VI), (VII), (VIII), (IX), (X), and (X), there is a separate embodiment in which the integer represented by $n_1$ is 2.

Within each of the compound embodiments described herein using Formulas (I), (Ia), (Ib), (Ic), (Id), (II), (III), (IV), (V), (VI), (VII), (VIII), (IX), (X), and (X), there is a separate embodiment in which the integer represented by $n_1$ is 3.

Within each of the compound embodiments described herein using Formulas (I), (Ia), (Ib), (Ic), (Id), (II), (III), (IV), (V), (VI), (VII), (VIII), (IX), (X), and (X), there is a separate embodiment in which the integer represented by $n_1$ is 4.

Within each of the compound embodiments described herein using Formulas (I), (Ia), (Ib), (Ic), (Id), (II), (III), (IV), (V), (VI), (VII), (VIII), (IX), (X), and (X), there is a separate embodiment in which the integer represented by $n_1$ is 5.

Within each of the compound embodiments described herein using Formulas (I), (Ia), (Ib), (Ic), (Id), (II), (III), (IV), (V), (VI), (VII), (VIII), (IX), (X), and (X), there is a separate embodiment in which the integer represented by $n_1$ is 6.

Within each of the compound embodiments described herein using Formulas (I), (Ia), (Ib), (Ic), (Id), (II), (III), (IV), (V), (VI), (VII), (VIII), (IX), (X), and (XI), there is a separate embodiment in which the integer represented by $n_3$ is 0.

Within each of the compound embodiments described herein using Formulas (I), (Ia), (Ib), (Ic), (Id), (II), (III), (IV), (V), (VI), (VII), (VIII), (IX), (X), and (XI), there is a separate embodiment in which the integer represented by $n_3$ is 1.

It is understood that references herein to Formulas (I)-(XI) include all formulas, including Formulas (I), (Ia), (Ib), (Ic), (Id), (II), (III), (IV), (V), (VI), (VII), (VIII), (IX), (X), and (XI).

Within each of the compound descriptions referenced above for Formulas (I)-(XI), there is a separate embodiment having the same descriptions, otherwise, wherein X is 0. Within each of the compound descriptions referenced above for Formulas (I)-(XI), there is a separate embodiment having the same descriptions, otherwise, wherein X is 1 or 2. Within each of the compound descriptions referenced above for Formulas (I)-(XI), there is a separate embodiment having the same descriptions, otherwise, wherein X is 2 or 3. Within each of the compound descriptions referenced above for Formulas (I)-(XI), there is also a separate embodiment having the same descriptions, otherwise, wherein X is 3 or 4.

Further provided herein is a pharmaceutical composition, the composition comprising a pharmaceutically effective amount of a compound of Formula (I), or a pharmaceutically acceptable salt, co-crystal, polymorph, solvate, hydrate, or enantiomer thereof, and a pharmaceutically acceptable carrier or excipient.

Also provided is a method of treatment of osteoclast mediated bone degradation in a subject, the method comprising administering to a subject in need thereof a pharmaceutically effective amount of a compound of Formula (I), or a pharmaceutically acceptable salt, co-crystal, polymorph, solvate, hydrate, or enantiomer thereof.

Also provided is a method of treatment of cancer of the bone in a subject, the method comprising administering to a subject in need thereof a pharmaceutically effective amount of a compound of Formula (I), or a pharmaceutically acceptable salt, co-crystal, polymorph, solvate, hydrate, or enantiomer thereof.

Also provided is a method of treatment of cancer metastases to the bone in a subject, the method comprising administering to a subject in need thereof a pharmaceutically effective amount of a compound of Formula (I), or a pharmaceutically acceptable salt, co-crystal, polymorph, solvate, hydrate, or enantiomer thereof. Additional methods include those specifically to cancers of the bone that originate as, and are metastatic from, cancers of the breast, prostate, lung, kidney, thyroid, bladder, esophagus, stomach, liver, pancreas, testicles, skin, head and neck, lymphomas, multiple myelomas, and sarcomas from the soft tissue or bone.

Also provided is a method of treatment of cancer of the bone, or a cancer metastasis to the bone, in a subject, the method comprising administering to a subject in need thereof a pharmaceutically effective amount of a compound of Formula (I), or a pharmaceutically acceptable salt, co-crystal, polymorph, solvate, hydrate, or enantiomer thereof, and a second therapeutic agent, such as, but not limited to, a hormone therapeutic agent or a chemotherapeutic agent. In specific, non-limiting embodiments, the hormone therapeutic agent can be an antiestrogen (e.g., tamoxifen, toremifene, fulvestrant, raloxifene, droloxifene, idoxifene and the like), progestogens (e.g., megestrol acetate and the like) aromatase inhibitors (e.g., anastrozole, letrozole, exemestane, vorozole, exemestane, fadrozole, aminoglutethimide, exemestane, 1-methyl-1,4-androstadiene-3,17-dione and the like), anti-androgens (e.g., bicalutimide, nilutamide, flutamide, cyproterone acetate, and the like), luteinizing hormone releasing hormone agonist (LHRH Agonist) (e.g., goserelin, leuprolide, buserelin and the like); 5-.alpha.-reductase inhibitors such as finasteride. In specific, non-limiting embodiments, the cytotoxic chemotherapeutic agent can be (i) alkylating agents, such as procarbazine, ifosphamide, cyclophosphamide, melphalan, chlorambucil, decarbazine, busulfan, thiotepa, (ii) platinum chemotherapy agents, such as cisplatin, carboplatin, oxaliplatin, Eloxatin, (iii) anti-metabolites, such as Methotrexate, 5-fluorouracil (e.g., capecitabine), gemcitabine (2'-deoxy-2',2'-difluorocytidine monohydrochloride (.beta.-isomer), Eli Lilly), 6-mercaptopurine, 6-thioguanine, fludarabine, cladribine, cytarabine, tegafur, raltitrexed, cytosine arabinoside, (iv) anthracyclines, such as daunorubicin, doxorubicin, idarubicin, epirubicin, mitoxantrone, adriamycin, bleomycin, mitomycin-C, dactinomycin, mithramycin, (v) taxanes, such as paclitaxel, docetaxel, Taxotere, Taxol, taxasm, 7-epipaclitaxel, t-acetyl paclitaxel, 10-desacetyl-paclitaxel, 10-desacetyl-7-epipaclitaxel, 7-xylosylpaclitaxel, 10-desacetyl-7-epipaclitaxel, 7-N—N-dimethylglycylpaclitaxel, 7-L-alanylpaclitaxel.

Also provided is a method of treatment of osteoporosis in a subject, the method comprising administering to a subject in need thereof a pharmaceutically effective amount of a compound of Formula (I), or a pharmaceutically acceptable salt, co-crystal, polymorph, solvate, hydrate, or enantiomer thereof. In one embodiment, the subject in need of treatment of osteoporosis is a postmenopausal woman. In another embodiment, the subject in need of treatment of osteoporosis is a man with osteoporosis.

Also provided is a method of prevention or inhibition of osteoporosis in a subject, the method comprising administering to a subject in need thereof a pharmaceutically effective amount of a compound of Formula (I), or a pharmaceutically acceptable salt, co-crystal, polymorph, solvate, hydrate, or enantiomer thereof.

Also provided is a method of treatment of glucocorticoid-induced osteoporosis in a subject, the method comprising administering to a subject in need thereof a pharmaceutically effective amount of a compound of Formula (I), or a pharmaceutically acceptable salt, co-crystal, polymorph, solvate, hydrate, or enantiomer thereof.

Also provided is a method of treatment of Paget's disease of the bone in a subject, the method comprising administering to a subject in need thereof a pharmaceutically effective amount of a compound of Formula (I), or a pharmaceutically acceptable salt, co-crystal, polymorph, solvate, hydrate, or enantiomer thereof.

Also provided is a method of treatment of osteogenesis imperfecta of the bone in a subject, the method comprising administering to a subject in need thereof a pharmaceutically effective amount of a compound of Formula (I), or a pharmaceutically acceptable salt, co-crystal, polymorph, solvate, hydrate, or enantiomer thereof.

Also provided are intermediate compounds of the formula:

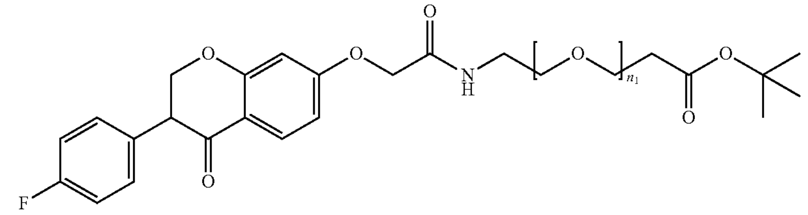

wherein:

$n_1$ is an integer selected from the group of 1, 2, 3, 4, 5, and 6.

Further provided are compounds of the formula:

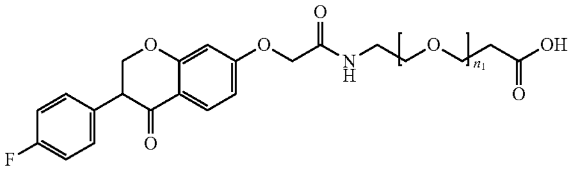

wherein:

$n_1$ is an integer selected from the group of 1, 2, 3, 4, 5, and 6.

Synthesis

Compounds as described herein may be prepared by methods known in the art. Specific examples of synthetic routes are presented. The method below for the preparation of 3-(4-fluorophenyl)-7-hydroxychroman-4-one (Compound A) may also be seen in U.S. 2016/0128973 A1.

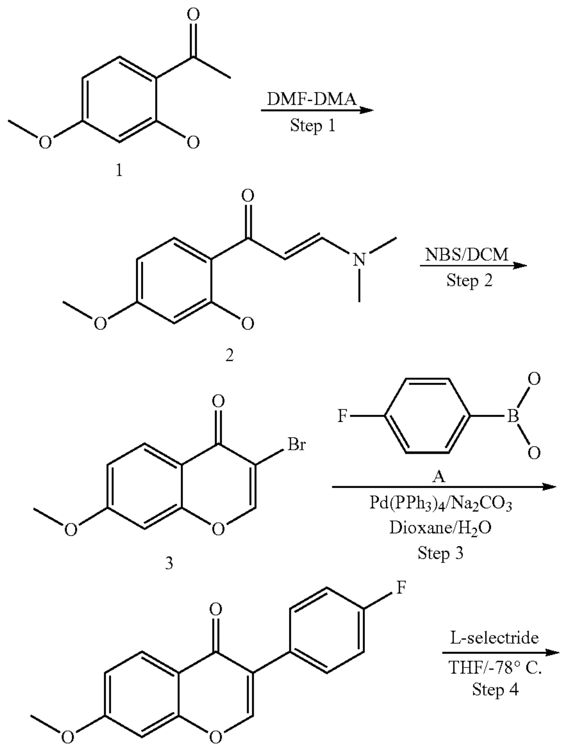

1 2 3 4

-continued

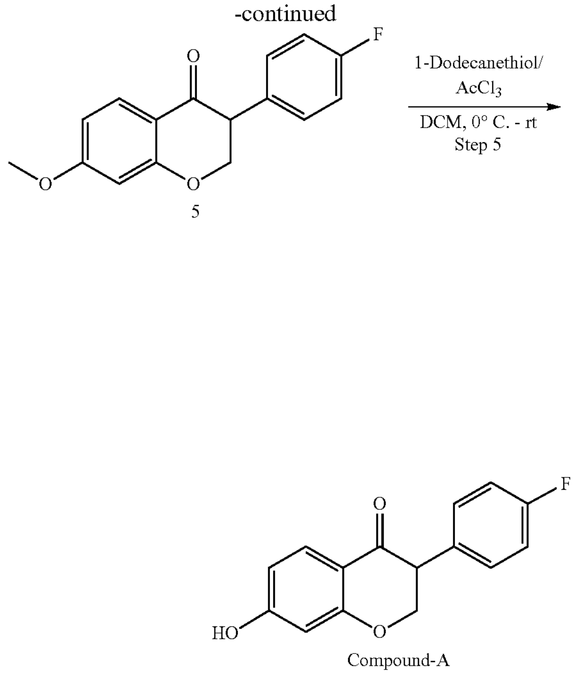

5

Compound-A

Compound A may be converted to 2-((3-(4-fluorophenyl)-4-oxochroman-7-yl)oxy)acetic acid, Compound B, by methods described in Chemical & Pharmaceutical Bulletin, 39(10), 2681-90; 1991, as follows.

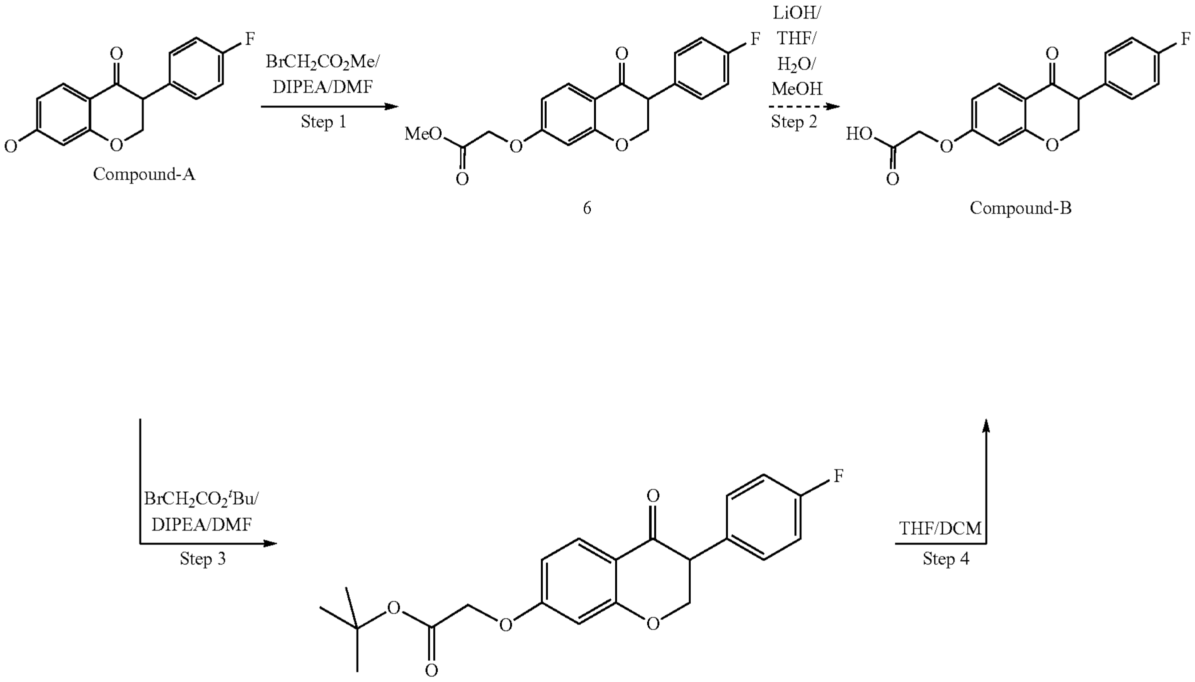

Compound-A 6 Compound-B

6a

Compound A may also be converted to the corresponding carbonate compound, 3-(4-fluorophenyl)-4-oxochroman-7-yl phenyl carbonate, Compound C, as follows at from 0°-RT (room temperature) for about an hour.

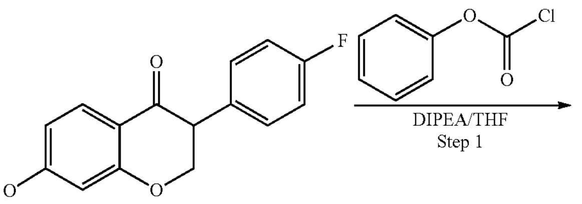

Compound-A

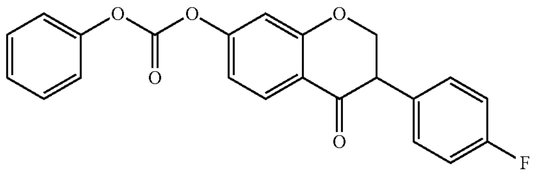

Compound-C

Zolendronic acid can be converted to 3-(3-amino-2-hydroxypropyl)-1-(2-hydroxy-2,2-diphosphonoethyl)-1H-imidazol-3-ium, Compound D, as follows.

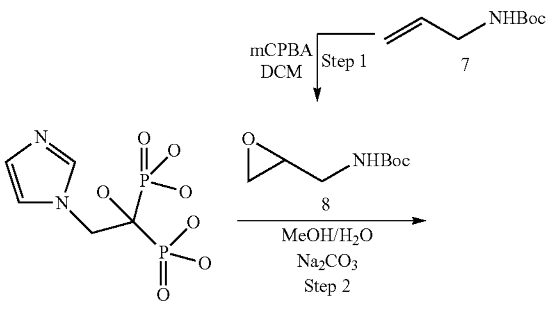

Zoledronic acid

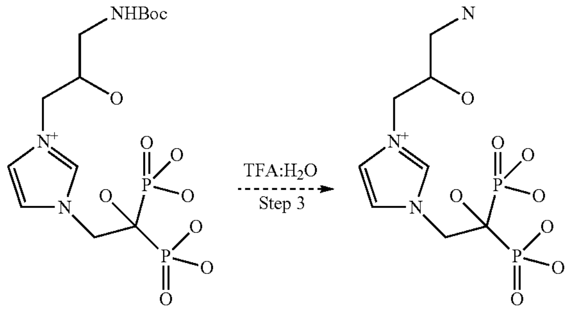

9

Compound-D

To reduce the inorganic residues 1.1 eq of $Na_2CO_3$ was used instead of saturated $Na_2CO_3$ solution for quaternization [step-2] reaction and 3-(3-((tert-butoxycarbonyl)amino)-2-hydroxypropyl)-1-(2-hydroxy-2,2-diphosphonoethyl)-1H-imidazol-3-ium, Compound 9, synthesized from this reaction was de-protected. This freshly prepared, Compound D, was used for the final amidation reaction without further purification.

Synthesis of (1-((3-(4-fluorophenyl)-4-oxochroman-7-yl)oxy)-21-hydroxy-2,16-dioxo-7,10,13-trioxa-3,17-diazahenicosane-21,21-diyl)bis(phosphonic acid) was then accomplished by the steps below. Synthesis of the three E compounds, (n=1), (n=2), (n=3), and (n=4) are accomplished with the corresponding starting materials:

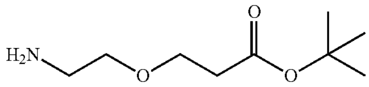

CAS Reg. No. 1260092-46-3

10a: tert-butyl 3-(2-aminoethoxy)propanoate

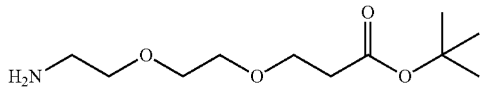 [SMILES: CC(C)(C)OC(=O)CCOCCOCCN]

CAS Reg. No. 756525-95-8

10b: tert-butyl 3-(2-(2-aminoethoxy)ethoxy)propanoate

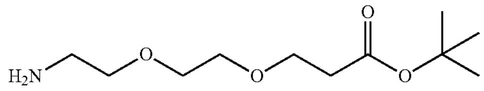 [SMILES: CC(C)(C)OC(=O)CCOCCOCCN]

CAS Reg. No. 756525-95-8

10c: tert-butyl 3-(2-(2-aminoethoxy)ethoxy)propanoate

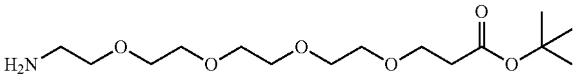 [SMILES: CC(C)(C)OC(=O)CCOCCOCCOCCOCCN]

CAS Reg No. 581065-95-4 tert-butyl 1-amino-3,6,9,12-tetraoxapentadncan-15-oate

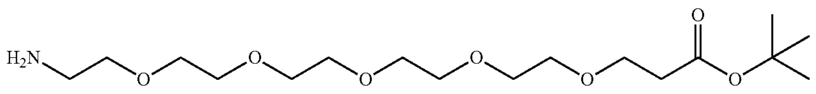 [SMILES: CC(C)(C)OC(=O)CCOCCOCCOCCOCCOCCN]

CAS Reg. No. 1446282-18-3 tert-butyl
1-amino-3,6,9,12,15-pentaoxaoctadecan-18-oate
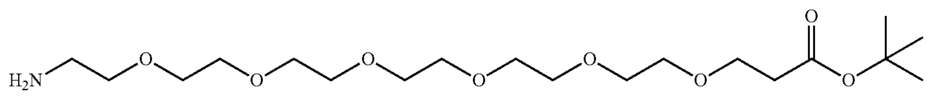 [SMILES: CC(C)(C)OC(=O)CCOCCOCCOCCOCCOCCOCCN]
CAS Reg. No. 1286281-32-0
tert-butyl
1-amino-3,6,9,12,15,18-hexaoxahenicosan-21-oate
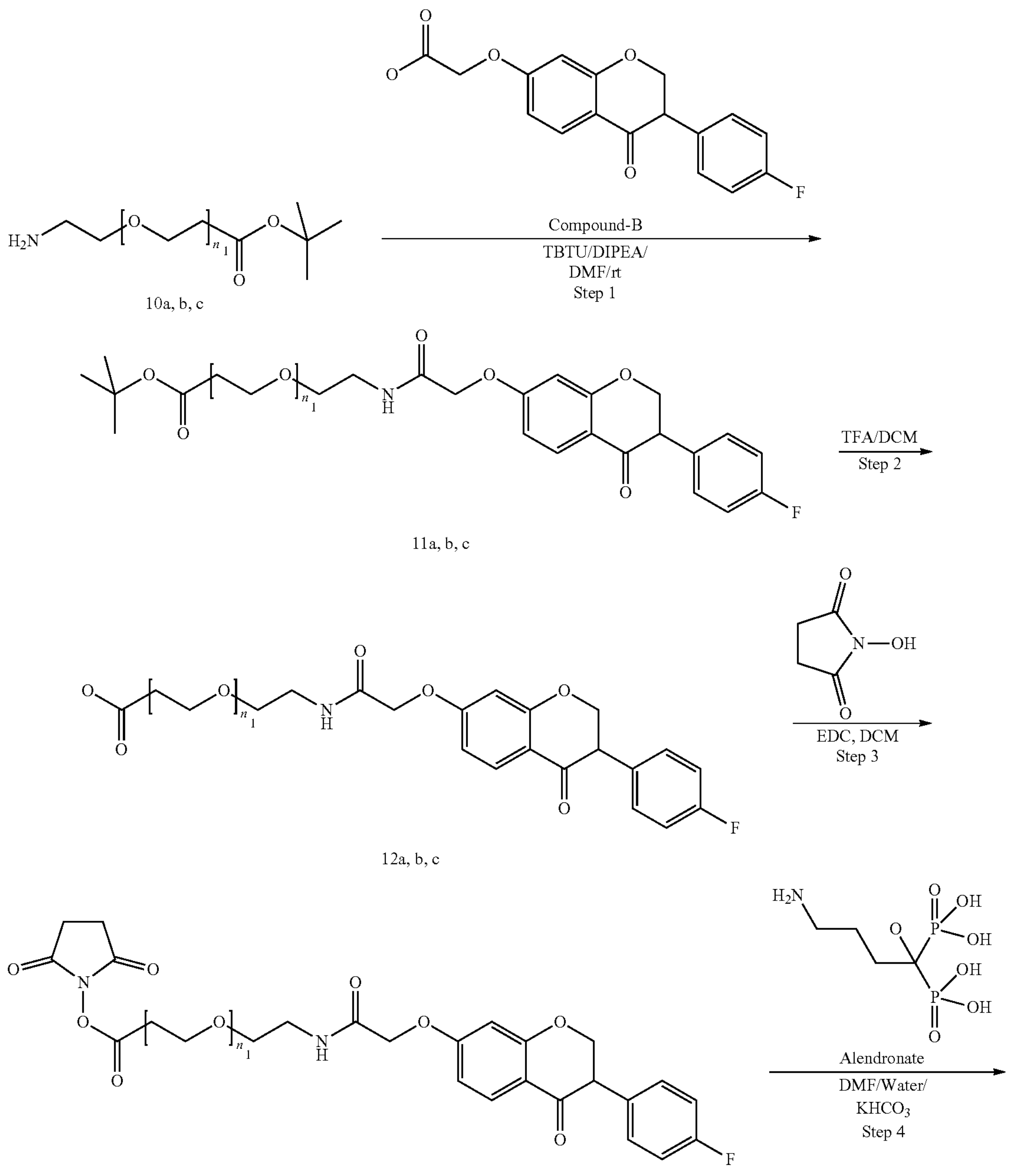

-continued

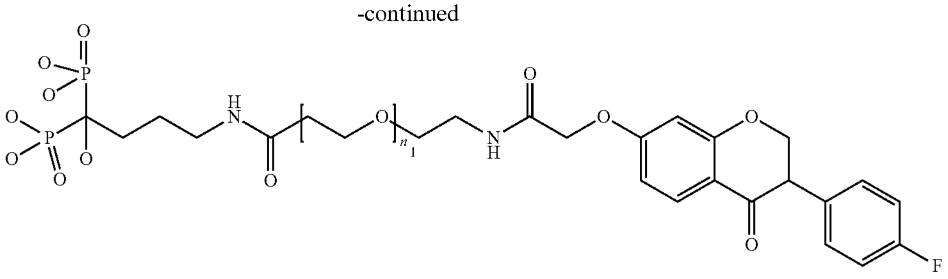

Compound E [$n_1$ = 3]

Compound E ($n_1$=1)

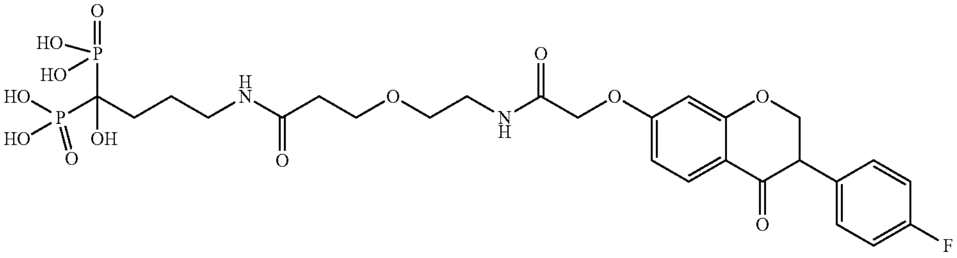 [SMILES: O=C(CCOCCNC(=O)COc1ccc2c(c1)OCC(c1ccc(F)cc1)C2=O)NCCCC(O)(P(=O)(O)O)P(=O)(O)O]

(4-(3-(2-(2-((3-(4-fluorophenyl)-4-oxochroman-7-yl)oxy)acetamido)ethoxy)propanamido)-1-hydroxybutane-1,1-diyl)bis(phosphonic acid)—obtained as a white solid. Chromatographic purity qualitative by HPLC (% by area normalization) at wavelength ($\lambda_{210\ nm}$): 97.14%. By NMR: Complies (1H); by Mass: Complies [M+H]: 663

$^1$H NMR (400 MHz, $D_2O$) δ (ppm) 7.93 (1H, d, J=8.9 Hz), 7.39-7.31 (2H, m), 7.19 (2H, t, J=8.8 Hz), 6.84 (1H, dd, J=9.0, 2.4 Hz), 6.65 (1H, d, J=2.4 Hz), 4.80-4.72 (4H, m), 4.24 (1H, t, J=7.4 Hz), 3.72 (2H, t, J=6.2 Hz), 3.63 (2H, t, J=5.2 Hz), 3.51 (2H, t, J=5.3 Hz), 3.22 (2H, t, J=6.8 Hz), 2.46 (2H, t, J=6.2 Hz), 1.99-1.95 (2H, m), 1.85-1.83 (2H, m).

Compound E ($n_1$=2)

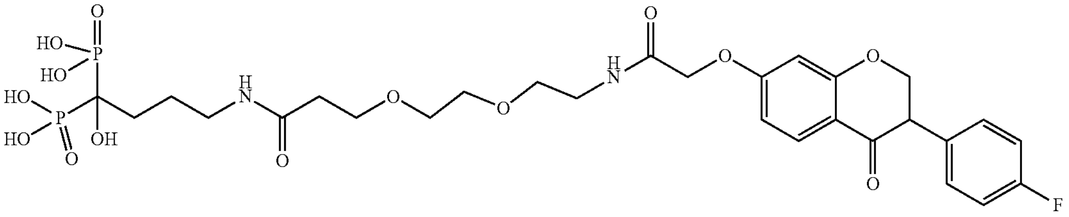 [SMILES: O=C(CCOCCOCCNC(=O)COc1ccc2c(c1)OCC(c1ccc(F)cc1)C2=O)NCCCC(O)(P(=O)(O)O)P(=O)(O)O]

(1-((3-(4-fluorophenyl)-4-oxochroman-7-yl)oxy)-17-hydroxy-2,12-dioxo-6,9-dioxa-3,13-diazaheptadecane-17,17-diyl)bis(phosphonic acid)—obtained as a white solid. Chromatographic purity qualitative by HPLC (% by area normalization) at wavelength ($\lambda_{210\ nm}$): 92.35%. By NMR: Complies (1H); by Mass: Complies [M+H]: 707

$^1$H NMR (400 MHz, $D_2O$) δ (ppm) 7.90 (1H, d, J=8.8 Hz), 7.34 (2H, t, J=6.8 Hz), 7.18 (2H, t, J=8.6 Hz), 6.81 (1H, d, J=9.0 Hz), 6.63 (1H, s), 4.76-4.72 (4H, m), 4.21 (1H, t, J=7.4 Hz), 3.75-3.72 (2H, m), 3.64-3.50 (8H, m), 3.21 (2H, t, J=6.8 Hz), 2.50 (2H, t, J=6.2 Hz), 1.98-1.95 (2H, m), 1.85-1.83 (2H, m).

Compound E ($n_1$=3)

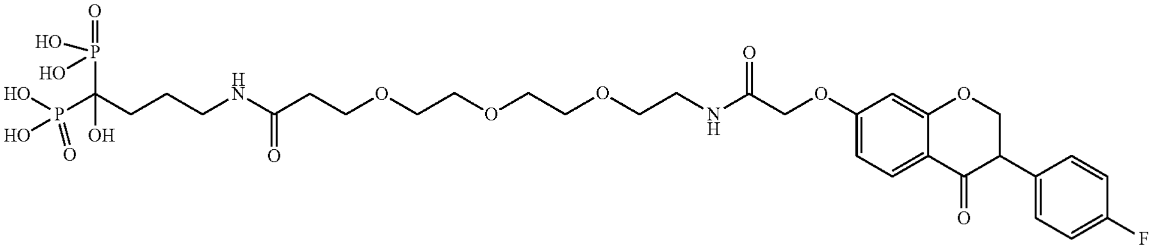 [SMILES: O=C(CCOCCOCCOCCNC(=O)COc1ccc2c(c1)OCC(c1ccc(F)cc1)C2=O)NCCCC(O)(P(=O)(O)O)P(=O)(O)O]

(1-((3-(4-fluorophenyl)-4-oxochroman-7-yl)oxy)-20-hydroxy-2,15-dioxo-6,9,12-trioxa-3,16-diazahenicosane-20,20-diyl)bis(phosphonic acid)—obtained as a white solid. Chromatographic purity qualitative by HPLC (% by area normalization) at wavelength ($\lambda_{210\ nm}$): 95.59%. By NMR: Complies (1H); by Mass: Complies [M+H]: 751

$^1$H NMR (400 MHz, $D_2O$) δ (ppm) 7.78 (1H, d, J=8.8 Hz), 7.22 (2H, t, J=7.0 Hz), 7.05 (2H, t, J=8.8 Hz), 6.69 (1H, d, J=9.7 Hz), 6.52 (1H, d, J=2.5 Hz), 4.63-4.61 (4H, m), 3.62 (2H, t, J=6.5 Hz), 3.53-3.48 (9H, m), 3.39 (2H, d, J=5.3 Hz), 3.09 (2H, t, J=6.7 Hz), 2.38 (2H, t, J=6.4 Hz), 1.82-1.78 (2H, m), 1.69-1.68 (2H, m).

Synthesis of Compounds G) ($n_1$=1), H ($n_1$=2), and I ($n_1$=3) is Accomplished by the Reaction

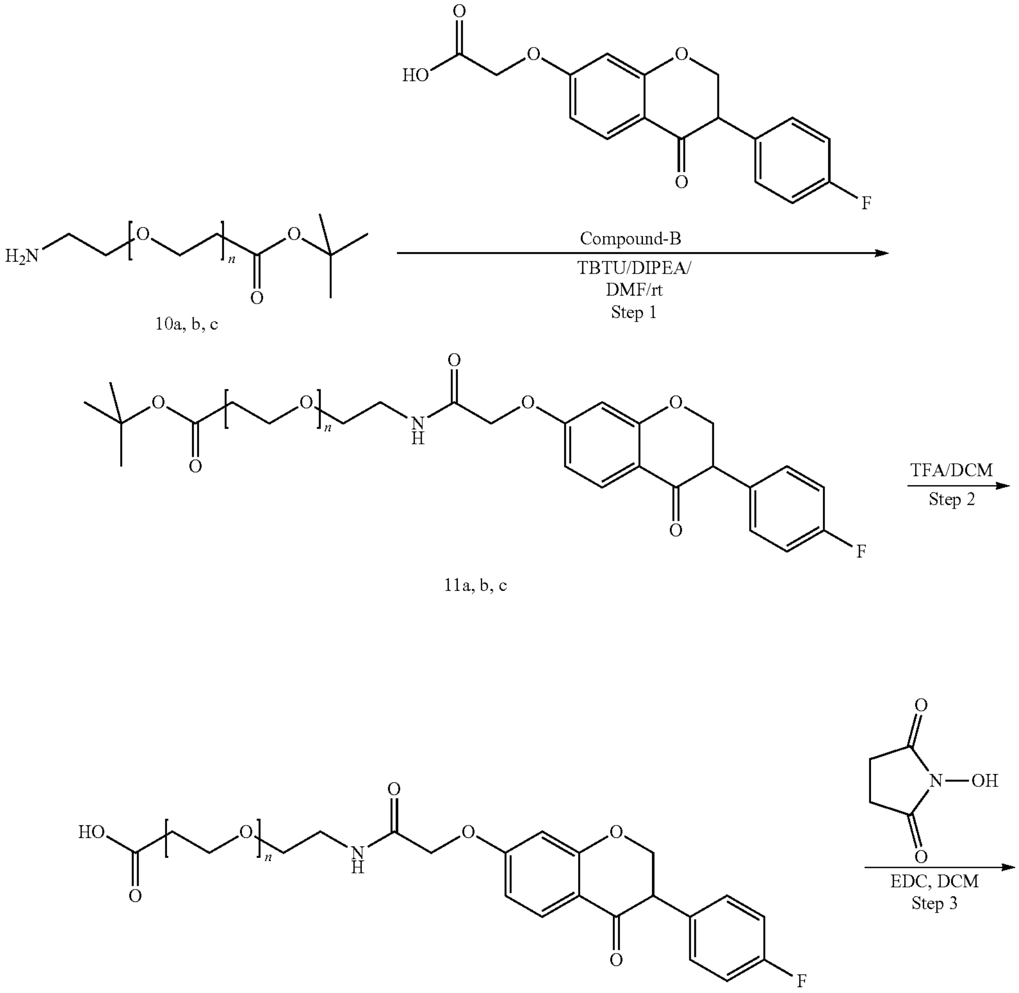

10a, b, c 11a, b, c 12a, b, c

-continued

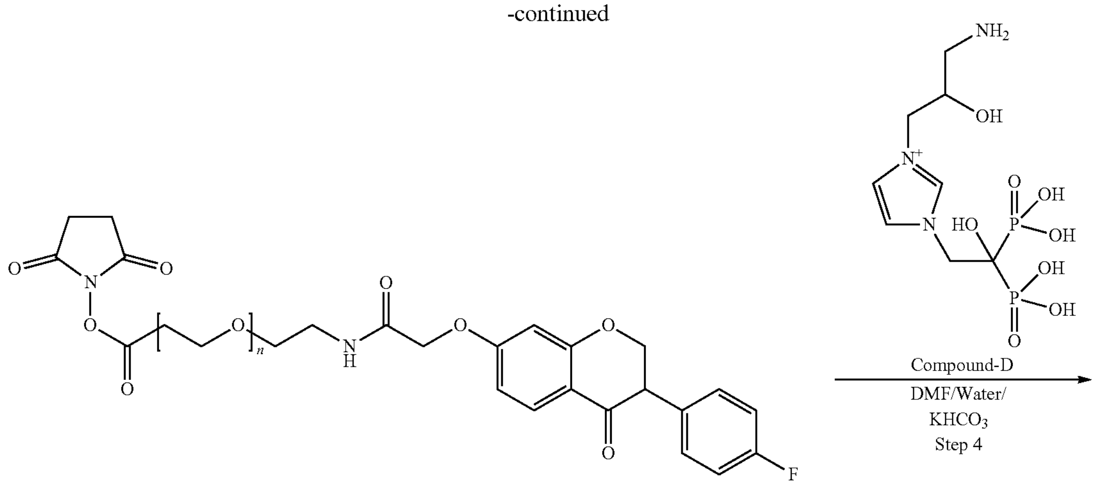

13a, b, c
WO 2017/132263

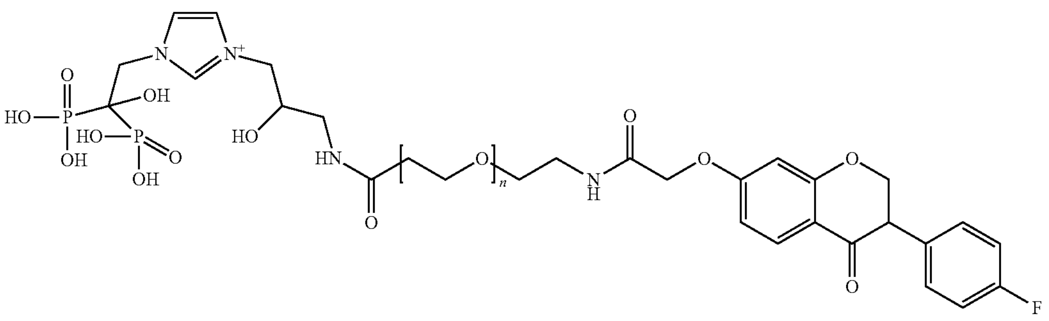

Compounds G ($n_1$ = 1), H ($n_1$ = 3), and I ($n_1$ = 4)

Compound G ($n_1$=1)

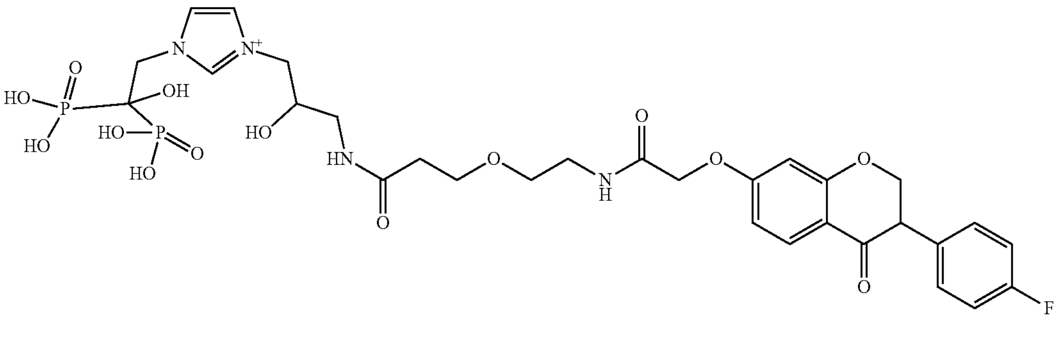 [SMILES: O=C(CCOCCNC(=O)COc1ccc2c(c1)OCC(c1ccc(F)cc1)C2=O)NCC(O)C[n+]1ccn(CC(O)(P(=O)(O)O)P(=O)(O)O)c1]

3-(3-(3-(2-(2-((3-(4-fluorophenyl)-4-oxochroman-7-yl)oxy)acetamido)ethoxy)propanamido)-2-hydroxypropyl)-1-(2-hydroxy-2,2-diphosphonoethyl)-1H-imidazol-3-ium—obtained as a white solid. Chromatographic purity qualitative by HPLC (% by area normalization) at wavelength ($\lambda_{210\ nm}$): 98.37%. By NMR: Complies (1H); by Mass: Complies [M+H]: 759

$^1H$ NMR (400 MHz, $D_2O$) δ (ppm) 8.82 (1H, s), 7.93 (1H, d, J=8.9 Hz), 7.58 (1H, t, J=1.8 Hz), 7.41-7.31 (3H, m), 7.18 (2H, t, J=8.8 Hz), 6.84 (1H, dd, J=9.0, 2.5 Hz), 6.66 (1H, d, J=2.4 Hz), 4.72-4.70 (2H, m), 4.22-4.07 (4H, m), 3.73 (2H, t, J=6.1 Hz), 3.64 (2H, t, J=5.1 Hz), 3.50 (2H, t, J=5.2 Hz), 3.41-3.39 (1H, m), 3.29-3.23 (1H, m), 2.50 (2H, t, J=6.1 Hz).

Compound H ($n_1$=2)

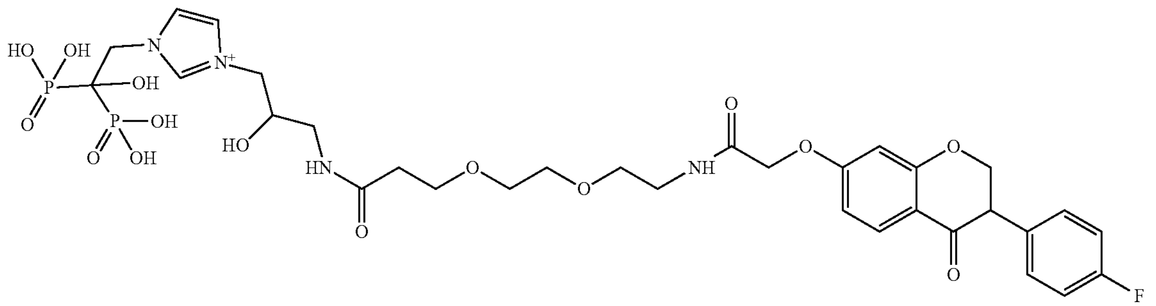 [SMILES: O=C(CCOCCOCCNC(=O)COc1ccc2c(c1)OCC(c1ccc(F)cc1)C2=O)NCC(O)C[n+]1ccn(CC(O)(P(=O)(O)O)P(=O)(O)O)c1]

3-(1-((3-(4-fluorophenyl)-4-oxochroman-7-yl)oxy)-15-hydroxy-2,12-dioxo-6,9-dioxa-3,13-diazanonadecan-16-yl)-1-(2-hydroxy-2,2-diphosphonoethyl)-1H-imidazol-3-ium–obtained as a white solid. Chromatographic purity qualitative by HPLC (% by area normalization) at wavelength ($\lambda_{210\ nm}$): 89.88%. By NMR: Complies (1H); by Mass: Complies [M+]: 803

$^1$H NMR (400 MHz, $D_2O$) δ (ppm) 8.83 (1H, s), 7.92 (1H, d, J=8.9 Hz), 7.58 (1H, s), 7.43 (1H, s), 7.35 (2H, t, J=7.0 Hz), 7.19 (2H, t, J=8.7 Hz), 6.82 (1H, d, J=9.0 Hz), 6.65 (1H, s), 4.68-4.65 (2H, m), 4.36-4.32 (1H, m), 4.22 (1H, t, J=7.2 Hz), 4.13-4.10 (2H, m), 3.76 (2H, t, J=6.0 Hz), 3.74-3.64 (6H, m), 3.63-3.59 (2H, m), 3.50-3.45 (1H, m), 3.41-3.38 (1H, m), 2.56 (2H, t, J=5.9 Hz).

Compound I ($n_1$=3)

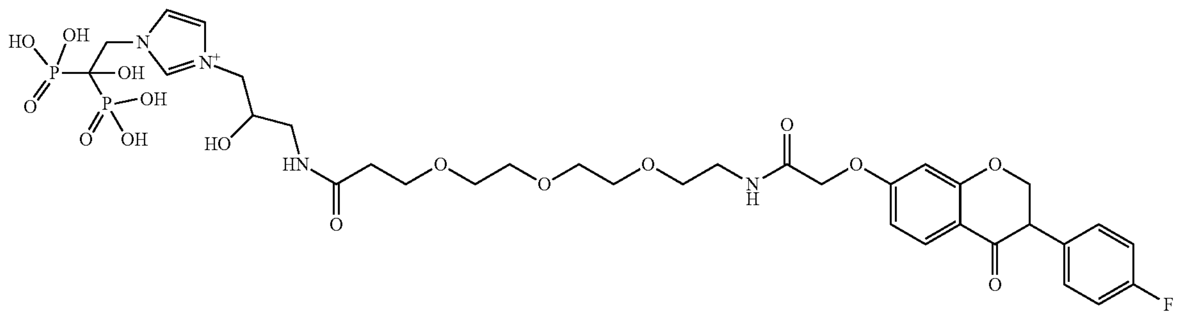 [SMILES: O=C(CCOCCOCCOCCNC(=O)COc1ccc2c(c1)OCC(c1ccc(F)cc1)C2=O)NCC(O)C[n+]1ccn(CC(O)(P(=O)(O)O)P(=O)(O)O)c1]

3-(1-((3-(4-fluorophenyl)-4-oxochroman-7-yl)oxy)-18-hydroxy-2,15-dioxo-6,9,12-trioxa-3,16-diazanonadecan-19-yl)-1-(2-hydroxy-2,2-diphosphonoethyl)-1H-imidazol-3-ium-obtained as a white solid. Chromatographic purity qualitative by HPLC (% by area normalization) at wavelength ($\lambda_{210\ nm}$): 94.61%. By NMR: Complies (1H); by Mass: Complies [M+]: 847

$^1$H NMR (400 MHz, $D_2O$) δ (ppm) 8.84 (1H, s), 7.92 (1H, d, J=8.8 Hz), 7.58 (1H, s), 7.44 (1H, s), 7.35 (2H, t, J=7.1 Hz), 7.19 (2H, t, J=8.8 Hz), 6.83 (1H, d, J=9.0 Hz), 6.66 (1H, d, J=2.4 Hz), 4.81-4.74 (6H, m), 4.72-4.69 (2H, m), 4.38 (1H, d, J=11.2 Hz), 4.26-4.14 (1H, m), 4.13-4.11 (2H, m), 3.76 (2H, t, J=6.1 Hz), 3.69-3.58 (8H, m), 3.53 (2H, d, J=5.3 Hz), 3.46-3.42 (1H, m), 3.35-3.30 (1H, m), 2.55 (2H, t, J=6.0 Hz).

Synthesis of Compound L
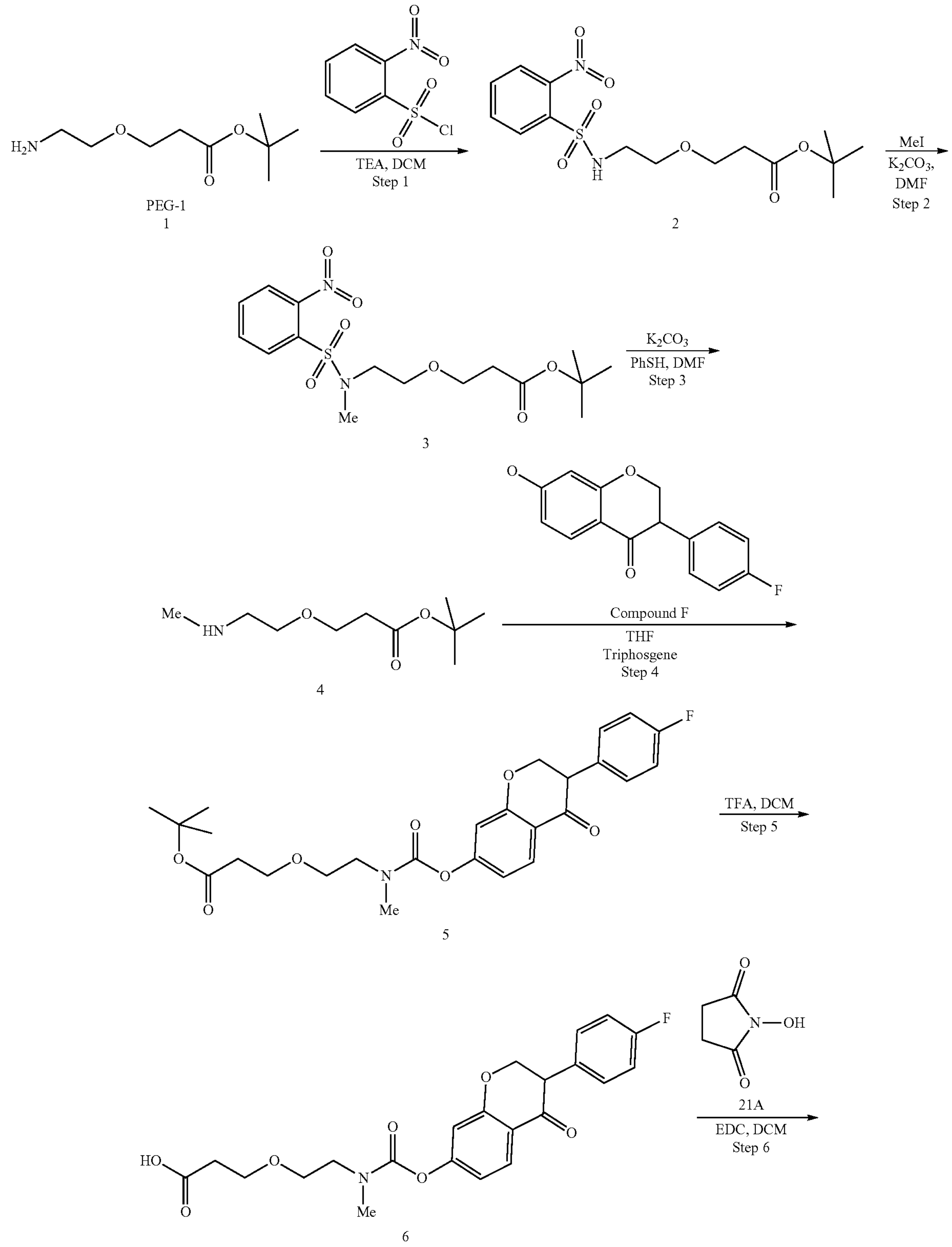
PEG-1
1
2
3
4
5
6

-continued

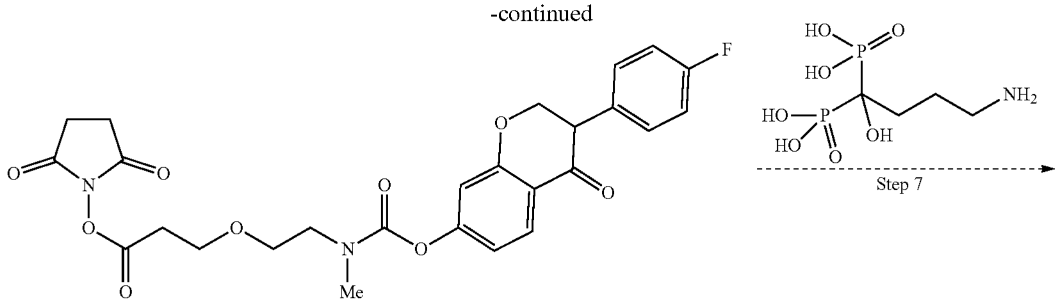

7

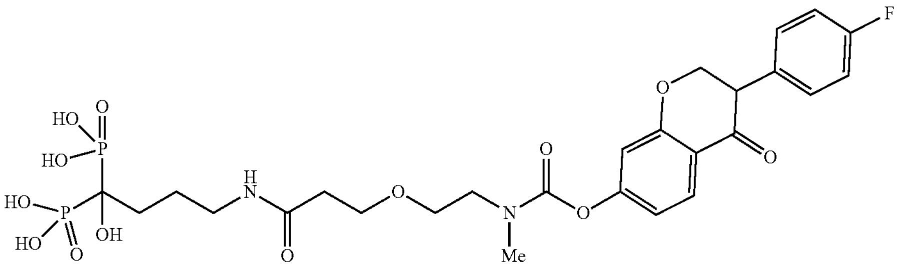

Compound L

Compound L: (4-(3-(2-((((3-(4-fluorophenyl)-4-oxochroman-7-yl)oxy)carbonyl)(methyl)amino)ethoxy)propanamido)-1-hydroxybutane-1,1-diyl)bis(phosphonic acid)

Nosyl group protection was performed with PEG-1 followed by N-alkylation on 0.5 g scale and isolated 0.4 g of compound 3. Nosyl deprotection of compound 3 was accomplished on 0.4 g [PhSH (1 eq.)/$K_2CO_3$ (2.5 eq.)/DMF/RT] scale. Work up followed by purification provided 0.14 g of desired compound 4. 0.7 g of compound 4 was isolated after two steps of PEG-1 on 2 g scale. Coupling of compound 4 with compound F was done on 0.25 g [F (1.1 eq.)/triphosgene (0.5 eq.)/DIPEA (2 eq.)/DCM/0° C./1 h] scale. Work up followed by several purifications provided 0.11 g of desired compound 5. Tert-butyl deprotection followed by preparation Osu derivative (Int-7) in 0.11 g [TFA/DCM/RT/5 h then N-hydroxy succinimide (1.5 eq.)/EDC·HCl (3.0 eq.)/DCM/0° C. to RT/16 h] scale. Work up provided 0.2 g of desired Osu derivative 7. Final coupling of Intermediate 7 with alendronic acid (compound H) was performed on 0.05 g [alendronic acid (1.7 eq.)/$KHCO_3$ (2.0 eq.)/DMF/Water] scale, which was submitted for prep-HPLC purification. Now analysis is underway. Final coupling of Intermediate 7 with alendronic acid (compound H) was performed on 0.350 g [alendronic acid (1.7 eq.)/$KHCO_3$ (2.0 eq.)/DMF/Water] scale.—obtained as a white solid. Chromatographic purity qualitative by HPLC (% by area normalization) at wavelength ($\lambda_{210\ nm}$): 97.39%. By NMR: Complies (1H); by Mass: Complies [M+H]: 663

$^1$H NMR (400 MHz, $D_2O$) δ (ppm) 8.00 (1H, d, J=8.5 Hz), 7.38 (2H, br s), 7.21 (2H, t, J=8.5 Hz), 6.94 (2H, d, J=11.7 Hz), 4.34 (1H, t, J=7.9 Hz), 3.86 (2H, d, J=6.0 Hz), 3.81-3.77 (2H, m), 3.73 (1H, br s), 3.59 (1H, br s), 3.26-3.21 (2H, m), 3.18 (1H, s), 3.06 (2H, s), 2.57 (2H, br s), 1.98-1.95 (2H, m), 1.86-1.83 (2H, m).

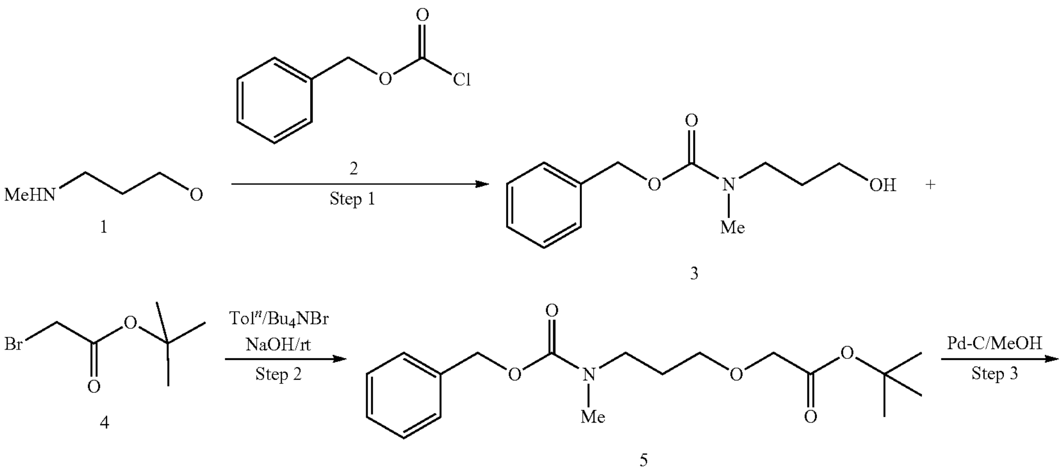

-continued
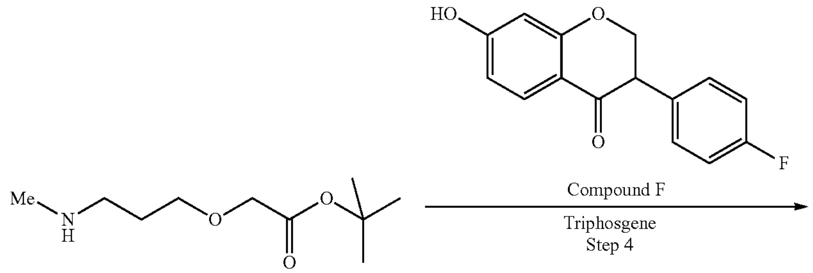
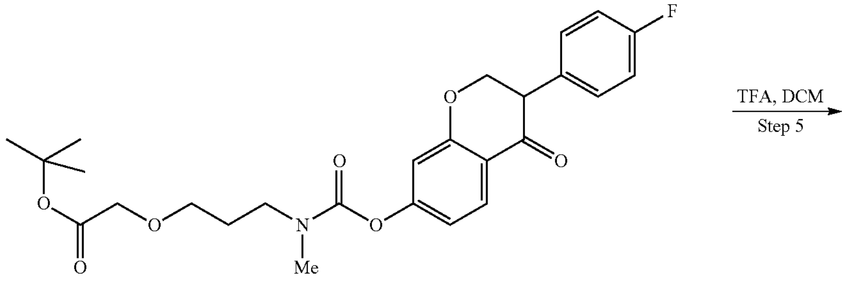
7
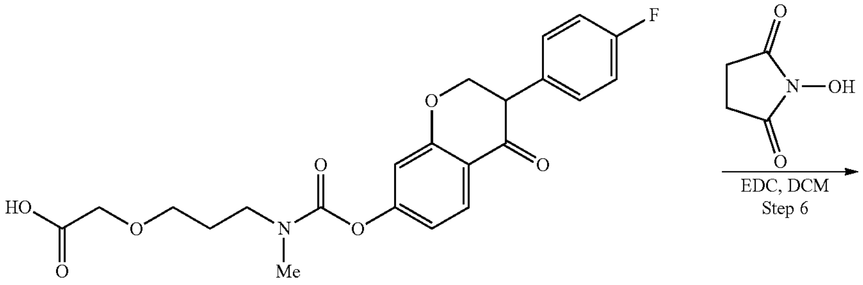
8
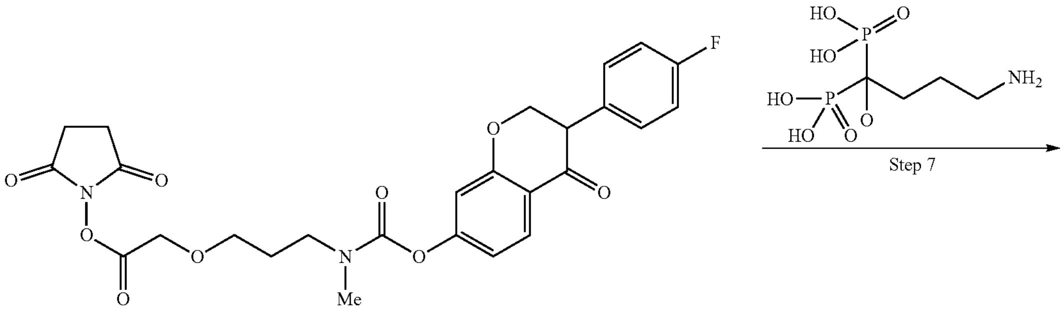
9
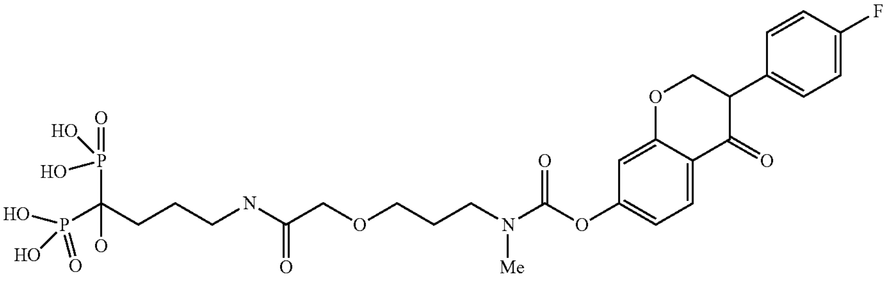
Compound M Compound M: (4-(2-(3-((((3-(4-fluorophenyl)-4-oxochroman-7-yl)oxy)carbonyl)(methyl)amino) propoxy)acetamido)-1-hydroxybutane-1,1-diyl)bis (phosphonic acid)

CBZ protection (Step-1) was performed on 5 g scale with 3-(methylamino)propanol (SM 1) followed by O-alkylation (Step-2), we have isolated 4.5 g of compound 5. CBZ deprotection (Step-2) of compound 5 was carried out on 4.5 g [Pd—C/$H_2$/MeOH/RT] scale to achieve 2.6 g of compound 6. A coupling reaction between amine intermediate 6 with triphosgene has been attempted on 500 mg [triphosgene (0.5 eq.)/$NaHCO_3$/$CH_2Cl_2$/DMF/$H_2O$/0° C. to RT] scale. SM remains unreacted even after 12 h. A coupling reaction between compound F with triphosgene has been attempted on 700 mg [triphosgene (0.5 eq.)/DIPEA/$CH_2Cl_2$/DMF/0° C. to RT] scale, we have isolated 400 mg of compound 7. 0.380 g of compound 8 was obtained as crude after the 0.4 g [TFA/DCM] scale deprotection of Compound 7. Preparation of OSu derivative (compound 9) has been attempted in 0.38 g [N-hydroxy succinimide (1.5 eq.)/EDC·HCl (3.0 eq.)/DCM/0° C. to RT/2 h] scale. Work up provided 0.4 g of desired compound 9 as crude. Finally coupling reaction of compound 9 and alendronic acid has been performed on 0.4 g [alendronic acid (1.7 eq.)/$KHCO_3$ (2.0 eq.)/DMF/$H_2O$/RT] scale. Crude LCMS suggested the formation of desire compound M which was purified by prep-HPLC and isolated 0.66 g of final compound M.—obtained as a white solid. Chromatographic purity qualitative by HPLC (% by area normalization) at wavelength ($\lambda_{210\ nm}$): 99.00%. By NMR: Complies (1H); by Mass: Complies [M+H]: 663

$^1$H NMR (400 MHz, $D_2O$) δ (ppm) 8.00 (1H, d, J=8.6 Hz), 7.38-7.36 (2H, m), 7.22 (2H, t, J=8.8 Hz), 6.97-6.93 (2H, m), 4.35 (1H, t, J=7.7 Hz), 4.10 (1H, s), 4.05 (1H, s), 3.70 (3H, br s), 3.52 (1H, br s), 3.31 (1H, br s), 3.20-3.17 (2H, m), 3.05 (1H, s), 2.02-2.00 (4H, m), 1.86-1.84 (2H, m).

Additional information is available in the article *A Multifunctional Therapy Approach for Cancer: Targeting Raf1-Mediated Inhibition of Cell Motility, Growth, and Interaction with Microenvironment*, Zhang et al., Molecular Cancer Therapeutics, 19(1), January 2020, pp. 39-51, which is incorporated herein by reference in its entirety.

Studies

KBU2046 does not Interfere with the Activity of Chemotherapy

Chemotherapy is widely used in the treatment of androgen independent PCa, both docetaxel and cabazitaxel have been shown to prolong life (Tannock et al., *N Engl J Med* 351, 1502-1512 (2004); Sweeney et al., *N Engl J Med* 373, 737-746 (2015); and Bono et al., *Lancet* 376, 1147-1154 (2010)), and both are taxanes that target microtubule function, thereby inhibiting cell growth (Lyseng-Williamson et al., Drugs 65, 2513-2531, 2005). Combining chemotherapy with KBU2046 did not affect the ability of either docetaxel or cabazitaxel to inhibit the growth of androgen independent PC3-M cells in vitro (FIG. 1A).

A similar lack of interference upon cytotoxic action was also observed when KBU2046 was co-administered with agents spanning different pharmacologic classes including, adriamycin, taxol and vinblastine, an effect demonstrated in both PC3-M cells and MDA-MB-231 human breast cancer cells. In order to evaluate whether KBU2046 would inhibit the efficacy of chemotherapy in vivo, mice were subcutaneously implanted with PC3-M cells and treated with docetaxel±KBU2046 (FIG. 1B). Compared to control mice, docetaxel significantly inhibited tumor growth (P<0.01). However, KBU2046 did not significantly affect growth when added to control or docetaxel treated mice. These findings demonstrate that KBU2046 does not inhibit the efficacy of cytotoxic agents.

Figure 1A:
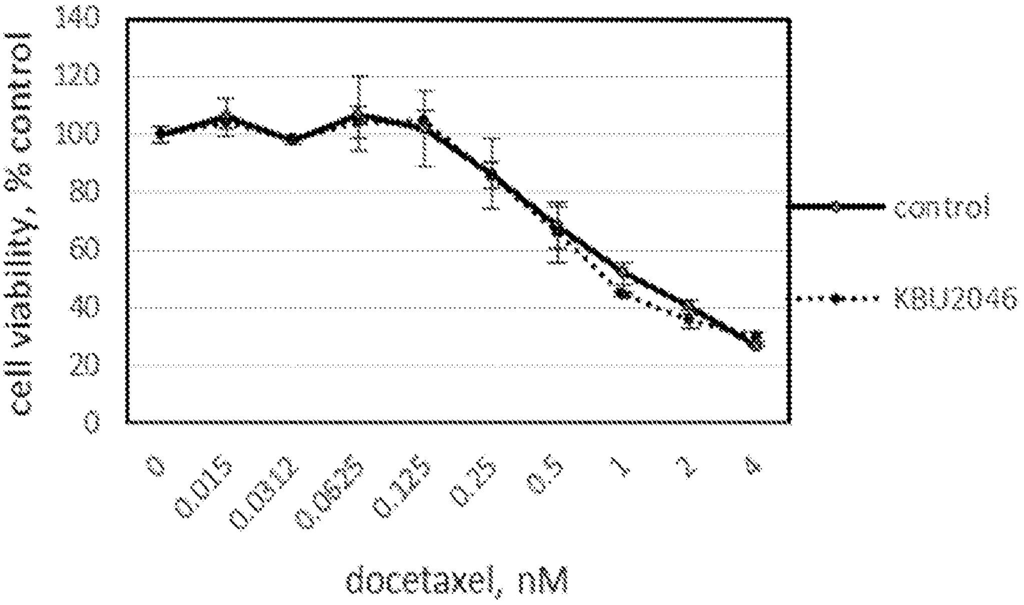
Figure 1A:
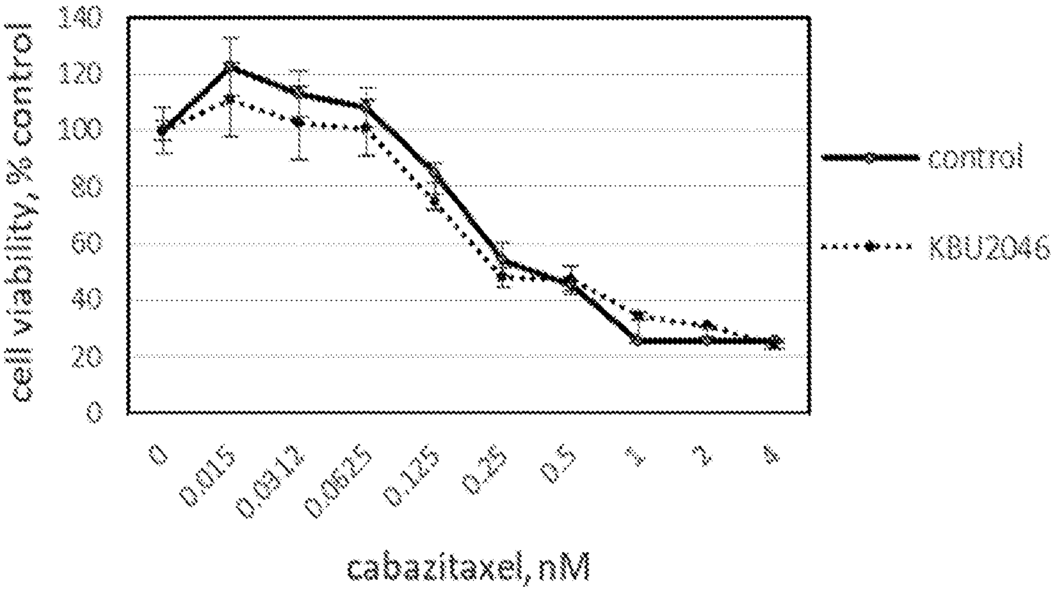
Figure 1B:
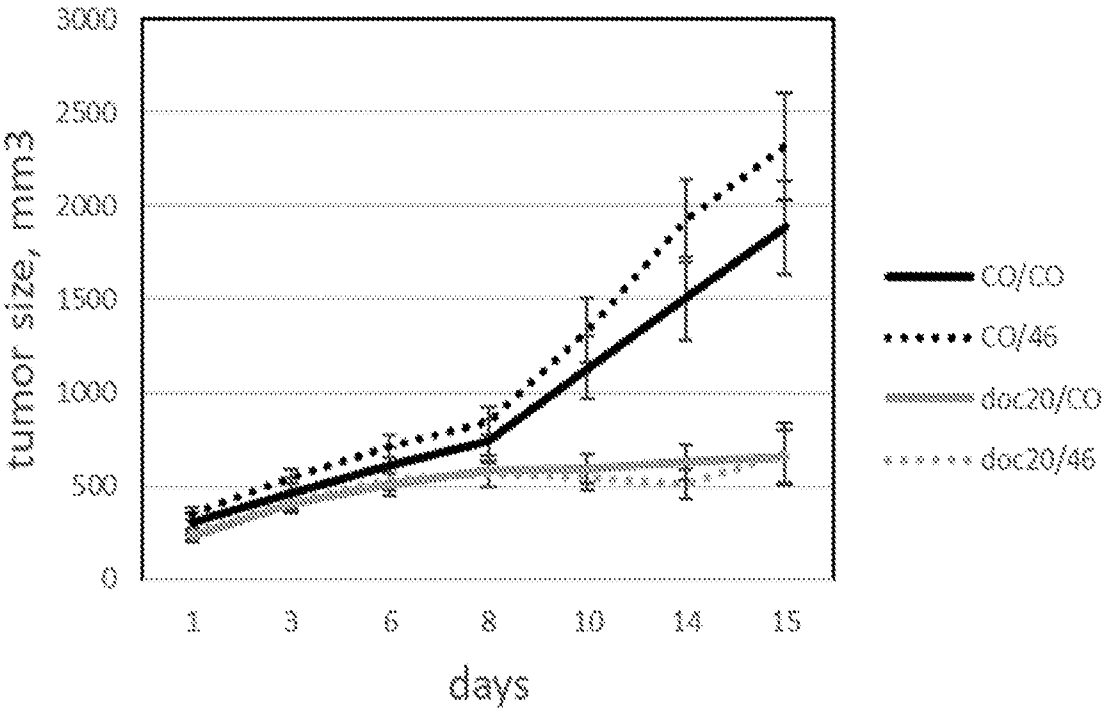

FIG. 1 demonstrates KBU2046 does not inhibit chemotherapy efficacy against prostate cancer. FIG. 1A depicts the effect of chemotherapy on the growth of androgen independent PC3-M PCa cells in vitro. Data are the mean±SEM (N=3 replicates) of cell viability in a 3 day growth assay in the presence of 10 μM KBU2046 or vehicle (control) treated with docetaxel or cabazitaxel. FIG. 1B depicts the effect of chemotherapy on the growth of androgen independent PCa cells in vivo. Mice received subcutaneous implants of PC3-M cells, were monitored until tumors were detectable (250 mm$^3$), and then treated daily with oral 80 mg KBU2046/kg or vehicle (CO) and with weekly intraperitoneal docetaxel (doc) at 0 or 20 mg/kg, beginning on day 1, and tumor size measured. Data are mean±SEM, with N=20 mice per cohort.

Combining Anti-Motility Therapy with Cytotoxic Therapy has Improved Efficacy

Unregulated cell growth and unregulated cell movement constitute two elemental processes of cancer. A therapeutic strategy wherein both of these processes are targeted is rationally-based. We sought to examine if the combination of docetaxel plus KBU2046 would achieve the sustained inhibition of tumor growth kinetics of docetaxel while providing for improved antimetastatic efficacy, as compared to either agent alone. The PC3-M orthotopic implantation murine model allows for the quantification of primary tumor growth, the assessment of distant metastasis to the lungs, and has previously been used to measure the effects of therapy and genetic alterations on metastasis (Xu et al., *Nature Communications* 9, 2454 (2018); Pavese et al., *PLoS One* 9, e102289 (2014); and Lakshman et al., *Clin Exp Metastasis* 28, 39-53 (2011)).

Figure 2A:
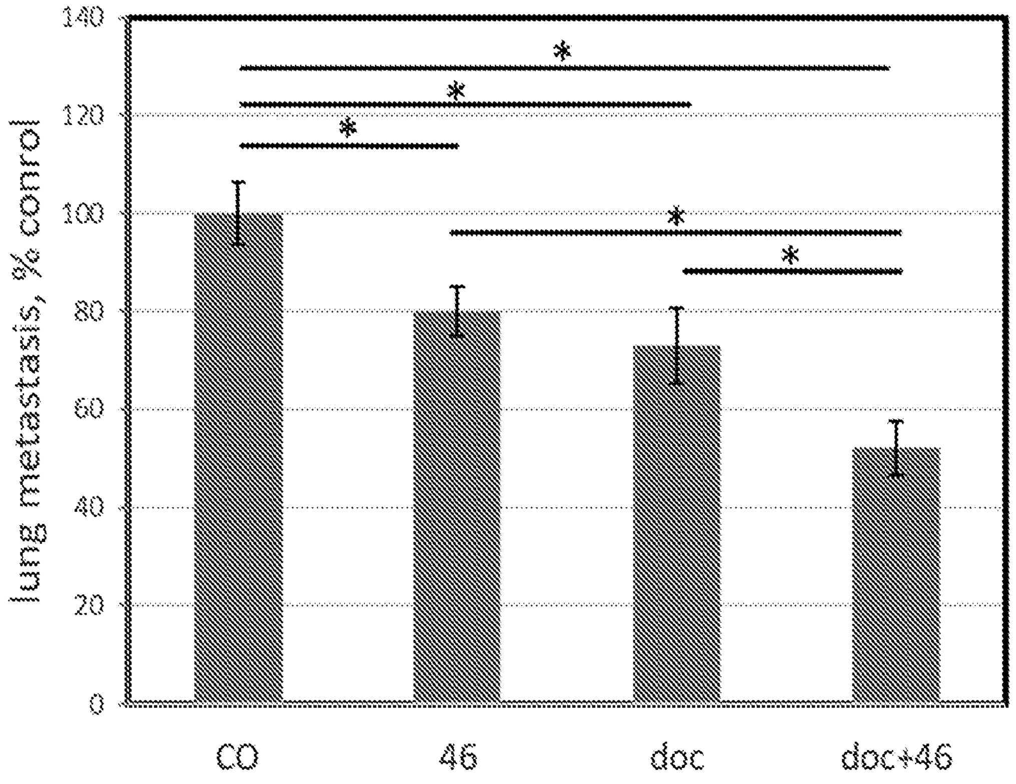
Figure 2B:
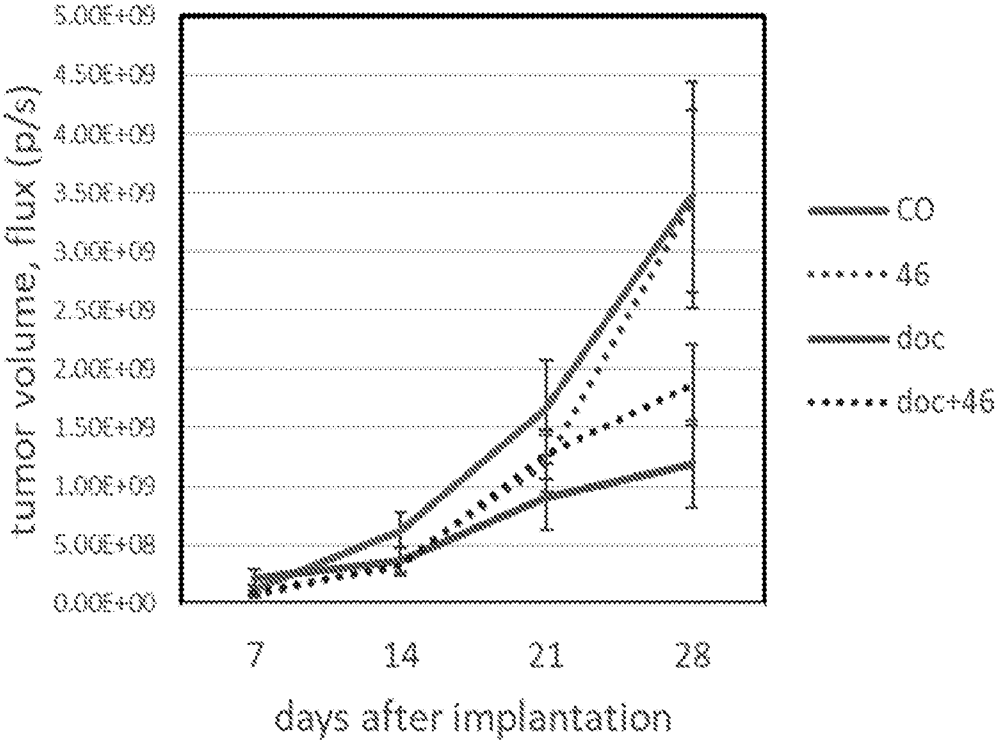
Figure 2C:
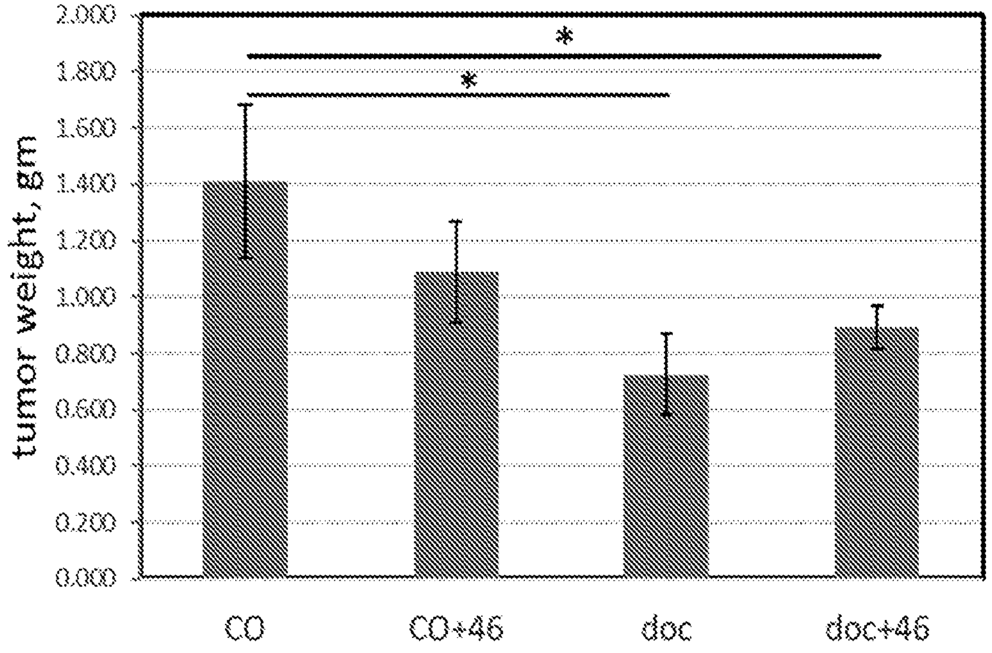

To assess the efficacy of a spectrum of docetaxel concentrations, mice received orthotopic implants of PC3-M-luc cells, were treated with 0, 10 or 20 mg/kg docetaxel, and tumor growth monitored with weekly IVIS imaging. Docetaxel significantly inhibited growth compared to controls in a dose-dependent manner. Subsequently, mice with orthotopic implants of PC3-M-luc cells were treated with docetaxel, KBU2046, docetaxel+KBU2046 or vehicle, as denoted, and effects on primary tumor growth and lung metastasis quantified (FIGS. 2A, 2B, and 2C). Prior studies demonstrated that it is possible to detect as few as 10 human cells per mouse organ, i.e. kidney, using human Alu element-specific qPCR (Funakoshi et al., *Sci Rep* 7, 13202 (2017)). We demonstrate that there is a linear relationship between number of PC3-M-luc cells present in mouse lung and qPCR-based detection of human Alu elements (Pearson $R^2$=0.96). Using human Alu element-specific qPCR to quantify PC3-M-luc metastasis to lungs, we demonstrated that docetaxel, KBU2046 and docetaxel+KBU2046 decreased metastasis by 23% (P<0.05), 20% (P<0.05) and 48% (P<0.001), respectively, compared to control mice. Of note, the combination of these two differentially acting agents achieved a significantly greater decrease in metastasis than that observed with either docetaxel (P<0.05) or KBU2046 (P<0.01) alone (FIG. 2A). Based upon the effect of each treatment alone, the calculated combined effect of docetaxel+KBU2046 is 42% reduction, giving an experimental/calculated ratio of 1.1, or additive-to-slightly-synergistic.

Evaluation of prostate tumor growth by weekly IVIS imaging demonstrated exponential growth kinetics in cohorts not receiving docetaxel, and slower growth in cohorts receiving docetaxel (FIG. 2B). Measurement of actual tumor weight demonstrated that docetaxel and docetaxel+KBU2046 decreased tumor weight by 49% (Fisher's exact $P<0.05$) and 37% (Fisher's exact $P<0.05$), respectively, compared to control (FIG. 2C). KBU2046 as a standalone agent had no significant effect, nor did it significantly impair docetaxel's efficacy. These findings demonstrate that combining anti-motility therapy with cytotoxic therapy allows dual targeting of cell growth and cell movement, resulting in sustained control of primary tumor growth and enhanced control of metastatic disease progression.

FIGS. 2A-2C demonstrate that KBU2046 plus docetaxel exhibits increased anti-metastatic efficacy. Cohorts of N=10 mice bearing orthotopic implants of PC3-M-luc cells were treated daily with 150 mg/kg KUB2046, intraperitoneal docetaxel 7.5 mg/kg weekly (doc), the combination (doc+46), or with oral and intraperitoneal vehicle (CO). KBU2046 treatment began 3 days before implantation and docetaxel began 1 week after. (FIG. 2A) Lung metastasis measured by qPCR for human Alu sequences, expressed as percent control (FIG. 2B) Weekly IVIS imaging of tumor. (FIG. 2C) Tumor weight. *denotes $P<0.05$ for differences between cohorts denoted by bars. All data are mean±SEM.

KBU2046 does not Interfere with Hormone Therapy

Hormonal therapy is the mainstay of treatment for metastatic PCa (N. C. C. Network, Prostate Cancer. *NCCN Clinical Practice Guidelines in Oncology* (NCCN Guidelines®) Version 4, (2018)). It is therefore important to ensure other therapeutic modalities do not interfere with it. Initial hormone treatment involves decreasing testicular androgen production, and is termed androgen deprivation therapy (ADT). Disease progression, which is inevitable, is termed castrate-resistant PCa, and is commonly treated with an androgen receptor (AR) antagonist, such as enzalutamide (Beer et al., *N Engl J Med* 371, 424-433 (2014)). To evaluate KBU2046's effect upon this paradigm investigations began with the androgen sensitive LNCaP and VCaP human PCa cells, which have been well characterized for their response to hormonal targeted therapies (Furr et al., *Eur Urol* 29 Suppl 2, 83-95 (1996) 23; and Tran et al., *Science* 324, 787-790 (2009)).

Cells were cultured in media depleted of androgen and after a washout of 72 hrs were treated with the synthetic androgen R1881, KBU2046, enzalutamide and/or vehicle (control), and resultant effects upon induction of the androgen-responsive gene, prostate specific antigen (PSA) were measured (FIG. 3A). In both cell lines, R1881 significantly increased PSA expression and enzalutamide decreased it. In LNCaP cells, KBU2046 had no significant effect. In VCaP cells, KBU2046 significantly decreased PSA expression in R1881 treated cells by 36% ($P<0.05$). While it also significantly increased expression in control cells ($P<0.05$), absolute baseline levels were very low and the relative increase was only 14%. Evaluating effects on cell growth, enzalutamide significantly inhibited it compared to controls ($P<0.05$) in both LNCaP and VCaP cells, whereas the addition of KBU2046 to either control or enzalutamide treated cells had no significant effect (FIGS. 3C and 3D).

Several considerations warranted a deeper examination of the effect of KBU2046 on AR function. In VCaP cells KBU2046 significantly inhibited R1881-mediated PSA gene expression, consistent with inhibition of AR function. Additionally, AR is a client protein of HSP90, AR function requires HSP90-mediated chaperone action, and direct inhibitors of HSP90 decrease client protein expression and inhibit AR function (Fang et al., *J Biol Chem* 271, 28697-28702 (1996); Saporita et al., *Prostate* 67, 509-520 (2007); and Ni et al., *Mol Cell Biol* 30, 1243-1253 (2010)). KBU2046 is not a direct inhibitor of HSP90, and as such does not globally decrease client protein expression. It is a selective HSP90 activity modulator (SHAM), and selectively modulates client proteins that regulate cell motility. However, the effect of KBU2046 on AR expression and function had not been examined. After ligand binding, functional AR translocates from the cytoplasm to the nucleus, and nuclear localization therefore provides a measure of functional AR. By treating LNCaP and VCaP cells with R1881, KBU2046, and/or enzalutamide, and measuring AR expression by Western blot in resultant nuclear and cytoplasmic cellular fractions, we demonstrated that KBU2046 did not affect AR expression or nuclear localization in response to R1881, nor its inhibition by enzalutamide (FIG. 3E).

To complete our assessments of the androgen related paradigm, the effect of KBU2046 on resistance to hormone therapy was evaluated. The outgrowth of LNCaP/AR-luc cells in castrate mice is routinely utilized as a model to emulate the transition to a castration resistant phenotype (Tran et al., *Science* 324, 787-790 (2009)). In this model, tumor outgrowth is detectable ~8 weeks post implantation, and growth kinetics are typically monitored until 16 weeks post implantation. Here, two treatment approaches were investigated, the effects of beginning treatment early at 4 weeks, or late at 12 weeks, and were performed in mice receiving subcutaneous or orthotopic implants, respectively (FIGS. 3F and 3G). KBU2046 did not alter tumor growth in either model. Taken together, these findings support the notion that KBU2046 does not affect androgen signaling, nor does it inhibit the efficacy of ADT or of AR antagonist therapy.

FIGS. 3A-3E help demonstrate that KBU2046 also does not affect androgen signaling nor therapeutic targeting. LNCaP or VCaP cells cultured in hormone free media were treated with R1881 (R), KBU2046 and/or enzalutamide (E). (FIGS. 3A and 3B) Effects on AR-responsive gene expression. PSA expression was measured by qRT/PCR, normalized to GAPDH and expressed as a percent of control cells (N=3 replicates); * denotes $P<0.05$ for groups separated by bar. (FIGS. 3C and 3D) Effects on cell growth. Three day growth assays were performed. Data are the number of viable cells, expressed as % of control (N=3 replicates); *$P<0.05$ compared to control. (FIG. 3E) Effects on AR activation. Western blots of nuclear (N) and cytoplasmic (C) preparations of cell extracts were probed for AR, laminin 1 or α-tubulin. (FIGS. 3F and 3G) Effects on tumor outgrowth after androgen deprivation therapy. LNCaP/AR-luc cells were implanted subcutaneously (N=6 mice/cohort) or orthotopic (N=15 mice/cohort were implanted; N=5 yielded tumors) into castrate mice, treatment with KBU2046 began as noted, and weekly IVIS imaging performed. Data are tumor size, expressed as luminescence intensity. All data are expressed as mean±SEM.

Combining Anti-Motility Therapy with Therapy Directed at the Bone Microenvironment has Improved Efficacy Metastasis to the bone occurs in over 90% of people with metastatic PCa (Polascik, *Ther Clin Risk Manag* 4, 261-268 (2008)). Upon arrival to bone, PCa cells modify the environment in a manner conducive to their outgrowth engaging what is known as the "vicious cycle" (Guise, *J Musculoskelet Neuronal Interact* 2, 570-572 (2002); Guise et al., *Endocr Rev* 19, 18-54 (1998); and C. Logothetis et al., *Cancer Metastasis Rev* 37, 189-196 (2018)). Specifically, PCa cells secrete interleukin (IL)-11 and parathyroid hormone-related protein (PTHrP), stimulating osteoblasts to secrete receptor activator of nuclear factor kappa-B ligand (RANKL), RANKL induces osteoclasts to degrade bone, degradation of bone matrix releases insulin growth factor (IGF) and transforming growth factor (TGF)β, which act to sustain PCa cell growth. We previously demonstrated that KBU2046 inhibits cell motility by inhibiting activation of Raf1, specifically, by inhibiting phosphorylation of its $Ser^{338}$ activation motif (Xu et al., *Nature Communications* 9, 2454 (2018)). A central function of Raf1 relates to regulating reorganization of the actin cytoskeleton, which in turn affects how cells interact with and move through the microenvironment (Yotova et al., *J Cell Mol Med* 16, 2127-2139 (2012)). Cytoskeleton reorganization is required for osteoclasts to successively move across and to bind bone matrix, doing so by arranging their actin cytoskeleton to form a low pH resorptive cavity in which degradation of bone mineral occurs (Florencio-Silva et al., *Biomed Res Int* 2015, 421746 (2015)). These facts led us to consider that osteoclast-mediated bone degradation was dependent upon cytoskeleton reorganization, and therefore might be inhibited by KBU2046.

To examine this paradigm we first evaluated whether KBU2046 would inhibit Raf1 phosphorylation in osteoclasts. After treatment with RANKL, RAW 267.4 cells differentiate into mature osteoclasts. Upon maturation osteoclast become multinucleated, express tartrate resistant acid phosphatase (TRAP), and have the capacity to form actin rings that create an occluded cavity in which bone is degraded. KBU2046 inhibits phosphorylation of Raf1's activation motif in RANKL treated RAW 267.4 osteoclast cells, and does so in a time-dependent manner (FIG. 4A). In osteoclasts Raf1 is known to phosphorylate MEK1/2, in turn phosphorylating ERK1/2 (Bradley et al., *J Cell Biochem* 104, 1439-1451 (2008)), with the latter acting to stimulate osteoclast differentiation and bone resorptive activity (He et al., *PLoS One* 6, e24780 (2011); and Nakamura et al., *J Bone Miner Res* 18, 1198-1205 (2003)). The functional relevance of KBU2046 -mediated inhibition of Raf1 phosphorylation is shown by demonstrating inhibition of MEK1/2 and ERK1/2 phosphorylation. Osteoclasts in FIG. 4A were not cultured on bone mineral, demonstrating that KBU2046-mediated inhibition of Raf1 phosphorylation is not dependent upon the presence of bone mineral.

Treatment of RAW 267.4 cells with KBU2046 induces several structural and functional changes. It reduces RANKL-mediated formation of multinucleated cells, and those that do form have lower numbers of nuclei (see 40× panels, FIG. 4B). The characteristic prominent actin ring (white arrow) surrounding the resorptive cavity (yellow arrow) is readily apparent in control cells treated with RANKL ligand, but is lacking in KBU2046-treated cells (100×, panels). Consistent with it inhibiting maturation of RAW 267.4 cells, TRAP staining is decreased in KBU2046-treated cells (FIG. 4C). In the absence of RANKL, undifferentiated RAW 267.4 cells exhibit a phenotype characterized by isolated cells with long thin cytoplasmic extensions (FIG. 4B). However, treatment with KBU2046 markedly reduces cellular extensions, demonstrating that its ability to induce effects on RAW 267.4 cells is not RANKL dependent.

FIGS. 4A-4D represents the KBU2046 inhibition of osteoclast function. FIG. 4A compares effects on Raf1 activation. RAW 267.4 cells were treated with RANKL for 4 days, treated with 10 μM KBU2046 for the indicated time periods, and Western blot for the denoted proteins performed. (FIG. 4B) Effects on cell morphology. RAW 267.4 cells were treated with RANKL and with KBU2046 for 4 days, or not, and denoted, and stained for actin (green) and DAPI (blue); white arrow denotes an actin ring, yellow arrow a resorptive cavity. Representative immunofluorescent images are depicted. (FIG. 4C) Tartrate resistant acid phosphatase (TRAP) expression. Cells were treated as in B, stained for TRAP (denoted by presence of red), and representative images from light microscopy depicted. (FIG. 4D) Bone degradation. RAW 267.4 cells were plated onto Osteo Assay plates, treated with RANKL for 6 days and with KBU2046 (or vehicle for controls) as indicated and bone surface area quantified. Data are the mean±SEM (N=3 replicates) of bone surface area, expressed as the percentage of control cells; *denotes $P<0.05$ compared to control.

To determine whether KBU2046 inhibits osteoclast-mediated bone degradation, we used Corning Osteo Assay Surface plates, which are coated with calcium-phosphate-based bone mineral. This platform supports osteoclast growth, allowing for the quantitative measurement of bone degradation, and has previously been used to measure bisphosphonate-mediated inhibition of bone degradation (40). RAW 267.4 cells were grown on Osteo Assay plates in the presence of RANKL, treated with KBU2046 at 1 μmol/L, 10 μmol/L, or with vehicle (control), and effects on bone destruction quantified after 6 days. In this manner we demonstrated that when 10 μmol/L KBU2046 is present, it significantly increased bone surface area by 28%±1.4% (mean±SEM) compared with control ($P<0.05$; FIG. 4D). To further substantiate the role of Raf1, we demonstrated that each of the Raf1-specific inhibitors, ZM336372, GW5074, and NVP-BHG712, inhibit osteoclast-mediated bone degradation, as well as RANKL-induced osteoclast maturation. The latter is demonstrated by decreased TRAP staining, decreased formation of multinucleated cells, and inhibition of resorptive cavity formation. Together, these findings demonstrate that we can inhibit degradation of bone matrix through an innovative strategy targeting Raf1.

We next examined targeting of the bone microenvironment coupled to targeting cell motility. Bisphosphonates modify the bone microenvironment by chemically binding to calcium-phosphate bone mineral, are then taken up by osteoclasts after they digest the bound mineral and once inside the cell, they inhibit osteoclast-mediated bone degradation (Polascik et al., *Ther Clin Risk Manag* 4, 261-268 (2008)). The bisphosphonate, zoledronic acid (ZA), is used clinically to decrease bone fractures in men with metastatic PCa (Saad et al., *J Natl Cancer Inst* 94, 1458-1468 (2002); Saad et al., *J Natl Cancer Inst* 96, 879-882 (2004); and James et al., *JAMA Oncol* 2, 493-499 (2016)). ZA is administered to humans by injection, whereupon it binds to bone mineral, while the remainder is rapidly cleared from the body, and that bound to bone mineral is responsible for inhibition of osteoclast activity and resultant decrease in bone fractures in men with metastatic PCa (N. Pharmaceuticals, Zoledronic Acid package insert FDA approved drug package insert, (2007)). We therefore focused our investigations upon ZA. Further, we emulated the pharmacologic situation in humans by pre-treating Osteo Assay plates with ZA, washing non-bound ZA away prior to adding RAW 267.4 cells, then treated, or not, with KBU2046, and measured resultant effects upon bone degradation. ZA was evaluated at 2, 10 and 20 μM, demonstrating a concentration dependent increase in bone surface area, all significant compared to control ($P<0.05$) (FIGS. 5A and 5B). KBU2046 similarly significantly increased bone surface area ($P<0.05$). Importantly, the combination of ZA+KBU2046 yielded significantly improved efficacy compared to either agent alone ($P<0.05$), did so with all ZA concentrations tested, and with the combination of 20 μM ZA+KBU2046 bone surface area increased to 193±1.6% of control (mean±SEM). When combined with KBU2046, upon going from 10 to 20 μM ZA, there was no further improvement in efficacy, consistent with a plateau effect.

FIGS. 5A-5H represent the improved efficacy seen with KBU2046 combined with ZA. In FIG. 5A bone degradation was tested using osteo assays performed as in FIG. 4D. Cells were treated with KBU2046 (46), ZA at 2, 10 or 20 μM, with the indicated combinations, or vehicle (control; CO). Data are the mean±SEM (N=3 replicates); *denotes $P<0.05$ compared to control, or between conditions denoted by bars. FIG. 5B provides representative photomicrographs of osteo assay wells. Black color denotes presence of bone matrix; RL: RANKL. (FIGS. 5C-5E) Cell viability, cytotoxicity and apoptosis. RAW 267.4 cells were treated with RANKL, at day 4 they were treated with KBU2046, ZA at 1 or 10 μM (ZA1 or ZA10), the indicated combination, or vehicle (CO) and Triplex assay performed 24, 48 or 72 hours later, per Methods. Data are the mean±SEM (N=4 replicates); V, #, *denotes $P<0.05$ compared to control. (FIGS. 5F-5H) In vivo efficacy. Four cohorts of mice, N=15/cohort, were given intracardiac injections of PC3-luc cells, yielding the following successful injections: N=12 control, N=12 ZA, N=13 KBU2046 and N=13 ZA+KBU2046. Treatment was oral 150 mg KBU2046/kg daily (starting 3 days before IC injection), intraperitoneal ZA 100 μg/kg weekly (starting 1 week before IC injection), with oral and intraperitoneal vehicle controls given as indicated. (FIG. 5F) Representative computed tomography images. Image types are: side view and coronal sections of skull, and axil and sagittal sections of the femurs. Red arrows denote areas of bone destruction. (FIGS. 5C and 5D) Quantification of bone lesions. The macroscopic lesions in the jaw were quantified by direct measurement from CT images, and expressed as the mean±SEM percent of control. Bone density of femurs was measured from CT images, and expressed as the mean±SEM percent of control. *denotes $P<0.05$ compared to control, and for groups indicated by bars.

We next examined the effect of ZA and KBU2046 on osteoclast cell viability, apoptosis and cytotoxicity. RAW 267.4 cells were treated with RANKL for the duration of the experiment, at day 4 they were then treated with ZA, KBU2046, the combination, or vehicle (for controls), and effect on cell viability, apoptosis and cytotoxicity measured by Triplex assay at 24, 48 and 72 hours after treatment (FIGS. 5C-5E). In each of FIGS. 5C, 5D, and 5E, the sequence of bars in each of the three clusters of bars, from left to right, is control, KBU2046, ZA1, ZA10, ZA1+46, and ZA10+46.

It is important to consider that during the 7 day time course of this experiment, RAW 267.4 cells, under the influence of RANKL, are undergoing maturation to terminally differentiated osteoclasts. Findings in control cells are consistent with this process, demonstrating successive decreases in cell viability, accompanied by increases in cellular cytotoxicity and apoptosis with time. Findings with KBU2046 are consistent with it delaying the maturation process, and include significant increases in cell viability and decreases in cytotoxicity at 72 hours, compared to control ($P<0.05$). There is a notable significant increase in apoptosis in KBU2046 treated cells at 72 hours compared to controls ($P<0.05$), possibly reflecting prior findings by other investigators linking suppression of Raf1 signaling to an increase in apoptotic activity (Alejandro, J. D. Johnson, Inhibition of Raf-1 alters multiple downstream pathways to induce pancreatic beta-cell apoptosis. *J Biol Chem* 283, 2407-2417 (2008)). The combination of ZA+KBU2046 significantly increased apoptosis and cytotoxicity at 48 hours, but there was little-to-no effect on viability at 72 hours.

To evaluate the effectiveness of this strategy in vivo, we used the human PC3-luc PCa intracardiac injection model (Xu et al., *Nature Communications* 9, 2454 (2018); and Chu et al., *Mol Cancer Res* 6, 1259-1267 (2008)). In this model, mice develop widespread metastasis to the bone, with those to the mandible being the most prominent and symptomatic. Mice were treated with either ZA, KBU2046, ZA+KBU2046 or vehicle (control), and at the end of the experiment CT images of the bones were obtained and metastasis to the mandible and femur quantified (FIGS. 5F-5H). Weekly IVIS imaging demonstrated progressive tumor growth over the five weeks of the experiment in the mandible, femur and whole body, across all cohorts of mice. Representative CT images demonstrate the typically large destructive lesions in the mandible (FIG. 5F), and these were quantified by direct measurement (FIG. 5G). Metastasis to the femur were smaller, led to generalized loss of bone, with representative images demonstrating decreased density of trabecular bone and thinning of cortical bone (FIG. 5F), and were quantified by measurement of density (FIG. 5H). In the mandible, KBU2046 inhibited bone destruction by 33±4.2% ($P<0.05$) compared to control. While ZA also decreased bone destruction, this effect was not significant. Importantly, ZA did not impair KBU2046 efficacy. In the femur, bone density was significantly ($P<0.05$) improved as compared to control by 56±2.7% and 22±2.4% with ZA or KBU2046 treatment, respectively. Further, the combination of ZA+KBU2046 resulted in significant ($P<0.05$) additive efficacy compared to either standalone treatment, significantly increasing density by 76±3.7% as compared to the control treatment cohort. Together, these findings demonstrate that combined targeting of cell motility and the bone microenvironment has additive therapeutic efficacy, an effect observed across both in vitro and in vivo model systems.

Increased cell motility and resultant metastasis is the process by which the vast majority of solid tumor cancers cause death (Minn, J. Massague, in *CANCER: Principals and Practice of Oncology*, V. T. DeVita, T. S. Lawrence, S. A. Rosenberg, Eds. (Lippincott Wiliams & Wilkins, New York, 2008), pp. 135-146; and Seyfried et al., *Crit Rev Oncog* 18, 43-73 (2013)). Considering all forms of cancer, metastasis is responsible for over 90% of mortality, and for PCa it is responsible for essentially 100% (Norgaard et al., *J Urol* 184, 162-167 (2010); and Pound et al., *JAMA* 281, 1591-1597 (1999)). Despite the overwhelming importance of this process, there remains limited therapeutic options available to patients. With KBU2046 and its ability to serve as a SHAM agent, selectively inhibiting Raf1 activation, precision targeting of cell motility and resultant metastasis is now possible.

Increased cancer cell motility is a characteristic of cancer which represents a clinically relevant driver of morbidity and mortality, and constitutes an important therapeutic target that we can now access. As such, we believe it is centrally important to consider it as one of several abnormal functions. In this regard, two criteria become apparent. First, this new found therapeutic capability cannot mitigate the efficacy of established clinical agents. Second, it underscores the strategic importance of treating cancer in a manner that targets multiple functions. Such an approach constitutes multi-functional therapy. This concept should not be confused with multi-modality therapy. The latter uses multiple therapies directed at different targets and/or pathways, but which relate to a similar set of cellular functions, such as growth and or viability.

We herein demonstrate for the first time that anti-motility therapy can be deployed in a combined non-interfering manner with multiple classes of agents previously established to have efficacy in humans. Specifically, we demonstrate sustained efficacy in conjunction with several differentially acting cytotoxic chemotherapeutic agents, and do so in cell culture based studies as well as in two murine models, one utilizing subcutaneous and one utilizing orthotopic implantation. In the case of ZA, an agent that modifies the bone microenvironment, we also demonstrate that anti-motility therapy does not interfere with its activity. If fact we demonstrate that it enhances it. Here too, experiments spanned cell culture based and human murine xenograft based models of bone destruction. Additionally, we demonstrated that anti-motility therapy does not interfere with therapies that target the androgen axis. Again, studies involved cell culture models, as well as murine models of subcutaneous and orthotopic implantation. Studies were performed in the context of androgen deprivation therapy and androgen receptor antagonist therapy, examining the effects upon cell and tumor growth, androgen-responsive gene activation and androgen receptor activation. Finally, it is important to consider that these findings taken together serve to provide additional evidence of the selective nature of KBU2046 and its mechanism of action.

After demonstrating that anti-motility therapy did not inhibit the efficacy of established therapy, we went on to demonstrate its applicability in the context of multi-functional therapy. Specifically, we demonstrated that the combination of docetaxel+KBU2046 not only retained the growth inhibitory efficacy of docetaxel but also exhibited additive efficacy at inhibiting metastasis. Docetaxel is a cytotoxic chemotherapeutic agent that inhibits cell growth and induces cell death through apoptosis, and is widely used across several cancer types inclusive of PCa. Such a strategic approach would be applicable to existing clinical scenarios where docetaxel is used to treat PCa, especially in the newly diagnosed metastatic setting, where the combination would serve to decrease formation of secondary metastasis. Because robust pre-clinical systemic models of the formation of metastasis as a function of targeting the androgen axis are lacking, we have not demonstrated that KBU2046 would provide additive antimetastatic efficacy when combined with hormone therapy. However, existing data supports that the use of KBU2046 along with hormone therapy would further decrease the development of metastasis. Specifically, we have previously demonstrated that KBU2046 will inhibit the motility of androgen-responsive PCa cell lines (Xu et al, above). Further, KBU2046 did not interfere with AR antagonist therapy mediated by enzalutamide, a widely used agent shown to decrease metastasis in humans (Hussain et al., *N Engl J Med* 378, 2465-2474 (2018)).

We also demonstrated that anti-motility therapy can enhance the efficacy of bone microenvironment targeting agents such as ZA. Osteoclasts modify the bone microenvironment in manner that requires them to interface with the bone mineral surface and to reorganize their actin cytoskeleton in order to form a chamber whose function is to degrade bone. Given that Raf1 is a known regulator of this process (Bradley et al., *J Cell Biochem* 104, 1439-1451 (2008); He et al., *PLoS One* 6, e24780 (2011); and Nakamura et al., *J Bone Miner Res* 18, 1198-1205 (2003)), we hypothesized that KBU2046 mediated inhibition of Raf1 phosphorylation on its activation motif would inhibit actin reorganization and as a result inhibit bone degradation. We demonstrated that this was the case, and did so evaluating bone degradation in vitro and with animal models of bone destruction. These findings represent a new mechanism and new strategic approach to inhibiting osteoclast function and bone destruction, and has wide spread implications.

Given that KBU2046 affects osteoclast motility and that ZA effects the bone microenvironment, i.e., separate but complementary mechanisms, we hypothesized that together they would have at least additive therapeutic efficacy at inhibiting osteoclast-mediated bone destruction. Our findings directly supported this concept. Specifically, our in vitro model system of osteoclast-mediated bone destruction demonstrated additive effects of the two agents over a spectrum of ZA concentrations. A combined targeting approach was also supported by our findings with the murine model of human PCa mediated bone destruction, where we observed two forms of additive efficacy. In the femur, the combination of both agents gave additional efficacy when compared to either agent alone. The other form of additive efficacy relates to anatomic site. In the mandible, KBU2046 exhibited high efficacy whereas ZA exhibited none. In the femur, ZA was highly efficacious, and while KBU2046 was also efficacious, it was much less than ZA. It will be important in future studies to understand the mechanistic underpinnings of these anatomic differences in agent efficacy. It is interesting to note that the use of ZA is associated with osteonecrosis of the jaw in humans. While the biology of this is poorly understood, and pre-clinical models are currently lacking, current findings support the speculation that ZA's inability to provide protection in the jaw. Given that co-administration of KBU2046 and ZA leads to additive efficacy even at low ZA concentrations and that each agent elicits site specific effects, a multi-functional therapy approach may provide a platform to scale back ZA dosing, minimizing the potential for osteonecrosis while retaining protection against bone related events.

In summary, we demonstrated that a novel anti-motility agent, bisphosphonate-linked-KBU2046, can effectively be combined with other targeted functional therapies for cancer. Such an approach addresses the paradigm of cancer arising from a relatively wide set of dysfunctions that together constitute characteristics of cancer. Such an approach is associated with improved efficacy across several clinically relevant models, and together support the translation of this approach into human studies.

Materials and Methods

Experimental Design

These investigations were designed to determine whether treating cancer with targeted multi-functional therapy, involving inhibition of cell motility, provided added therapeutic efficacy compared to existing therapies that targeted different cancer-relevant functions. Cell motility was inhibited with KBU2046, cell growth and viability were inhibited with several types of cytotoxic chemotherapy agents, including docetaxel, taxol, vinblastine and Adriamycin, or with hormone therapy, including androgen deprivation or enzalutamide, and the bone microenvironment was modified with zoledronic acid. The effects of combining KBU2046 and individual chemotherapy agents on cell growth were measured by cell growth inhibition assays performed on a panel of human cancer cell lines. The effects upon tumor growth were measured in athymic mice given PC3-M cells subcutaneous implants. The effects upon tumor growth and formation of metastasis were measured in athymic mice given orthotopic implants of PC3-M cells, and measuring primary tumor growth and quantifying metastasis to the lungs. The effects of hormone therapy on cell growth and PSA expression were measured on LNCaP or VCaP cells grown in vitro, while effects on tumor growth evaluated LNCaP-AR cells implanted either subcutaneously or orthotopically. The ability of KBU2046 and ZA to inhibit bone destruction was measured by adding osteoclasts to Osteo-Assay plates, and measuring pit formation. Inhibition of bone destruction in athymic mice was measured by CT scan of animals after intracardiac injection of PC3 cells. Inhibition of Raf1 phosphorylation in osteoclasts was measured by Western blot, while changes in the actin cytoskeleton and cell morphology were measured by immunofluorescent microscopy.

Cells Culture and Reagents

The following prostate cancer cells lines, PC-3, LNCaP, and VCaP were obtained from American Type Culture Collection, the constitutively active luciferase expressing PC3-Luc cell line was obtained from PerkinElmer, the origin a characteristics of PC3-M cells have been previously described by us (Liu et al., *Prostate cancer and prostatic diseases* 4, 81-91 (2001)). The constitutively active luciferase expressing PC3-M-luc cell line was established by transducing the parental cell line with pGL4.50 luciferase reporter (Promega), and culturing under hygromycin selection for stable integration. The LNCaP/AR-luc cell line was kindly provided by Charles Sawyers (Tran et al, *Science* 324, 787-790 (2009)).

The osteoclasts precursor mouse macrophage cell line Raw 264.7 was obtained from American Type Culture Collection. All cells were cultured as previously described (Xu et al. above; Liu et al., *Prostate cancer and prostatic diseases* 4, 81-91 (2001); and Korenchuk et al., In Vivo 15, 163-168 (2001)), were maintained at 37° C. in a humidified atmosphere of 5% carbon dioxide with biweekly media changes. All cell lines were drawn from stored stock cells, and replenished on a standardized periodic basis and were routinely monitored for *Mycoplasma* (PlasmoTest™, InvivoGen, San Diego, CA). Cells were authenticated by the following: they were acquired from the originator of that line, grown under quarantine conditions, expanded and stored as primary stocks and not used until following conditions were met: *mycoplasma* negative; through morphologic examination; growth characteristics; hormone responsiveness or lack thereof. KBU2046 was synthesized as previously described (5). Enzalutamide (#S1250), docetaxel (#S1148) and zoledronic acid (#S1314) were purchased from Selleckchem, and reconstituted per the manufacturer's recommendations.

Cytotoxicity Assays and Colony Formation Assays

To assess the impact of cytotoxic chemotherapy on PCa growth kinetics seven-day soft agar colony formation assays and three-day MTT cell growth inhibition assays were performed as described by us (Pavese et al., *Cancer Lett* 352, 179-186 (2014)). MTT assays were in replicates of N=3, and were repeated, soft agar assays were in replicates of N=2 and are presented as mean number of colonies, expressed as percent of untreated controls.

Reverse Transcription and Quantitative PCR Analysis

RNA was isolated and qRT/PCR performed as previously described by us (Ding et al., *J Biomol Tech* 18, 321-330 (2007)). Resultant data were analyzed using the $2^{-\Delta\Delta Ct}$ method (Livak et al., *Methods* 25, 402-408 (2001)), normalized to GAPDH, for the following primer/probe sets (ABI) PSA (Hs02576345_ml) and GAPDH (Hs99999905_m1). Assays were performed in triplicate, and were repeated.

Enzalutamide Mediated Cell Growth Inhibition Assays

Enzalutamide mediated growth inhibition was assessed using Sulforhodamine B (SRB) growth inhibition assays, were performed as previously described (49). In brief, LNCaP and VcaP cells were pre-incubated in charcoal-striped medium for 48 hours and then seeded ($1.9\times10^4$) in 96-well plates. Cells were stimulated with 1.0 nM R1881 and treated for 72-hours with 10 μM KBU2046 or vehicle control in the presence or absence of 10 μM enzalutamide, and subsequently SRB assays were performed. Assays were in replicates of N=6, and were repeated.

Subcellular Localization of Androgen Receptor

LNCaP and VcaP cells were pre-incubated in the charcoal-striped medium containing 10 μM KBU2046 or vehicle control for 72 hours. Cells were then stimulated with 1.0 nM R1881 and treated for 24-hours with 10 μM KBU2046 or vehicle control in the presence or absence of 10 μM enzalutamide. The nuclear and cytosolic subcellular fractions of the cells were prepared using the NE-PER Nuclear and Cytoplasmic Extraction Kit (Pierce, Waltham, MA) according to the manufacturer's instructions. Protein was quantified by BCA assay (Thermo-Fisher Scientific, Waltham, MA), per manufacturer's instructions.

Western Blot Analysis

Western blots were performed as described by us (Xu et al., *Nature Communications* 9, 2454 (2018); and Pavese et al., *Cancer Lett* 352, 179-186 (2014)). All Western blots were repeated at least once. Antibodies recognizing Androgen receptor (#5153S), Lamin B1 (#13435), and α-Tubulin (#3873) 43hosphor-c-RAF (ser338) (#9427), c-Raf (#53745), MEK ½ (#12671), 43hosphor-MEK ½ (#9121), ERK % (#4695), 43hosphor-ERK ½ (#4370), GAPDH (#2118), antimouse IgG-HRP linked secondary (#7076), and anti-rabbit IgG-HRP linked secondary (#7074) antibodies were purchased from Cell Signaling Technology. Pierce ECL western blotting substrate (#32106) and SuperSignal West Femto maximum sensitivity substrate (#34096) were purchased from Thermo Scientific. All primary antibodies were used at a dilution of 1:1000 and corresponding secondary antibodies used at a dilution of 1:5000.

Immunofluorescence

Dylight™ Phalloidin (#12935) was purchased from Cell Signaling Technology.

Raw 264.7 cells were grown in differentiation medium (described below), with or without KBU2046, for 4 days on a Chamber Slide (Nunc Lab-Tek). Chambers were washed once with PBS, followed by 10-minute fixation in cold 10% neutral-buffered formalin (VWR) and a post-fixation wash with PBS. Permeabilization was achieved with incubation in 0.1% Triton X-100 (Sigma) for 5 minutes, and then blocked overnight at 4° C. with 1% BSA (Sigma) containing 10% goat serum (Thermo Fisher Scientific), 0.3 mol/L glycine (Sigma), and 0.1% PBS-Tween20. The cells were then incubated for 2 hours at 4° C. in Dylight Phalloidin (Cell Signaling technology, #12935) antibody diluted 1:40 in 1×PBS with 1% BSA and 0.3% Triton X-100. Subsequently, the slide was washed once with PBS, a coverslip mounted with ProLong Gold Antifade Reagent with DAPI (Cell Signaling Technology, #8961), and imaged on a Confocal Microscope (Nikon/Yokogawa Spinning Disc).

Pit Formation Assays

Low passage (p≤4) RAW 264.7 cells were suspended in osteoclasts differentiation media (MEM-alpha (Gibco) with 10% FBS, 1% antibiotic-antimycotic and 50 ng/ml RANKL (EMD Millipore, R0525-10UG)) and plated in 96 well Osteo Surface Assay plates (Corning) at 5000 cells per well. For wells receiving ZA treatment, the osteosurface was pre-coated for 30 minutes at 25° C. with a 0, 2, 10, or 20 μM solution of ZA suspended in sterile water, followed by a gentle rinsing in PBS to remove free compound prior to plating of cells. Cells were treated with 10 μM KBU2046 or control for seven days with the media and treatment refreshed on day 4. On day 7, the wells were washed with PBS, and cellular material removed by a 5 min incubation in a 10% bleach solution followed by a through rinsing with Ultrapure water. To visualize the resultant osteoclast mediated pit formation, the intact mineralized matrix was stained following the manufacture's recommendations (Corning) utilizing a modified Von Kossa staining protocol. The resultant stained surfaces were imaged and subsequently evaluated using the "BoneJ" plugin of ImageJ. All treatments were performed in replicate of N=3, and were repeated.

ApoTox-Glo Assay

The ApoTox-Glo triplex assay (Promega) was performed to assess cell viability, cytotoxicity, and caspase-3/7 activation, per manufacturer's instructions. In brief, 5000 Raw 264.7 cells were plated in 96-well assay plates and cultured in the osteoclast differentiation media for four days at which point the media was replenished with or without KBU2046 and cell responses measured after 24, 48, and 72 hrs following the manufactures protocol.

Animal Models of Systemic Effects and Metastasis

All animal studies adhered to the NIH Guide for the Care and Use of Laboratory Animals, were treated under institutional IACUC-approved protocols by Oregon Health and Sciences University, complied with all federal, state, and local ethical regulations, and their design and implementation followed sanctioned guidelines (Hollingshead, Antitumor efficacy testing in rodents. *J Natl Cancer Inst* 100, 1500-1510 (2008)). Animals were housed in barrier (for immunocompromised mice) facilities, with a 12-h light/dark cycle and given soy-free food and water ad libitum. Animal study sample size determination: sample sizes were determined using the samples size estimation formula for differences in means with power set 80%, two-sided $\alpha=0.05$, and a pre-specified effect size of 30%.

PCa subcutaneous implantation: $2.5\times10^5$ PC3-M cells in sterile PBS were implanted into the right flank of 6-7 week old male athymic nude mice (Charles River) and tumor growth measurements were performed twice a week as previously described by us (Gordon et al., Chemotherapy-induced monoamine oxidase expression in prostate carcinoma functions as a cytoprotective resistance enzyme and associates with clinical outcomes. *PLoS One* 9, e104271 (2014)). Treatment via oral gavage 5 days per week with 80 mg/kg KBU2046 or vehicle control (sesame oil), as well as weekly intraperitoneal injections (IP) of docetaxel (0, 20 mg/kg) began 18 days post implantation when tumors reached our enrollment criteria of ~200-300 $mm^3$. Experimental groups were randomly assigned to cages prior to the initiation of the study. Tumor measurements were obtained in a blinded fashion, and tumor volumes were calculated with the following formula: $length\times(width)^2\times0.5$.

PCa orthotopic implantation: Orthotopic implantation of $2.5\times10^5$ PC3M-luc into 7-8 week old male athymic mice was performed as previously described by us (5, 52 Xu et al., above; and Pavese et al., *J Vis Exp, e*50873 (2013)). Daily oral gavage treatment with 150 mg/kg KBU2046 or was initiated 3 days prior to implantation and continued throughout the duration of the study. Weekly IP injections with 7.5 mg/kg docetaxel or control were administered beginning one week post implantation. Primary tumor out growth was monitored via weekly IVIS imaging. At the completion of the study the primary tumor was resected and weighed and lungs were resected and snap frozen. To determine the human PCa metastatic burden in each mouse lung, the snap frozen tissue was pulverized, DNA isolated and Alu-sequencing performed as previously described (19). The following custom TaqMan primer probe set was utilized: forward primer (101 F) GGTGAAACCCCGTCTCTACT (SEQ ID NO: 1), reverse primer (206 R) GGTTCAAGCGATTCT CCTGC (SEQ ID NO: 2), and hydrolysis probe (144RH) CGCCCGGCTAATTTTTGTAT (SEQ ID NO: 3). The 144RH probe was labeled with a 5' fluorescent reporter (6-FAM) and a 3' fluorescent quencher (Black Hole Quencher). The relative content of human DNA was calculated with using the comparative $C_T$ method, $C_T$ (sample)−$C_T$(negative control). All samples were run in triplicate and were repeated.

Castration resistant PCa subcutaneous implantation: 6-7 week old male athymic mice received trans-scrotal bilateral orchiectomy with a single incision in the midline of scrotums under general anesthesia and then allowed to recover for 10 days. Following the recovery period mice received a subcutaneous implantation of $2.0\times10^6$ LNCaP/AR-luc into the right flank as previously described by us (Gordon et al., *PLoS One* 9, e104271 (2014)). Treatment with 80 mg/kg KBU2046 or control was administered via oral gavage 5 times weekly starting 4 weeks post-implantation, prior to the emergence of the castration resistant phenotype, and continued for 12 weeks. Experimental groups were randomized prior to the initiation of treatment. Twice weekly tumor measurements were performed and androgen receptor activity monitored biweekly through IVIS imaging.

Castration resistant PCa orthotopic implantation: Castrations of athymic mice were performed as described above, and following a two-week recovery period orthotopic implantations of $5.0\times10^5$ LNCaP/AR-luc were performed as previously described by us (Xu et al., above; and, Pavese et al., above). Biweekly IVIS imaging was performed to assess androgen receptor activity and treatment with 80 mg/kg KBU2046 or control via oral gavage 5 times weekly began 12 weeks post-implantation, as the castration resistant phenotype began to emerge, and continued for duration of 4 weeks. Experimental groups were randomly assigned to cages prior to the initiation of the study.

PCa intracardiac (IC) injection: IC injection of $4.0\times10^5$ PC3-luc cells into the left ventricle of 7-8 week old athymic mice under ultrasound guidance was performed as previously described by us (Xu et al., above). Weekly IP injections of 100 μg/kg ZA or vehicle control (PBS) began 7 days prior to the IC injection and continued throughout the duration of the study, whereas daily oral gavage treatment with 150 mg/kg KBU2046 or control began 3 days prior to the IC injection. All treatments were randomly assigned to cages prior to the initiation of the study. IVIS imaging was performed 30 min post IC injection to confirm systemic distribution of cells and conducted weekly starting 7 days post injection, continuing for a period of 4 weeks. Animals were excluded from the analysis if 30-minute post-injection IVIS imaging revealed a focal signal only in the chest indicating a failed injection where cells were not distributed into circulation. Computed Tomograpgy (CT) radiographic imaging of the entire cohort was performed with an Inveon X-ray μCT scanner (Inveon, Siemens) at the completion of the study. Resultant images were analyzed in a blinded fashion using Inveon Research Workplace 4.2 visualization/analysis software and ImageJ. Specifically, to assess metastasis-associated bone destruction, images were exported from the Inveon workplace in the Digital Imaging and Communications in Medicine (DICOM) format for analysis in ImageJ. Each imported image was adjusted to a common brightness/contrast threshold and the "Stack→Crop (3D)" and "volume viewer" plugins were utilized to perform multiplanar reconstruction (MPR) of regions of interest (mandible and femurs). Utilizing the MPR of the bilateral femurs, a blinded operator obtained step-section serial images of trabecular bone at both the proximal and distal ends of each femur. Subsequently, the "ROI manager" plugin was utilized to specify fixed regions of interest (ROIs) in each step-section images, and from which measurement bone density were obtained. Bone disruption of the mandible was assessed in a blinded fashion utilizing the MPR of the mandible. Here, the loss of bone in the periodontal cavity was calculated by measuring the distance between the edge of molar root and the wall of periodontal cavity at both coronal and transverse planes.

Statistical Analysis

For all experiments unless otherwise stated, comparisons between two groups were evaluated with the two-sided Student's t-test of fisher's exact test using a significance threshold of $P \leq 0.05$. Some experiments, as denoted, used Fisher exact test using a significance threshold of $P \leq 0.05$. In such instances, the mean value of the control group was used as the threshold to assign the categorical nature (i.e., >/=versus<the mean value) of individual outcomes within different treatment groups.

FIGS. 6A through 6L: Experimental compounds inhibit osteoclast mediated bone degradation.

RAW 267.4 cells were plated onto Osteo Assay plates, in differentiation medium containing RANKL and the experimental compounds (or vehicle control) at the concentration indicated on day 0, medium was replenished with RANKL and treatments on day 3 day of the assay. To visualize the resultant osteoclast mediated pit formation, on day 6 wells were washed, cellular material removed, intact mineralized matrix was stained with a Von Kossa staining protocol, and images captured. Bone surface area was quantified, data are the mean±SEM (N=2 replicates) of the remaining bone surface area, expressed as the percentage of control cells; *denotes P<0.05 compared to control. Note: Black color denotes intact bone matrix.

FIG. 7: Experimental compound inhibits PCa cell motility.

PC3M cells were plated with the indicated concentration of Compound E at day 0 and allowed to grow to confluency (48 hrs), at which point a scratch wound was performed, wells were rinsed with PBS, media with treatment replenished, and images obtained at 0 hr and 20 post scratch. Data are N=24. * denotes P<0.05, as measured by t-test.

FIGS. 8A and 8B: Experimental compounds inhibit movement of human prostate cancer cells.

PC3 cells were treated with 10 micromolar of compound E ($n_1$=1) for a total of 72 hrs, and placed into the upper well of uncoated (for migration) or collagen I coated (for invasion) Boyden chambers for the last 36 hours, and the number of cells in the lower chamber counted. Data are the mean+/−SEM, N=4 replicates, expressed as % control cells.

FIG. 9: Experimental compounds do not inhibit human prostate cancer cell viability.

Equal numbers of PC3 cells were plated under conditions permitting exponential cell growth, and one day later they were treated with 10 micromolar of compound E ($n_1$=1) for a total of 72 hrs, and cell viability measured using the ApoTox-Glo™ Triplex assay (Promega). Data are the mean+/−SEM, N=4 replicates, expressed as relative fluorescent units.

FIG. 10: Experimental compounds do not inhibit the viability of osteoclasts.

Equal numbers of RAW 267.4 cells were plated under conditions permitting exponential cell growth, and one day later they were treated with RANKL (to stimulate differentiation into mature osteoclasts) and treated with 10 micromolar of compound E ($n_1$=1) for a total of 72 hrs, and cell viability measured using the ApoTox-Glo™ Triplex assay (Promega). Data are the mean+/−SEM, N=4 replicates, expressed as relative fluorescent units.

FIGS. 11A and 11B: Compound E ($n_1$=1) inhibits bone destruction.

Mice were treated with 0 (vehicle only), 10, 100 or 1000 μg/kg compound E ($n_1$=1) by weekly intraperitoneal injection, beginning 1 week before intracardiac (IC) injection of PC3-luc cells (PC3 cells that express luciferase). IVIS imaging was performed weekly, and at the end of the experiment, computed tomography (CT) scans performed and the degree of bone destruction in the jaw quantified. A total of N=10 control mice (given vehicle only) were injected, and for each of the treatment cohorts, N=10 mice were injected. * denotes P</=0.05 by 2-sided Student's t test for comparisons between cohorts indicated by bars.

FIG. 12: Compound E ($n_1$=1) prolongs survival.

Mice were from FIG. 5, and were treated with 0 (vehicle only), 10, 100 or 1000 μg/kg compound E ($n_1$=1) by weekly intraperitoneal injection, beginning 1 week before intracardiac (IC) injection of PC3-luc cells. Data depict survival of N=10 mice per cohort, expressed as the percentage of mice at the beginning of the experiment (i.e., the day of IC injection).

FIGS. 13-18: KBU2046 does not inhibit the efficacy of chemotherapy

For PC3-M PCa and MDA-MB-231 triple negative breast cancer cells, data are the mean±SD (N=2 replicates) number of colonies in 7 day colony formation assays. All data are expressed as the percentage of untreated control cells. Cells were treated with 10 μM KBU2046 or vehicle (CO), and the indicated concentration and type of chemotherapy.

Definitions

The compounds of the disclosure may possess an asymmetric center, and can be produced as a racemic mixture or as individual enantiomers. The individual enantiomers may be obtained by asymmetric synthesis or by resolving a racemic or non-racemic mixture of an intermediate at some appropriate stage of the synthesis. The individual enantiomers may also be obtained by resolution of the compound by conventional means, such as crystallization in the presence of a resolving agent, or chromatography, using, for example a chiral high pressure liquid chromatography (HPLC) column. The individual enantiomers as well as racemic and non-racemic mixtures of enantiomers are within the scope of the present disclosure, all of which are intended to be included within the structures depicted in this specification unless otherwise specifically indicated.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

The terms "therapeutically effective amount" or "pharmaceutically effective amount" refer to an amount that is sufficient to effect treatment, as defined below, when administered to a subject (e.g., a mammal, such as a human) in need of such treatment. The therapeutically or pharmaceutically effective amount will vary depending upon the subject and disease condition being treated, the weight and age of the subject, the severity of the disease condition, the manner of administration and the like, which can readily be determined by one of ordinary skill in the art. For example, a "therapeutically effective amount" or a "pharmaceutically effective amount" of a compound of Formula I, or a pharmaceutically acceptable salt or co-crystal thereof, is an amount sufficient to modulate a physiological expression or activity, and thereby treat a subject (e.g., a human) suffering an indication, or to ameliorate or alleviate the existing symptoms of the indication. For example, a therapeutically or pharmaceutically effective amount may be an amount sufficient to decrease a symptom of a disease or condition responsive to inhibition of activity. In some embodiments, the pharmaceutically effective dose per administration may be from about 1 mg to about 200 mg. In other embodiments, the pharmaceutically effective dose may be from about 5 mg to about 150 mg per dose. In other embodiments, the pharmaceutically effective dose may be from about 5 mg to about 100 mg per dose. In additional embodiments, the pharmaceutically effective dose may be from about 1 mg to about 50 mg.

For the treatment of osteoporosis, a medical professional may provide the dosage in a once-weekly regimen or divide the dosage into equal daily doses. For treatment of Paget's Disease of the bone, a single or divided dose may be administered every 1, 2, 3, 4, 5, or 6 months.

"Treatment" or "treating" is an approach for obtaining beneficial or desired results including clinical results. Beneficial or desired clinical results may include one or more of the following: (i) inhibiting the disease or condition (e.g., decreasing one or more symptoms resulting from the disease or condition, and/or diminishing the extent of the disease or condition); (ii) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or (iii) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival).

The terms "inhibiting" or "inhibition" indicates a decrease, such as a significant decrease, in the baseline activity of a biological activity or process. "Inhibition of a given activity" refers to a decrease in the activity as a direct or indirect response to the presence of a compound of Formula I, or a pharmaceutically acceptable salt or co-crystal thereof, relative to the activity of the condition in the absence of such compound or a pharmaceutically acceptable salt or co-crystal thereof. The decrease in activity may be due to the direct interaction of the compound with a biological target, or due to the interaction of the compound(s) described herein with one or more other factors that in turn affect the specific activity. For example, the presence of the compound(s) may decrease an activity by directly binding to the target, by causing (directly or indirectly) another factor to decrease the activity, or by (directly or indirectly) decreasing the amount of a factor present in the cell or organism. In some embodiments, the inhibition of the specified activity may be compared in the same subject prior to treatment, or other subjects not receiving the treatment. The term "inhibitor" is understood to refer to a compound or agent that, upon administration to a human in need thereof at a pharmaceutically or therapeutically effective dose, provides the inhibition activity desired.

"Delaying" the development of a disease or condition means to defer, hinder, slow, retard, stabilize, and/or postpone development of the disease or condition. This delay can be of varying lengths of time, depending on the history of the disease or condition, and/or subject being treated. A method that "delays" development of a disease or condition is a method that reduces probability of disease or condition development in a given time frame and/or reduces the extent of the disease or condition in a given time frame, when compared to not using the method. Such comparisons are typically based on clinical studies, using a statistically significant number of subjects. Disease or condition development can be detectable using standard methods, such as routine physical exams, mammography, imaging, or biopsy. Development may also refer to disease or condition progression that may be initially undetectable and includes occurrence, recurrence, and onset.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein, including the specification, abstract, and claims, are inclusive of the recited endpoint and independently combinable (for example, the range of "from 2 to 10" is inclusive of the endpoints, 2 and 10, and all the intermediate values).

By "significant" is meant any detectable change that is statistically significant in a standard parametric test of statistical significance such as Student's T-test, where $p<0.05$.

"Pharmaceutically acceptable salts" include, for example, salts with inorganic acids and salts with an organic acid. Examples of salts may include hydrochloride, phosphate, diphosphate, hydrobromide, sulfate, sulfinate, nitrate, malate, maleate, fumarate, tartrate, succinate, citrate, acetate, lactate, methanesulfonate (mesylate), benzenesulfonate (besylate), p-toluenesulfonate (tosylate), 2-hydroxyethylsulfonate, benzoate, salicylate, stearate, and alkanoate (such as acetate, $HOOC—(CH_2)_n—COOH$ where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

The term "crystal forms" and related terms herein refer to the various crystalline modifications of a given substance, including, but not limited to, polymorphs, solvates, hydrates, co-crystals, and other molecular complexes, as well as salts, solvates of salts, hydrates of salts, other molecular complexes of salts, and polymorphs thereof. Crystal forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates, such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding and solvent-drop grinding.

The term “co-crystal” or “co-crystal salt” as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to a per se known co-crystallization method. The terms co-crystal (or cocrystal) or co-crystal salt also refer to a multicomponent system in which there exists a host API (active pharmaceutical ingredient) molecule or molecules, such as a compound of Formula I, and a guest (or co-former) molecule or molecules. In particular embodiments the pharmaceutically acceptable co-crystal of the compound of Formula I or of the compound of Formula II with a co-former molecule is in a crystalline form selected from a malonic acid co-crystal, a succinic acid co-crystal, a decanoic acid co-crystal, a salicylic acid co-crystal, a vanillic acid co-crystal, a maltol co-crystal, or a glycolic acid co-crystal. Co-crystals may have improved properties as compared to the parent form (i.e., the free molecule, zwitter ion, etc.) or a salt of the parent compound. Improved properties can include increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like.

The terms “subject” and/or “patient” refers to an animal, such as a mammal, that has been or will be the object of treatment, observation, or experiment. The methods described herein may be useful in both human therapy and veterinary applications. In some embodiments, the subject is a mammal; in some embodiments the subject is human; and in some embodiments the subject is chosen from cats and dogs. “Subject in need thereof” or “human in need thereof” refers to a subject, such as a human, who may have or is suspected to have diseases or conditions that would benefit from certain treatment; for example treatment with a compound of Formula I, or a pharmaceutically acceptable salt or co-crystal thereof, as described herein. This includes a subject who may be determined to be at risk of or susceptible to such diseases or conditions, such that treatment would prevent the disease or condition from developing.

As used herein, “pharmaceutically acceptable excipient” is a pharmaceutically acceptable vehicle that includes, without limitation, any and all carriers, solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term “carrier” refers to an excipient or vehicle that includes without limitation diluents, disintegrants, precipitation inhibitors, surfactants, glidants, binders, lubricants, and the like with which the compound is administered. Carriers are generally described herein and also in “Remington’s Pharmaceutical Sciences” by E. W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions, and the amounts of such carriers in the composition, may vary depending on the method of formulation (e.g., dry granulation formulation, solid dispersion formulation).

The term “diluent” generally refers to a substance that is used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term “disintegrant” generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term “precipitation inhibitors” generally refers to a substance that prevents or inhibits precipitation of the active agent from a supersaturated solution. One example of a precipitation inhibitor includes hydroxypropylmethylcellulose (HPMC).

The term “surfactants” generally refers to a substance that lowers the surface tension between a liquid and a solid that could improve the wetting of the active agent or improve the solubility of the active agent. Examples of surfactants include poloxamer and sodium lauryl sulfate.

The term “glidant” generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term “binder” generally refers to any pharmaceutically acceptable film which can be used to bind together the active and inert components of the carrier together to maintain cohesive and discrete portions. Examples of binders may include hydroxypropylcellulose, hydroxypropylmethylcellulose, povidone, copovidone, and ethyl cellulose.

The term “lubricant” generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

Pharmaceutical Compositions and Administration

Compounds of Formula I, or a pharmaceutically acceptable salt or co-crystal thereof, are usually administered in the form of pharmaceutical compositions. This disclosure therefore provides pharmaceutical compositions that contain, as the active ingredient, one or more of the compounds described, or a pharmaceutically acceptable salt, pharmaceutically acceptable co-crystal or pharmaceutically acceptable ester thereof, and one or more pharmaceutically acceptable vehicle, such as excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the compound of Formula I, or a pharmaceutically acceptable salt or co-crystal thereof, may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline may also conventionally be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. In some embodiments, for parenteral administration, sterile injectable solutions are prepared containing a therapeutically effective amount, e.g., 0.1 to 1000 mg, of the compound of Formula I, or a pharmaceutically acceptable salt or co-crystal thereof. In some embodiments, the effective amount will be from about 0.1 mg to about 100 mg per dose. In other embodiments, the dosage will be from about 5 mg to about 75 mg per dose. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

Oral administration is another route for administration of the compound of Formula I, or a pharmaceutically acceptable salt or co-crystal thereof. Administration may be via capsule or enteric coated tablets, or the like. In making the pharmaceutical compositions that include the compound of Formula I, or a pharmaceutically acceptable salt or co-crystal thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients in an oral formulation include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The pharmaceutical compositions as described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices (patches). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

In some embodiments, for parenteral administration, each dosage unit contains from 0.1 mg to 1 g, 0.1 mg to 700 mg, or 0.1 mg to 100 mg of a compound of Formula I, or a pharmaceutically acceptable salt or co-crystal thereof.

For any of the dosage units as described herein, it will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of the compound of Formula I, or a pharmaceutically acceptable salt or co-crystal thereof. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills as described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions comprising the compound of Formula I, or a pharmaceutically acceptable salt or co-crystal thereof, may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The compounds, pharmaceutical compositions, and methods of treatment herein may be used in combination with other forms of cancer treatment, including chemotherapy, other bone directed therapy, inclusive of bisphosphonates or denosumab, hormone therapy, radiation therapy, surgery, small molecule therapeutics (imatinib, cisplatin, doxorubicin, Ifosfamide, methotrexate, vincristine, cyclophosphamide, etoposide, dactinomycin, eribulin mesylate, larotrectinib, pazopanib, trabectedin), including inhibitors of protein kinases, interferon, mTOR inhibitors (rapamycin, temsirolimus, everolimus, ridaforolimus), PARP inhibitors (olaparib, rucaparib, niraparib, talazoparib, veliparib, pamiparib, AZD2281), biologics, including antibodies (trastuzumab, denosumab, glembatumumab, lexatumumab, cixutumumab, ipilimumab, bevacizumab, olaratumab), directed towards protein kinases or immune checkpoint regulators (PD-1 inhibitors, such as pembrolizumab, nivolumab, and cemiplimab; PD-L1 inhibitors atezolizumab, avelumab, and durvalumab), and regulators of angiogenesis (PF-4, TSP-1, angiostatin, endostatin).

For the treatment of bone cancers, including metastatic bone cancers, the compounds herein may be administered in combination treatments utilizing chemotherapeutic agents such as taxol, vinblastine, vincristine, Ifosfamide (IFEX®), doxorubicin (ADRIAMYCIN®), etoposide, methotrexate, cisplatin, dactinomycin, denosumab, and cyclophosphamide (CYTOXAN®), or combinations thereof.

For the treatment of osteoporosis and bone loss, the compounds herein may be utilized in combination therapies with additional agents, such as alendronate (FOSOMAX®), risedronate (ACTONEL®), ibandronate (BONIVA®), etidronate (DIDRONEL®), zolendronic acid (RECLAST®, ZOMETA®), denosumab (PROLIA®, XGEVA®), teriparatide (FORTEO®), abaloparatide (TYMLOS®), raloxifine (EVISTA®), teriparatide (FORTEO®), denosumab (PROLIA®), and calcitonin (MIACALCIN®, FORTICAL®), romosozumab, estrogen, conjugated estrogens (PREMARIN®), conjugated estrogens with medroxyprogesterone (PREMPRO®, PREMPHASE®), esterified estrogens (MENEST®), estradiol, estropipate, as well as calcium and calcium salt supplements.

Articles of Manufacture and Kits

Compositions (including, for example, formulations and unit dosages) comprising the compound of Formula I, or a pharmaceutically acceptable salt or co-crystal thereof, can be prepared and placed in an appropriate container, and labeled for treatment of an indicated condition. Accordingly, provided is also an article of manufacture, such as a container comprising a unit dosage form of the compound of Formula I, or a pharmaceutically acceptable salt or co-crystal thereof, and a label containing instructions for use of the compounds. In some embodiments, the article of manufacture is a container comprising a unit dosage form of the compound of Formula I, or a pharmaceutically acceptable salt or co-crystal thereof, and at least one pharmaceutically acceptable vehicle. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer of the bone. It should be understood that the active ingredient may be packaged in any material capable of improving chemical and physical stability, such as an aluminum foil bag. In some embodiments, diseases or conditions indicated on the label can include, for example, treatment of cancer of the bone which is original in origin to bone. In other embodiments, the label may be directed to treatment of a cancer that has metastasized to the bone.

Any pharmaceutical composition provided in the present disclosure may be used in the articles of manufacture, the same as if each and every composition were specifically and individually listed for use in an article of manufacture.

Also provided is a kit that includes a compound of Formula I, or a pharmaceutically acceptable salt, pharmaceutically acceptable co-crystal, pharmaceutically acceptable ester, stereoisomer, mixture of stereoisomers or tautomer thereof. Also provided is a kit that includes a compound of Formula II, or a pharmaceutically acceptable salt, pharmaceutically acceptable co-crystal, pharmaceutically acceptable ester, stereoisomer, mixture of stereoisomers or tautomer thereof. In one aspect, the kit comprises a compound of Formula I, or a pharmaceutically acceptable salt or co-crystal thereof. In a further aspect, the kit comprises a compound of Formula II, or a pharmaceutically acceptable salt or co-crystal thereof. The kit may comprise a label and/or instructions for use of the compound in the treatment of a disease or condition in a subject (e.g., human) in need thereof. In some embodiments, the disease or condition may be associated with or mediated by the intended activity.

REFERENCE TO SEQUENCE LISTING

The nucleic acid sequences described herein are shown using standard letter abbreviations, as defined in 37 C.F.R. § 1.822. A computer readable text file, entitled "2JB4268.txt (Sequence Listing.txt)" created on or about Aug. 5, 2021, with a file size of 4,096 bytes, contains the sequence listing for this application and is hereby incorporated by reference in its entirety. In the Sequence Listing:

SEQ ID NOs: 1-3 are custom TaqMan primer probes, including forward primer (101 F) GGTGAAACCCCGTCTCTACT (SEQ ID NO: 1), reverse primer (206 R) GGTTCAAGCGATTCT CCTGC (SEQ ID NO: 2), and hydrolysis probe (144RH) CGCCCGGCTAATTTTTGTAT (SEQ ID NO: 3).

What is claimed:

1. A compound of Formula (I) or a pharmaceutically acceptable salt thereof:

(I)

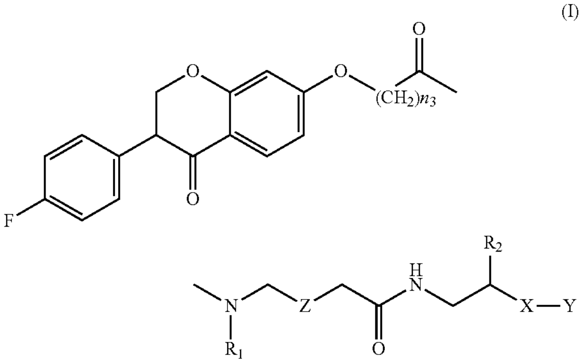

wherein:

Z is selected from the group consisting of:

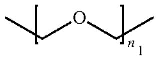 and 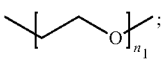;

$n_1$ in each instance is an integer selected from the group consisting of 1, 2, 3, 4, 5, and 6;

X is $(—CH_2—)_{n2}$;

$R_1$ is selected from the group consisting of H and $C_1$-$C_3$ alkyl;

$R_2$ is selected from the group consisting of H and OH;

when $R_2$ is H, $n_2$ is an integer selected from the group consisting of 0, 1, 2, and 3, and when $R_2$ is OH, $n_2$ is 1;

$n_3$ is an integer selected from the group consisting of 0 and 1;

and

Y is selected from the group consisting of

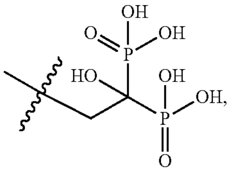

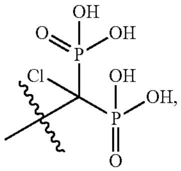

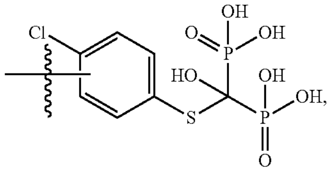

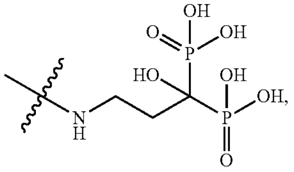

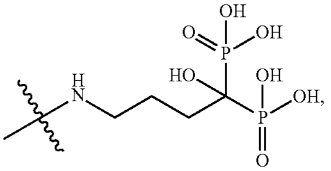

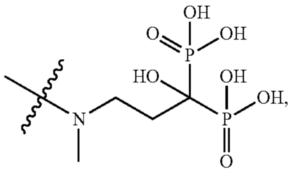

-continued

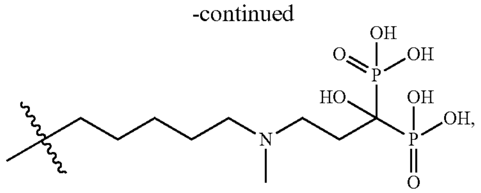

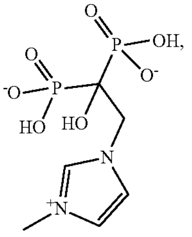

and

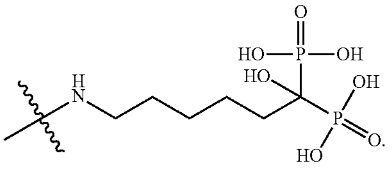

2. The compound of claim 1, or a pharmaceutically acceptable salt thereof, wherein the compound of Formula (I) is of Formula (IIa):

(IIa)

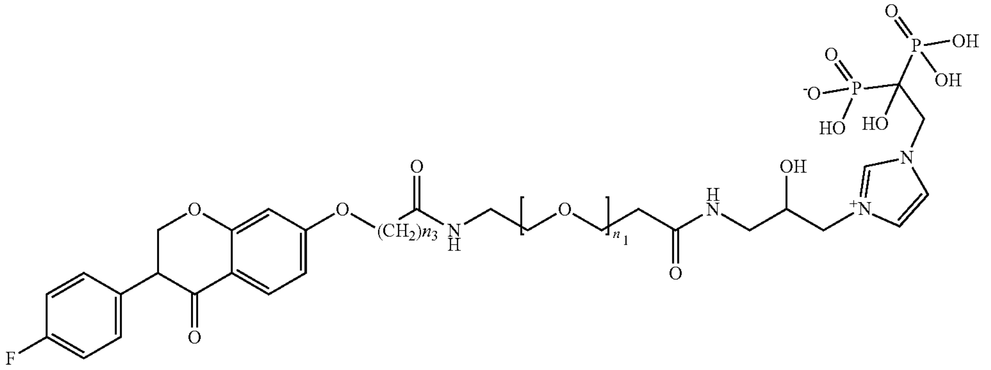

wherein:

$n_1$ is an integer selected from the group consisting of 1, 2, 3, and 4; and $n_3$ is an integer selected from the group consisting of 0 and 1.

3. The compound of claim 2, or a pharmaceutically acceptable salt thereof, having the formula:

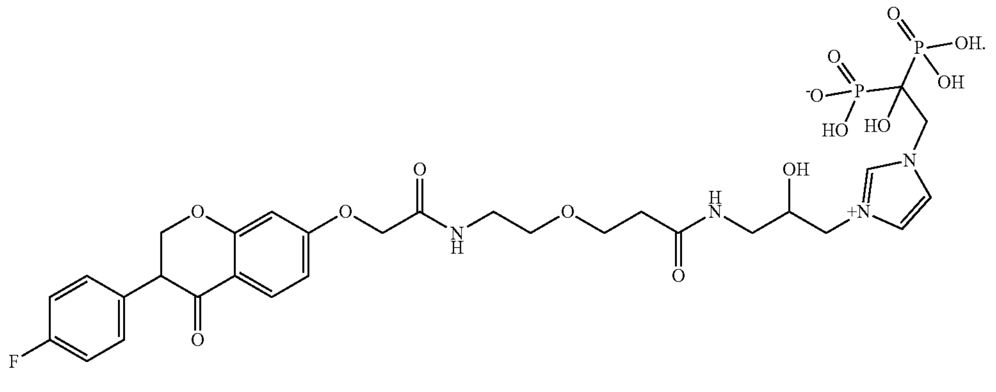
4. The compound of claim 2, or a pharmaceutically acceptable salt thereof, having the formula:
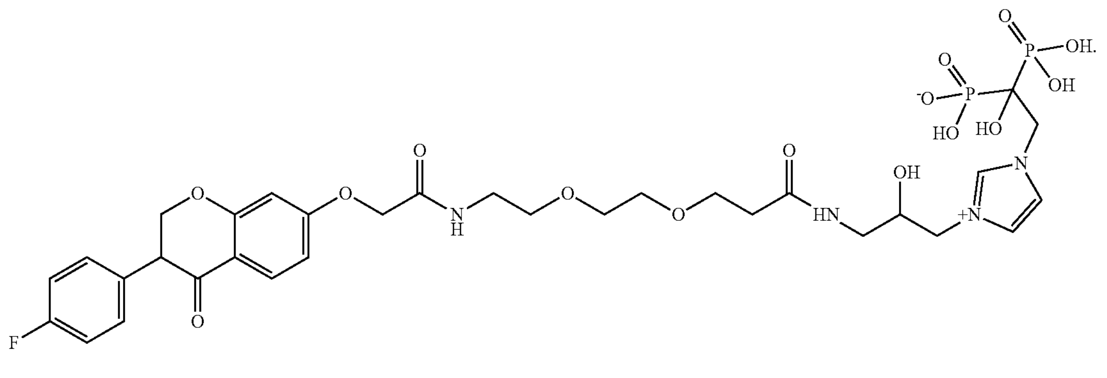
5. The compound of claim 2, or a pharmaceutically acceptable salt thereof, having the formula:
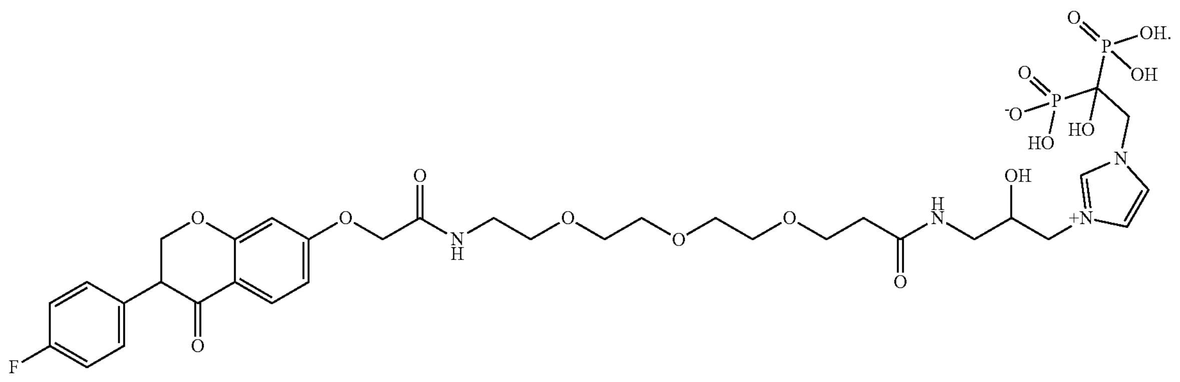
6. The compound of claim 1, or a pharmaceutically acceptable salt thereof, wherein the compound of Formula (I) is of Formula (Ib):

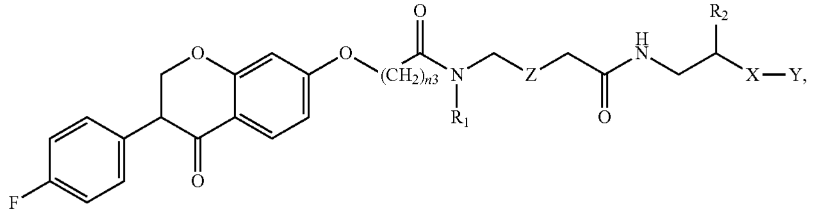

(Ib)

wherein:

Z is selected from the group consisting of:

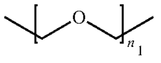 and 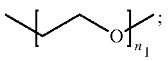;

$n_1$ is an integer selected from the group consisting of 1, 2, 3, and 4;

X is $(—CH_2—)_{n2}$;

$R_1$ is selected from the group consisting of H and $C_1$-$C_3$ alkyl;

$R_2$ is selected from the group consisting of H and OH;

when $R_2$ is H, $n_2$ is an integer selected from the group consisting of 0, 1, 2, and 3, and when $R_2$ is OH, $n_2$ is 1;

$n_3$ is an integer selected from the group consisting of 0 and 1; and

Y is as defined in claim 1.

7. The compound of claim 6, or a pharmaceutically acceptable salt thereof, wherein the compound of Formula (Ib) is of Formula (Ic):

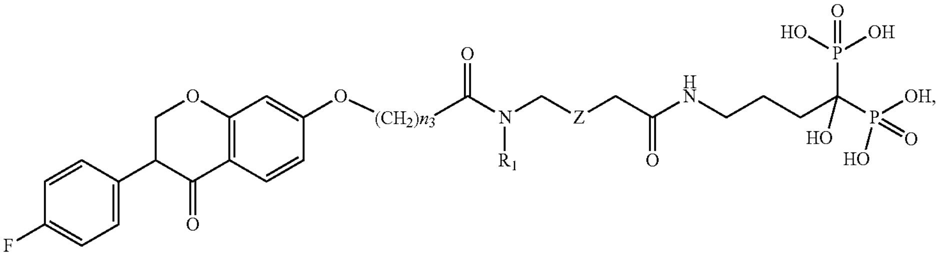

(Ic)

wherein:

$R_1$ is selected from the group consisting of H and methyl;

$n_1$ is an integer selected from the group consisting of 1, 2, and 3;

$n_3$ is an integer selected from the group consisting of 0 and 1; and

Z is selected from the group consisting of:

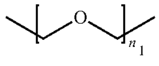 and 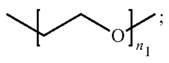;

8. The compound of claim 7, or a pharmaceutically acceptable salt thereof, wherein the compound has the formula:

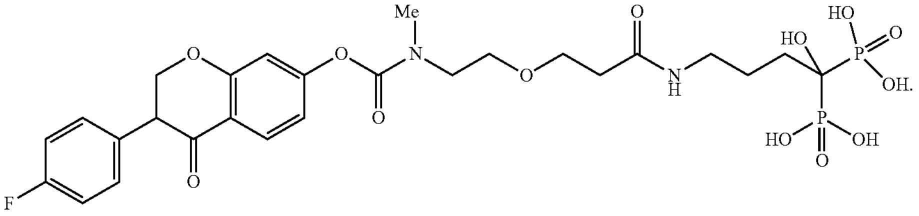 [SMILES: CN(CCOCCC(=O)NCCCC(O)(P(=O)(O)O)P(=O)(O)O)C(=O)Oc1ccc2c(c1)OCC(c1ccc(F)cc1)C2=O]

9. The compound of claim 7, or a pharmaceutically acceptable salt thereof, wherein the compound has the formula:

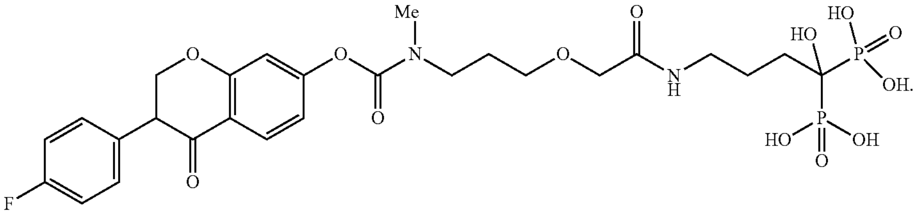 [SMILES: CN(CCCOCC(=O)NCCCC(O)(P(=O)(O)O)P(=O)(O)O)C(=O)Oc1ccc2c(c1)OCC(c1ccc(F)cc1)C2=O]

10. A pharmaceutical composition comprising a pharmaceutically effective amount of the compound of claim 1, or a pharmaceutically acceptable salt thereof, and a pharmaceutically acceptable carrier or excipient.

11. A method of treatment of osteoclast mediated bone degradation in a subject, the method comprising administering to a subject in need thereof a pharmaceutically effective amount of the compound of claim 1, or a pharmaceutically acceptable salt thereof.

12. The compound of claim 1, or a pharmaceutically acceptable salt thereof, wherein the compound has the formula:

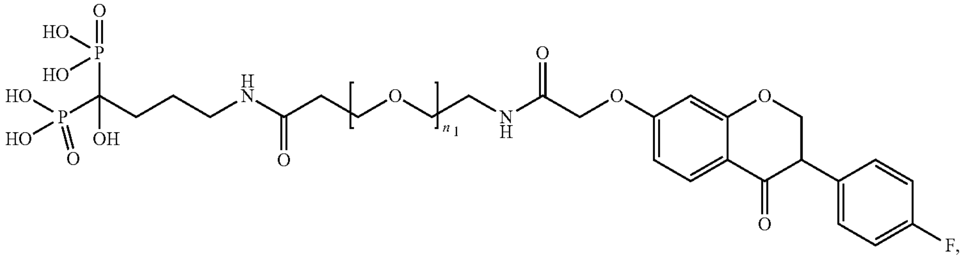

wherein $n_1$ is 1, 2, 4, 5, or 6.

13. The compound of claim 12, or a pharmaceutically acceptable salt thereof, wherein the compound has the formula:

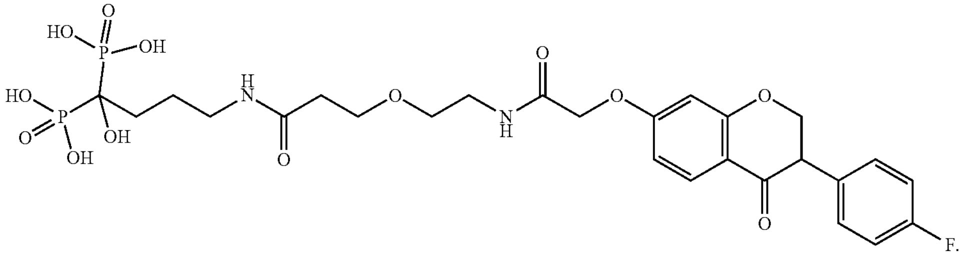 [SMILES: O=C(CCOCCNC(=O)COc1ccc2c(c1)OCC(c1ccc(F)cc1)C2=O)NCCCC(O)(P(=O)(O)O)P(=O)(O)O]

14. The compound of claim 12, or a pharmaceutically acceptable salt thereof, wherein the compound has the formula:

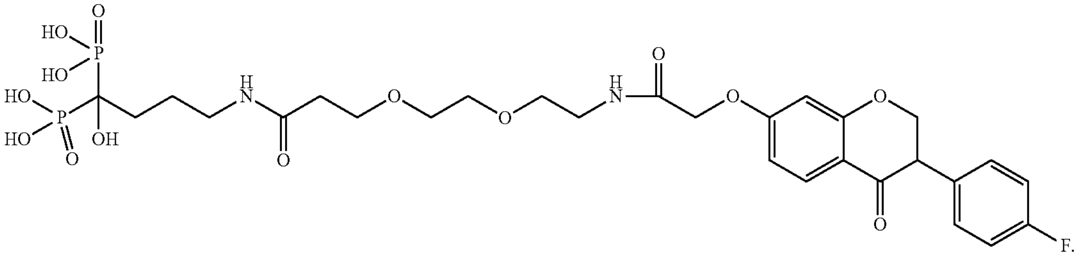 [SMILES: O=C(CCOCCOCCNC(=O)COc1ccc2c(c1)OCC(c1ccc(F)cc1)C2=O)NCCCC(O)(P(=O)(O)O)P(=O)(O)O]

15. The compound of claim 12, or a pharmaceutically acceptable salt thereof, wherein the compound has the formula:

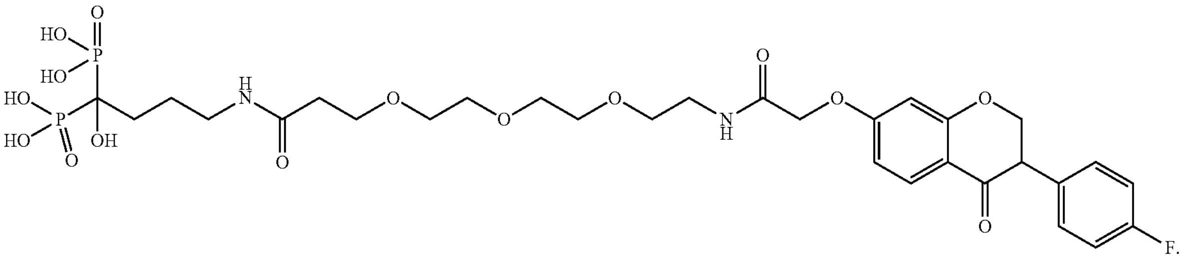 [SMILES: O=C(CCOCCOCCOCCNC(=O)COc1ccc2c(c1)OCC(c1ccc(F)cc1)C2=O)NCCCC(O)(P(=O)(O)O)P(=O)(O)O]

16. A pharmaceutical composition comprising a pharmaceutically effective amount of the compound of claim 12, or a pharmaceutically acceptable salt thereof, and a pharmaceutically acceptable carrier or excipient.

17. A method of treatment of osteoclast mediated bone degradation in a subject, the method comprising administering to a subject in need thereof a pharmaceutically effective amount of the compound of claim 12, or a pharmaceutically acceptable salt thereof.

* * * * *